US008465510B2

(12) United States Patent
Shturman

(10) Patent No.: US 8,465,510 B2
(45) Date of Patent: Jun. 18, 2013

(54) ROTATIONAL ATHERECTOMY SYSTEM WITH ENHANCED DISTAL PROTECTION CAPABILITY AND METHOD OF USE

(75) Inventors: Leonid Shturman, Nyon (CH); Lela Nadirashvili, legal representative, Nyon (CH)

(73) Assignee: Cardio Flow, Inc., Long Lake, MN (US)

( * ) Notice: Subject to any disclaimer, the term of this patent is extended or adjusted under 35 U.S.C. 154(b) by 454 days.

(21) Appl. No.: 12/744,024

(22) PCT Filed: Nov. 21, 2008

(86) PCT No.: PCT/EP2008/065986
§ 371 (c)(1),
(2), (4) Date: Sep. 28, 2010

(87) PCT Pub. No.: WO2009/065927
PCT Pub. Date: May 28, 2009

(65) Prior Publication Data
US 2011/0009888 A1 Jan. 13, 2011

(51) Int. Cl.
*A61B 17/22* (2006.01)
(52) U.S. Cl.
USPC .......................................................... 606/159
(58) Field of Classification Search
USPC ..................... 606/159, 200; 604/19, 264, 187
See application file for complete search history.

(56) References Cited

U.S. PATENT DOCUMENTS

| 4,990,134 A | 2/1991 | Auth |
| 5,127,902 A | 7/1992 | Fischell |
| 5,435,009 A | 7/1995 | Schild et al. |
| 5,681,336 A | 10/1997 | Clement et al. |
| 5,766,192 A | 6/1998 | Zacca |
| 6,132,444 A | 10/2000 | Shturman et al. |
| 2003/0125756 A1 | 7/2003 | Shturman et al. |
| 2005/0228402 A1 | 10/2005 | Hofmann |

FOREIGN PATENT DOCUMENTS

| EP | 0479433 A2 | 4/1992 |
| GB | 2271060 A | 4/1994 |
| WO | 03061457 A | 7/2003 |
| WO | 2006126076 A | 11/2006 |
| WO | 2006126175 A | 11/2006 |
| WO | 2006126176 A | 11/2006 |
| WO | 9714470 A | 4/2007 |

OTHER PUBLICATIONS

International Search Report, corresponding to Int'l Application No. PCT/EP2008/065986 (dated Feb. 26, 2009).

*Primary Examiner* — Elizabeth Houston
(74) *Attorney, Agent, or Firm* — Fish & Richardson P.C.

(57) ABSTRACT

An atherectomy system for removing a stenotic lesion from within a vessel of a patient is disclosed. The system comprising an atherectomy device for reducing the lesion and a separate elongate drainage catheter for evacuating from the treated vessel embolic particles released into the vessel from the stenotic lesion during its reduction by the atherectomy device during an atherectomy procedure. The atherectomy device and the separate elongate drainage catheter are each configured for introduction into the patent's vasculature though separate openings in at least one peripheral artery of the patient.

20 Claims, 43 Drawing Sheets

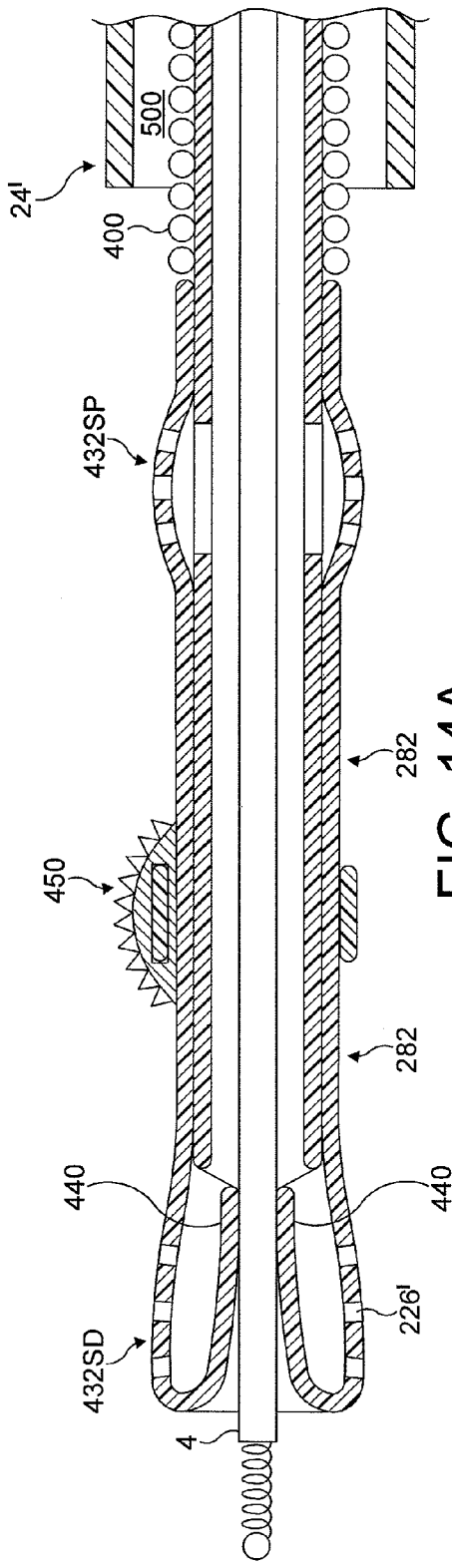
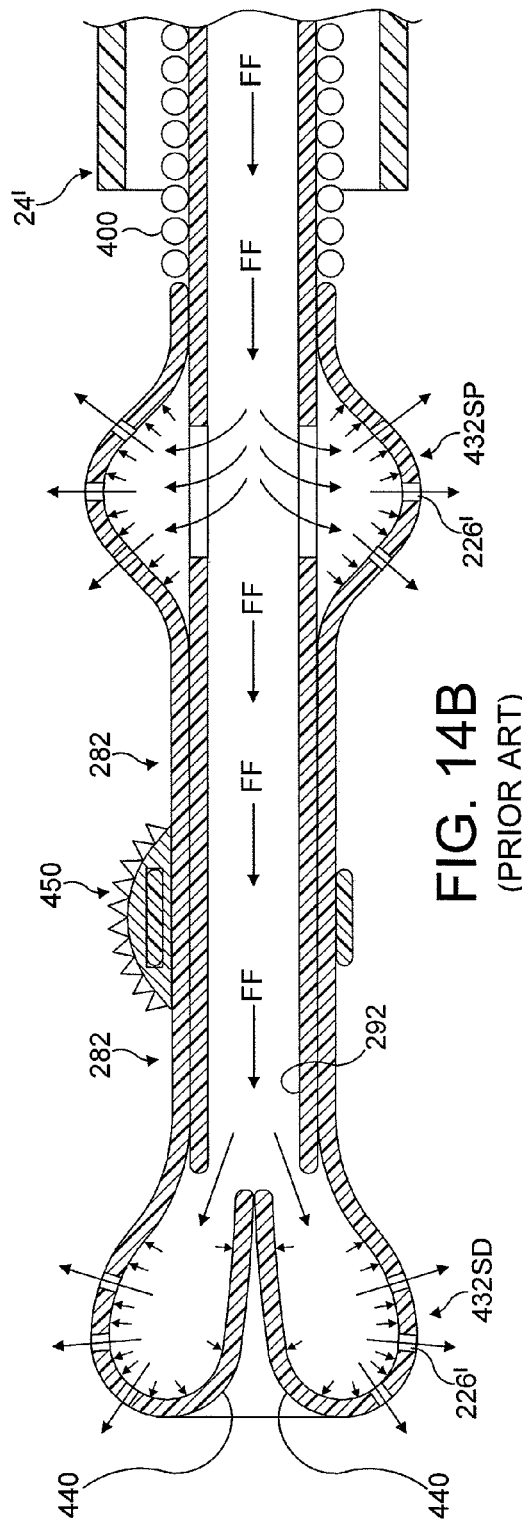
FIG. 14A (PRIOR ART)
FIG. 14B (PRIOR ART)

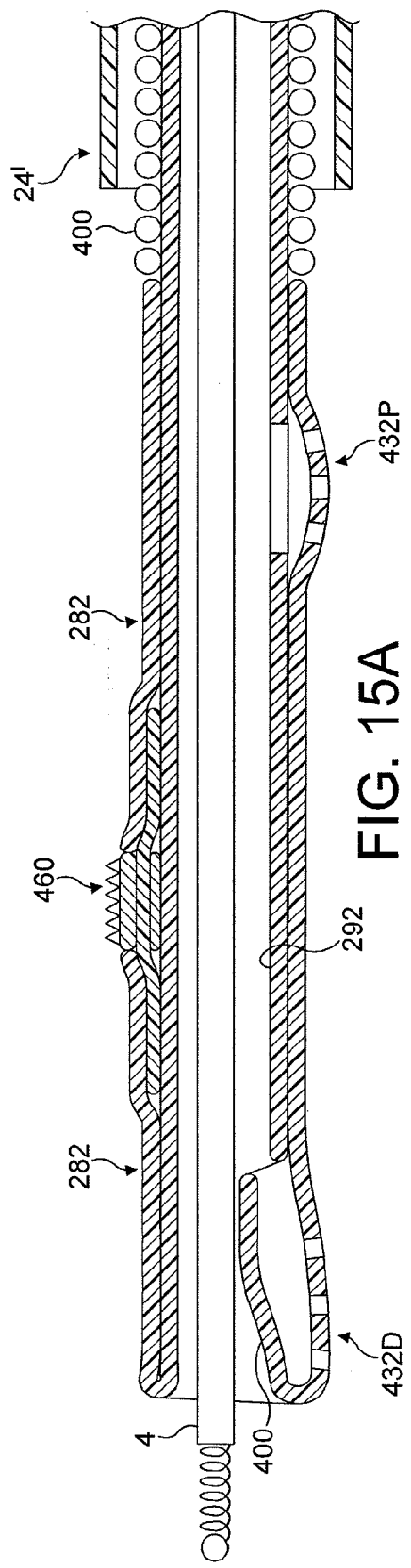
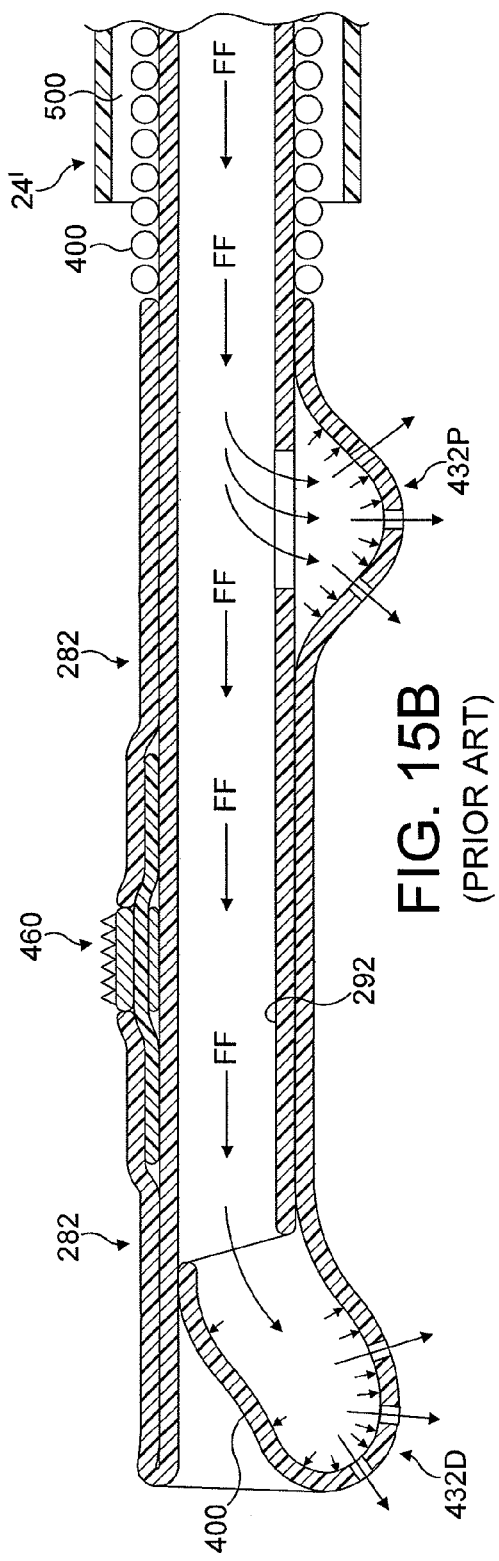
FIG. 15A (PRIOR ART)
FIG. 15B (PRIOR ART)

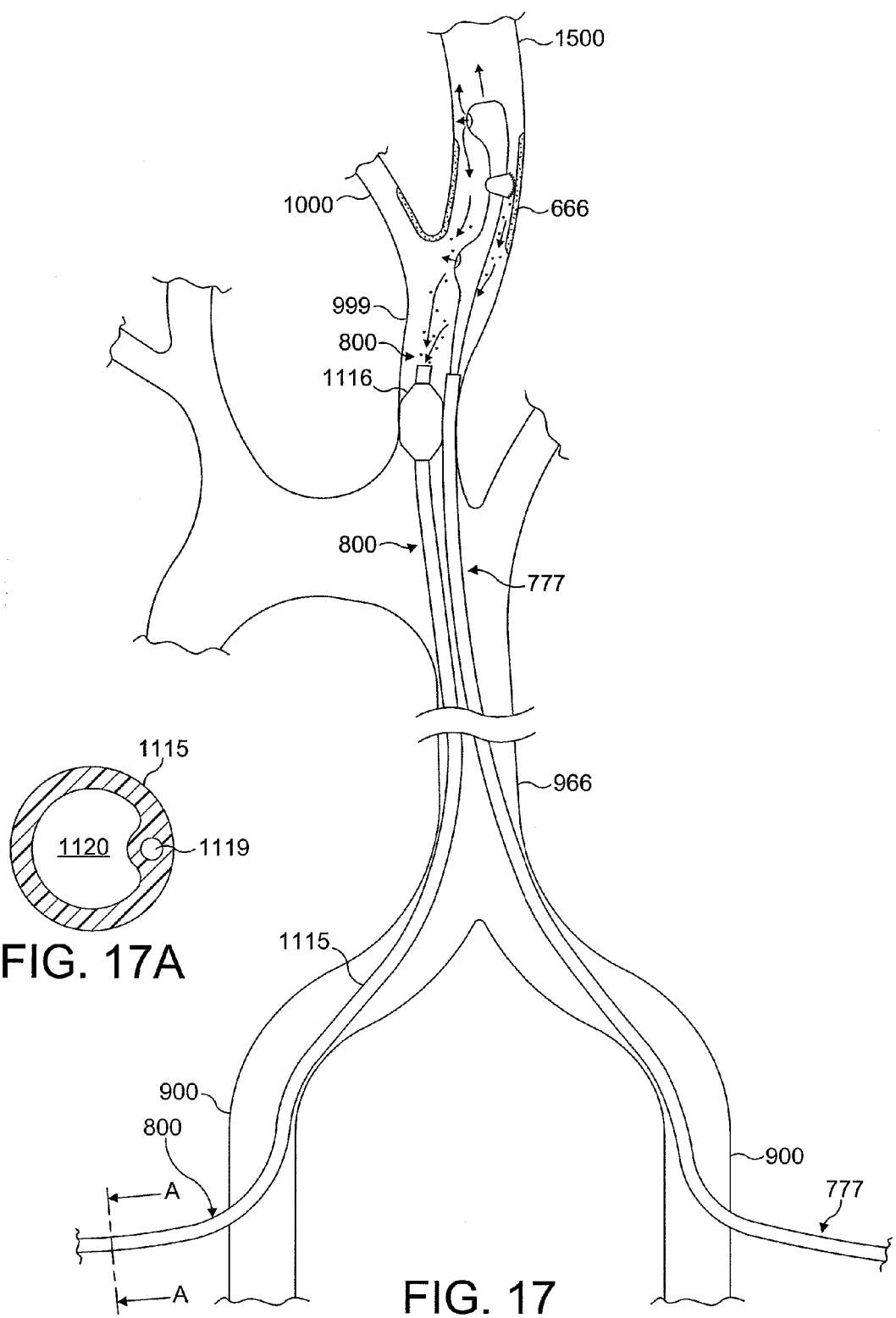

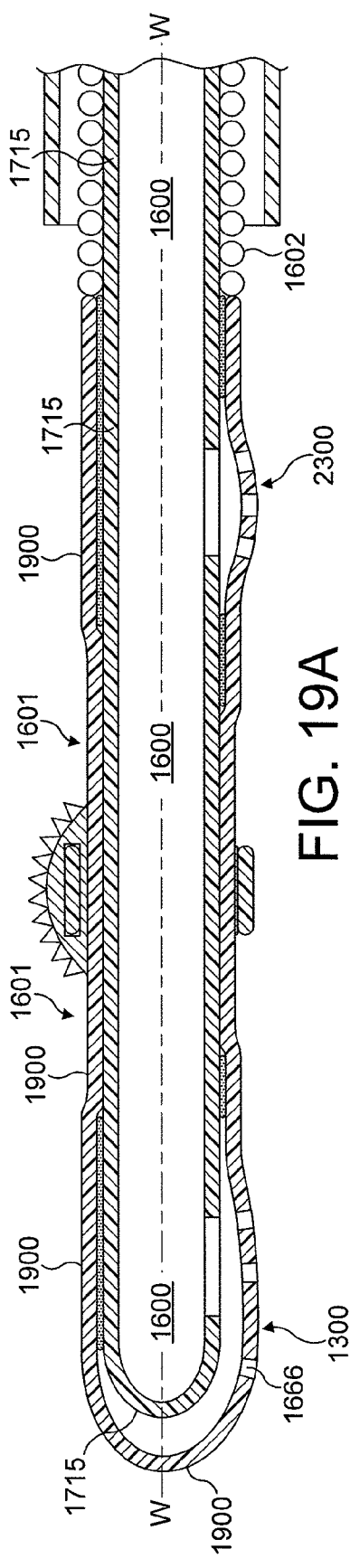
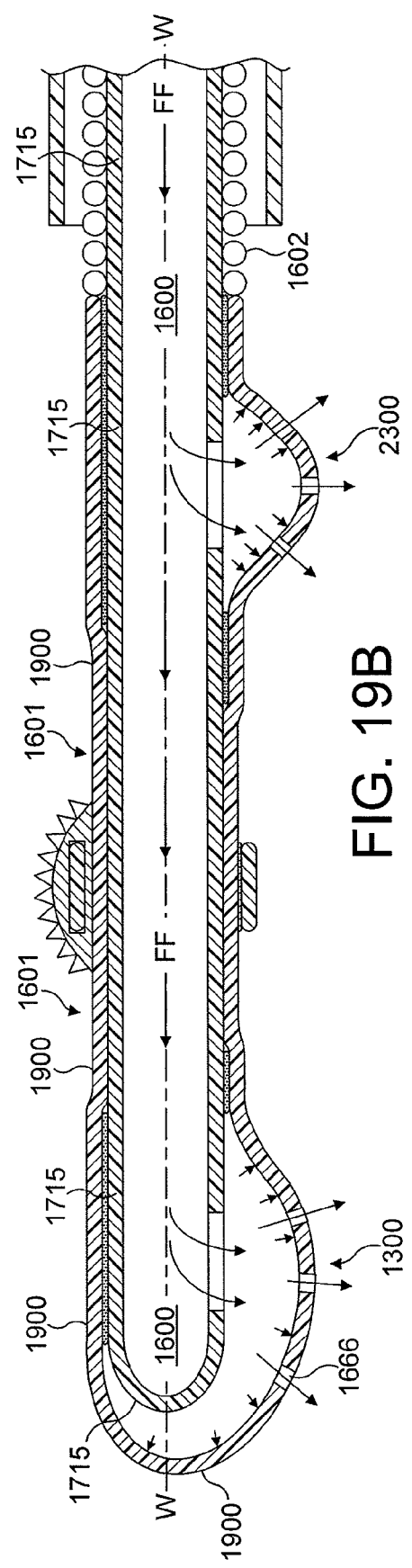
FIG. 19A
FIG. 19B

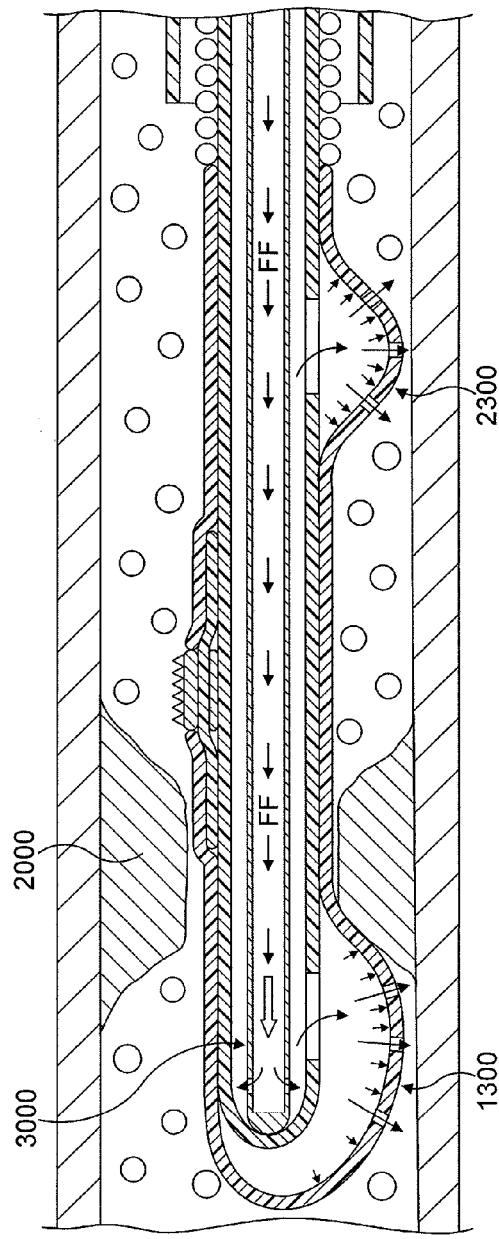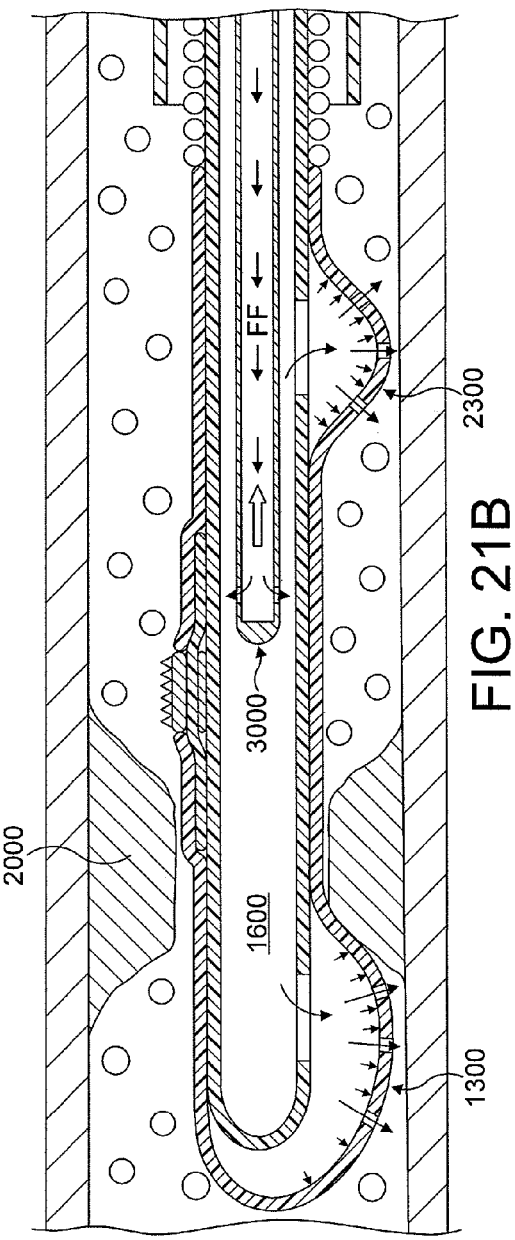
FIG. 21A
FIG. 21B

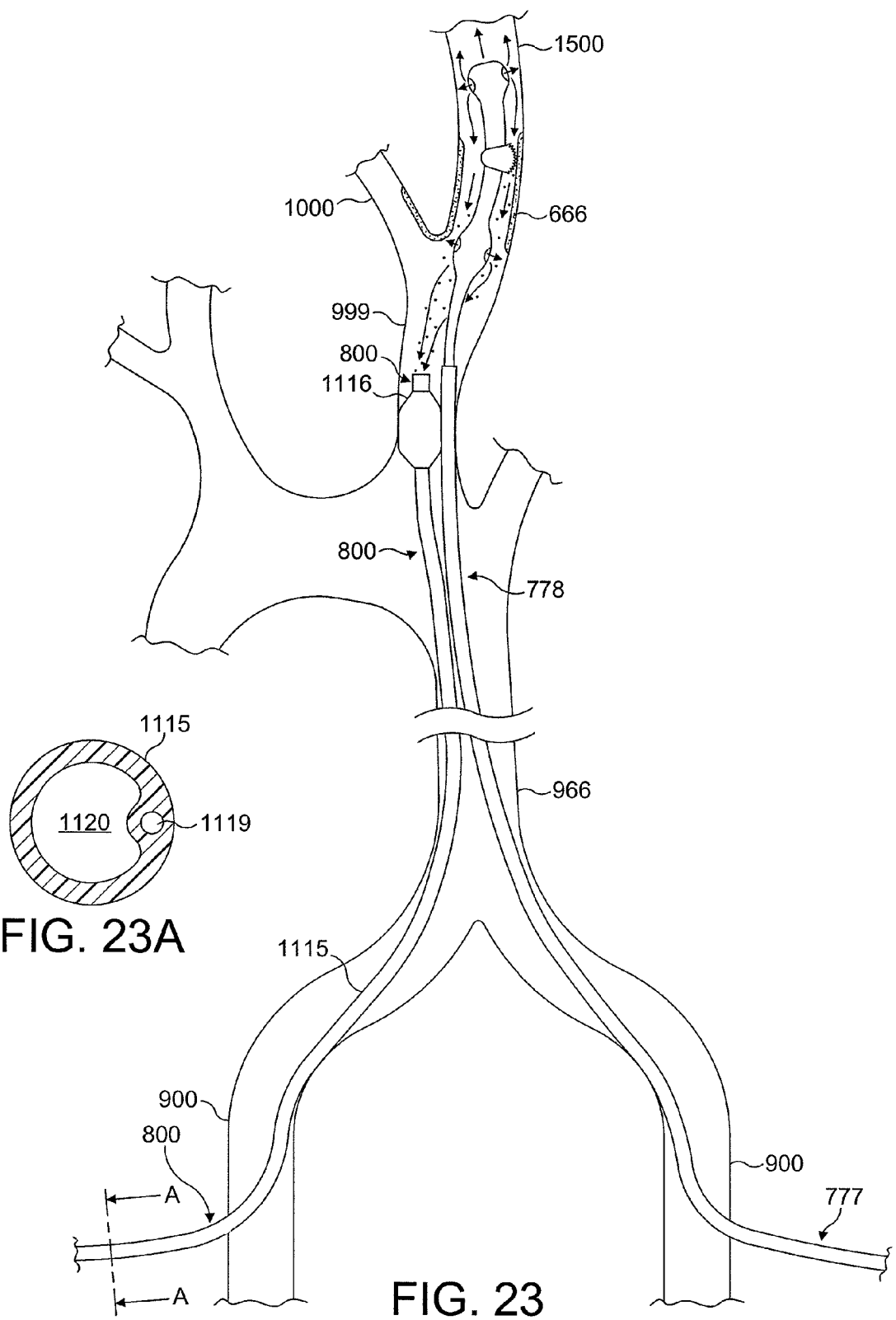

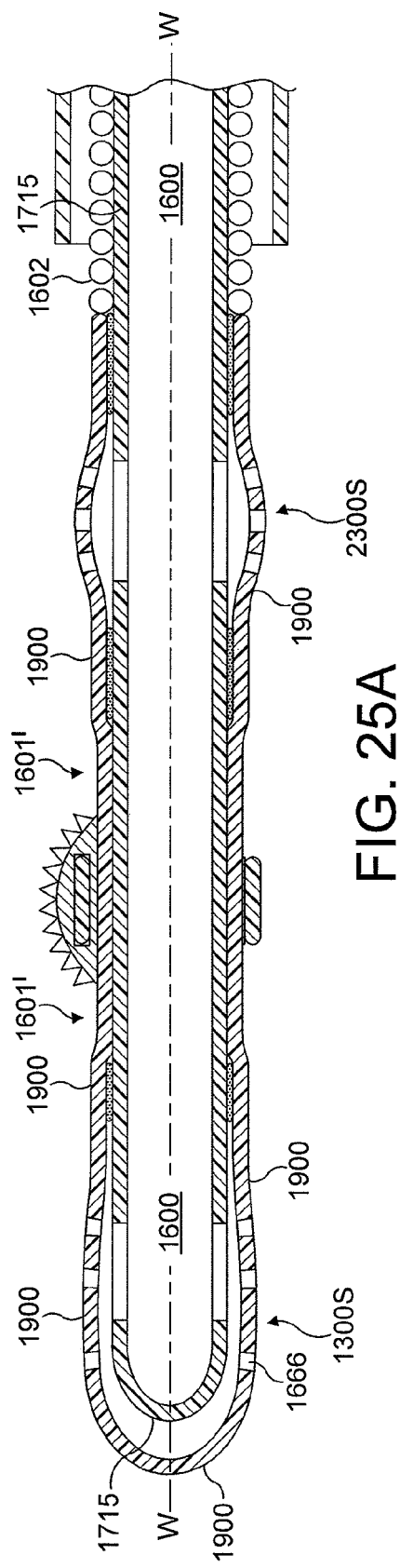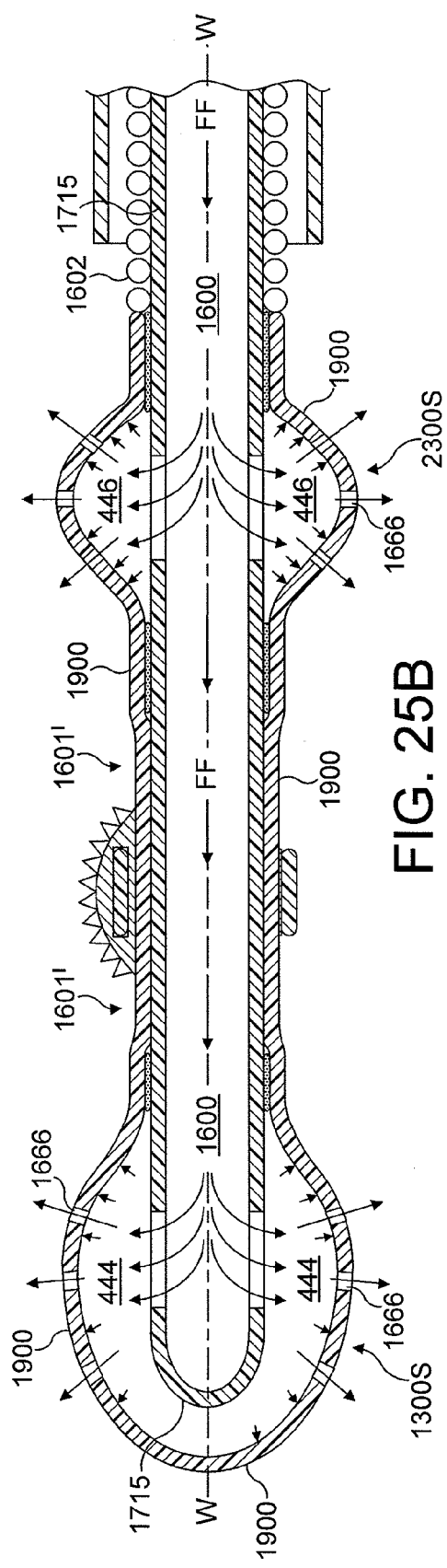
FIG. 25A
FIG. 25B

ROTATIONAL ATHERECTOMY SYSTEM WITH ENHANCED DISTAL PROTECTION CAPABILITY AND METHOD OF USE

CROSS-REFERENCE TO RELATED APPLICATIONS

This application is a national phase application based on PCT/EP2008/065986, filed Nov. 21, 2008, the content of which is incorporated herein by reference, and claims priority of GB Patent Application No. 0722990.9, filed Nov. 23, 2007, the content of which is incorporated by herein by reference.

BACKGROUND OF THE INVENTION

1. Field

The present invention relates to a rotational atherectomy system for removing a stenotic lesion from within a vessel of a patient. More specifically, the invention relates to a rotational atherectomy system with enhanced distal protection capability for removing or reducing stenotic lesion in a human artery by rotating an abrasive element within the artery to partially or completely ablate the stenotic lesion and simultaneously remove out of the patient's body abraded particles (embolic particles or debris) released into the treated artery during the rotational athererctomy procedure. It should be understood that rotational atherectomy devices and rotational athererctomy procedures are often referred to as rotational angioplasty devices and rotational angioplasty procedures. One type of rotational atherectomy devices is referred to as an orbital atherectomy device. All these terms may be used interchangeably herein.

2. Description of the Related Art

Atherosclerosis, the clogging of arteries, is a leading cause of coronary heart disease. Blood flow through the peripheral arteries (e.g., carotid, femoral, renal, etc.), is similarly affected by the development of atherosclerotic blockages. One conventional method of removing or reducing blockages in blood vessels is known as rotational atherectomy. A device and a method for performing the Rotational Atherectomy Procedure are known from U.S. Pat. No. 4,990,134 to Auth. A rotational atherectomy (angioplasty) device based on this patent is commercially available from Boston Scientific Corporation of Natik, Mass., USA.

The distal end portion of this prior art device is shown in FIG. 1. The abrasive burr 1 of this Auth device is attached to a distal end of a hollow flexible drive shaft 2. The abrasive surface of the burr is formed from diamond particles 3. The device is rotated around a special guidewire 4, which is advanced across the stenotic lesion. The device is advanced towards the stenotic lesion around (over) the guidewire. The abrasive burr is positioned against the occlusion and the drive shaft is rotated around the guidewire at extremely high speeds (e.g., 20,000-160,000 rpm). As the abrasive burr rotates, the physician repeatedly advances it towards the stenotic lesion so that the abrasive surface of the burr scrapes against the occluding tissue and disintegrates it, reducing the occlusion and improving the blood flow through the vessel. It should be understood that the terms abrasive burr and abrasive element may be used interchangeably herein.

U.S. Pat. No. 6,132,444 to Shturman (the instant inventor) et al., describes a rotational atherectomy device comprising an abrasive element 11 which is located proximal to and spaced away from a distal end of the drive shaft 12. This abrasive element is formed from diamond particles 13 directly electroplated to wire turns 14 of an enlarged diameter portion 15 of the drive shaft 12. The enlarged diameter portion 15 of the drive shaft is asymmetric and is responsible for providing an abrasive element with a centre of mass which is spaced away from the rotational axis of the drive shaft. The device is rotated around a special guidewire 4 and its eccentric abrasive element 11 is able to open the treated stenotic lesion to a diameter substantially larger than the maximum diameter of the abrasive element.

FIG. 3 shows a side sectional view of the distal end portion of a third embodiment of the rotational atherectomy device of the prior art. The device of FIG. 3 is similar to the device of FIG. 2 except that the abrasive element comprises a prefabricated abrasive crown 16 disposed around the eccentric enlarged diameter portion 15' of the drive shaft 12'. The prefabricated abrasive crown 16 is known from U.S. patent application Ser. No. 10/272,164 to Shturman (the instant inventor). The prefabricated abrasive crown 16 is formed from the diamond particles 13' bonded to a metallic sleeve 17 rather than directly to wire turns 14' of the drive shaft 12'. The device is rotated around a special guidewire 4, and it is commercially produced by Cardiovascular Systems, Inc. of Minnesota, USA.

FIG. 4 illustrates in longitudinal cross-section operation of a rotational atherectomy device known from WO 2006/126176 to Shturman (the current inventor). The rotational atherectomy device (of FIG. 4) comprises a solid eccentric abrasive element and two solid asymmetric support elements 20D, 20P mounted on a hollow flexible drive shaft 21. The solid asymmetric support elements 20D, 20P have their centres of mass spaced away (offset) from a rotational (longitudinal) axis of the drive shaft 21 and, during rotation of the drive shaft, act as counterweights to the eccentric abrasive element 33. Preferably, the rotational atherectomy device includes a distal solid counterweight 20D located on the drive shaft 21 distal to and spaced away from the abrasive element 33 and, a proximal solid counterweight 20P located on the drive shaft 21 proximal to and spaced away from the abrasive element 33. In the most preferred embodiment of the invention, the centre of mass of each of the solid counterweights is separated from the centre of mass of the abrasive element by an angle of 180 degrees around the axis of the drive shaft. When the drive shaft of the rotational atherectomy device with solid counterweights is rotated, centrifugal forces generated by the solid counterweights 20D, 20P and the eccentric abrasive element 33 preferably act in substantially the same plane but in opposite directions. These centrifugal forces cause the distal end portion of the drive shaft to flex and assume a generally bowed or arcuate shape. During rotation of the drive shaft, the abrasive element and each of two solid counterweights move in orbital fashions around the axis of rotation of the drive shaft in orbits that are substantially larger than the respective diameters of the abrasive element or solid counterweights.

The method of use of the device preferably includes the step of partially withdrawing the guidewire 4' into the lumen of the drive shaft such that the distal end of the guidewire 4' is located within the lumen of the drive shaft 21 proximal to the distal end portion of the drive shaft. Pressure applied by the abrasive element and the solid counterweights to the tissue to be removed or to the inner surface of the vessel wall can be easily controlled by adjusting the rotational speed of the drive shaft (i.e. the faster the speed of rotation, the greater the applied pressure), as well as by selecting the respective weights of the abrasive element and solid counterweights. It should be noted that the eccentric disposition of the abrasive element and solid counterweights is not limited to their geometrical eccentric position but, much more importantly, involves the eccentric disposition of their centers of mass with respect to the rotational axis of the drive shaft.

It should be understood that the terms 'solid counterweight', 'solid asymmetric support element' and 'solid support element with a centre of mass offset from a rotational axis of the drive shaft' are used interchangeably throughout the specification.

FIG. 5 illustrates in longitudinal cross-section operation of a fifth embodiment of the rotational atherectomy device of the prior art. This rotational atherectomy device is known from WO 2006/126175 to Shturman (the current inventor) The rotational atherectomy device (of FIG. 5) comprises a solid abrasive element 35 and two solid support elements 22D, 22P mounted on a hollow flexible drive shaft 21'. The device of FIG. 5 is similar to the device of FIG. 4 except that the solid abrasive element 35 and the solid support elements 22D, 22P are symmetric with respect to a rotational (longitudinal) axis of the drive shaft 21' (i.e. they have their centres of mass lying on (the) a rotational (longitudinal) axis of the drive shaft 21'. FIG. 5 illustrates operation of the device in a curved vessel. The device is rotated around a special guidewire 4' which has to be withdrawn into the drive shaft 21' prior to starting its rotation.

In all of the prior art rotational atherectomy devices such as described above with reference to FIGS. 1 to 5, an elongated drive shaft is rotatable around a stationary guidewire. A long proximal portion of the drive shaft is rotatable within an elongated stationary drive shaft sheath 24, said drive shaft sheath 24 forming an annular lumen between the stationary sheath and the rotatable drive shaft. A saline solution or special lubricating fluid is pumped into the annular lumen between the stationary sheath and the rotatable drive shaft. A portion of said saline solution or special lubricating fluid is able to pass between adjacent wire turns of the drive shaft into a second annular lumen formed between the drive shaft and the guidewire thereby reducing friction between the drive shaft and the guidewire. In all of the prior art rotational atherectomy devices referred to above the antegrade flowing saline solution 'FF' or special lubricating fluid enters the treated vessel from a (the) distal end of the stationary drive shaft sheath 24 and thereby entrains and propels distally in an antegrade direction 'FF' along the treated vessel 100 embolic particles (debris) abraded by the abrasive element. The distal migration of the embolic particles along the treated vessel and potential embolisation of very small diameter arteries or capillaries by the embolic particles is of major concern to physicians who practice in this field. Potentially life-threatening complications which may be caused by the embolic particles produced during the rotational atherectomy procedure prevent use of the above described rotational atherectomy devices for treatment of stenotic lesions in the carotid arteries.

Currently, several types of filter based distal embolic protection devices (EPDs) are commercially available for use during balloon angioplasty procedures. These devices are designed to prevent migration of embolic particles larger than 100 microns and cannot prevent migration of very small embolic particles produced during rotational atherectomy procedure. One concept of providing a rotational atherectomy device with distal embolic protection capability is known from U.S. Pat. No. 5,681,336 (to Clement et al.). According to this concept, migration of abraded embolic particles along the treated artery is prevented by temporarily occluding the treated artery distal to the stenotic lesion and aspirating abraded particles from the treated artery prior to deflating a guidewire mounted occlusion balloon. The rotational atherectomy device known from U.S. Pat. No. 5,681,336 (to Clement et al.) has a complicated construction and is difficult to manufacture on a commercial scale.

Disadvantages associated with either limited or completely absent distal embolic protection of all commercially available rotational atherectomy devices have been addressed in WO 2006/126076 to Shturman (the instant inventor). In accordance with WO 2006/126076 every rotational atherectomy device of the prior art described below and shown in FIGS. 6 to 16C differs from the devices of the prior art described above and shown in FIGS. 1 to 5 in that its drive shaft has a fluid impermeable wall and allows an antegrade flow FF of pressurised fluid through a lumen of the drive shaft from a proximal end towards a distal end of the drive shaft. A portion of the pressurised fluid, after entering the treated vessel distal to the abrasive element, flows in a retrograde direction 'RF' around the abrasive element and across the treated stenotic lesion to entrain abraded embolic particles 'EP' and evacuate them from the treated vessel as soon as they have been abraded by the abrasive element of the device. Several embodiments of the device with distal embolic protection capability are disclosed in WO 2006/126076, but in every one of these embodiments the retrograde flowing fluid RF and entrained embolic particles EP are evacuated through an oval lumen formed between a stationary drive shaft sheaf and the rotatable fluid impermeable drive shaft. The retrograde flowing fluid RF and entrained embolic particles EP are evacuated from the patient's body.

FIG. 6 is a side sectional view of the distal end portion of a sixth embodiment of the rotational atherectomy device of the prior art. The device of FIG. 6 is similar to the device of FIG. 4 except that the hollow drive shaft 42 has a fluid impermeable wall. The hollow drive shaft 42 is formed from a torque transmitting coil 43 and a fluid impermeable membrane 47. FIG. 6 shows that the membrane 47 lines an inner surface of the torque transmitting coil 43. FIG. 6 illustrates that this device is provided with distal protection capability, i.e. embolic particles abraded by the abrasive element 33' are evacuated from the treated vessel 100. This device represents one of the embodiments of the rotational atherectomy device described in WO 2006/126076. FIG. 6 shows that pressurised flushing fluid flows in an antegrade direction FF along the lumen of the drive shaft 42 and enters the treated vessel 100 through a luminal opening located distally to the abrasive element. A portion of this fluid flows in a retrograde direction RF around the abrasive element 33' and across the stenotic lesion 105 to entrain embolic particles EP abraded by the abrasive element. These embolic particles are aspirated into an annular lumen formed between the rotatable drive shaft 33' and its stationary sheath 24' and removed from the patient's body. FIG. 6 illustrates the device with a solid eccentric abrasive element 33' and a pair of solid support elements 20D', 20P' which have their centres of mass spaced away (offset) from the rotational (longitudinal) axis of the drive shaft. During rotation of the drive shaft, these solid support elements act as counterweights to the eccentric abrasive element The device of FIG. 6 may be advanced across the stenotic lesion over a conventional guidewire, but the guidewire has to be removed from the device prior to attaching a detachable fluid supply tube to the device.

FIG. 7 is a side sectional view of the distal end portion of a seventh embodiment of the rotational atherectomy device of the prior art. The device of FIG. 7 is similar to the device of FIG. 6 except that the solid abrasive element 35' and the solid support elements 22D', 22P' are symmetric with respect to a rotational (longitudinal) axis of the drive shaft 42' (i.e. they have their centres of mass lying on a rotational (longitudinal) axis of the drive shaft 42'. The hollow drive shaft of FIG. 7 is similar to the hollow drive shaft of FIG. 6 except that a fluid impermeable membrane 47' in FIG. 7 is shown extending around a torque transmitting coil 43' of the drive shaft 43'. FIG. 7 illustrates operation of the device in a curved vessel 100. The device of FIG. 7 has been described in WO 2006/126076 and, as any other device described in WO 2006/126076, it may be (advanced across the stenotic lesion around (over)) (used with) a conventional guidewire. The guidewire has to be removed from the device prior to attaching a detachable fluid supply tube to the device.

FIG. 8 is a side sectional view of the distal end portion of an eighth embodiment of the rotational atherectomy device of the prior art. The device of FIG. 8 is similar to the device of FIG. 6 except that the support elements 222D, 222P are fluid inflatable. These support elements 222D, 222P are in fluid communication with the lumen of the drive shaft 242 and are inflated by pressurised fluid flowing along the lumen of the drive shaft in an antegrade direction FF. Pressurised fluid inflates the support elements 222D, 222P and enters the vessel through outflow openings 225 in the distal support element. FIG. 8 shows that the support elements, when inflated, are asymmetric with respect to a rotational (longitudinal) axis of the drive shaft (i.e. the inflated support elements have there's centres of mass spaced away (offset) from the rotational (longitudinal) axis of the drive shaft). During rotation of the drive shaft, these inflated support elements 222D, 222P act as counterweights to the eccentric abrasive element 235. The device of FIG. 8 has been described in WO 2006/126076 and, as any other device described in WO 2006/126076, it may be (advanced across the stenotic lesion over a conventional guidewire. The guidewire has to be removed from the device prior to connecting (attaching) a detachable fluid supply tube to the device.

FIG. 9 is a side sectional view of the distal end portion of a ninth embodiment of the rotational atherectomy device of the prior art. The device of FIG. 9 is similar to the device of FIG. 8 except that the abrasive element 235' and the fluid inflatable support elements 222D', 222P' shown in FIG. 9 are symmetric with respect to a rotational (longitudinal) axis of the drive shaft (i.e. they all have their centres of mass lying on a rotational (longitudinal) axis of the drive shaft. FIG. 9 shows operation of the device in a curved vessel 100. A stenotic lesion 105 is shown located on an inner curvature of the vessel 100. FIG. 9 illustrates a bias provided to the symmetric abrasive element 235' by a magnetic force or forces. The magnetic force or forces are indicated by arrows marked "MF". The device of FIG. 9 has been described in WO 2006/126076 and, as any other device described in WO 2006/126076, it may be advanced across the stenotic lesion over a conventional guidewire. The guidewire has to be removed from the device prior to connecting a detachable fluid supply tube to the device.

FIG. 9 shows an embodiment in which the centres of mass of the fluid inflatable support elements and the abrasive element are all lying on the longitudinal axis of the drive shaft. However, it is also envisaged to provide an embodiment in which the centre of mass of the abrasive element is spaced radially away from the longitudinal axis of the drive shaft while the centers of mass of both of the distal and proximal fluid inflatable support elements are lying on the longitudinal axis of the drive shaft. Such embodiment may be particularly applicable for use in carotid or femoral arteries.

FIG. 10 is a side sectional view of the distal end portion of a tenth embodiment of the rotational atherectomy device of the prior art. The device of FIG. 10 has been described in to Shturman (the instant inventor). The device of FIG. 10 is similar to the device of FIG. 6 except that the solid counterweights 200D, 200P comprise outflow channels 202D, 202P which extend radially outward with respect to a rotational (longitudinal) axis of the drive shaft 252. FIG. 10 illustrates that pressurised fluid flowing through these outflow channels 202D, 202P forms fluid bearings between the solid counterweights 200D, 200P and the wall of the treated vessel 100. This rotational atherectomy device may be advanced across the stenotic lesion over a conventional guidewire, but the guidewire has to be removed from the device prior to connecting a detachable fluid supply tube to the device.

FIG. 11 is a side sectional view of the distal end portion of an eleventh embodiment of the rotational atherectomy device of the prior art. The device of FIG. 10 has been described in to Shturman (the instant inventor). The device of FIG. 11 is similar to the device of FIG. 10 except that the outflow channels 202SD, 202SP are formed not in the solid counterweights but in the solid support elements 200SD, 200SP which are symmetric with respect to a rotational (longitudinal) axis of the drive shaft. FIG. 11 illustrates operation of the device in a curved vessel.

FIG. 11 shows an embodiment in which the centers of mass of the solid support elements 200SD, 200SP and the abrasive element 333 are lying on the longitudinal axis of the drive shaft 252'. However, it is also envisaged to provide an embodiment in which the centre of mass of the abrasive element is spaced radially away from the longitudinal axis of the drive shaft while the centers of mass of both of the distal and proximal solid support elements are lying on the longitudinal axis of the drive shaft. Such embodiment may be particularly applicable for use in carotid or femoral arteries.

FIG. 12 is a side sectional view of the distal end portion of a twelfth embodiment of the rotational atherectomy device of the prior art. The device of FIG. 12 is similar to the device of FIG. 8 except that the fluid inflatable counterweights 232D, 232P comprise outflow openings 226 located such that pressurised fluid flowing through these openings 226 forms fluid bearings between the fluid inflatable counterweights and the wall of the treated vessel 100.

FIG. 13 is a side sectional view of the distal end portion of a thirteenth embodiment of the rotational atherectomy device of the prior art. The device of FIG. 13 has been described in to Shturman (the instant inventor). The device of FIG. 13 is similar to the device of FIG. 12 except that outflow openings are formed not in the fluid inflatable counterweights but in the fluid inflatable support elements 232SD, 232SP which, when inflated, are symmetric with respect to a rotational (longitudinal) axis of the drive shaft. The outflow openings 226' are located around entire circumferences of the symmetric fluid inflatable support elements such that pressurised fluid flowing through these openings forms fluid bearings between the walls of the fluid inflatable support elements and the wall of the treated vessel 100. FIG. 13 shows an embodiment in which the centers of mass of the fluid inflatable support elements and the abrasive element are lying on the longitudinal axis of the drive shaft. However, it is also envisaged to provide an embodiment in which the centre of mass of the abrasive element is spaced radially away from the longitudinal axis of the drive shaft while the centres of mass of both of the distal and proximal fluid inflatable support elements are lying on the longitudinal axis of the drive shaft. Such embodiment may be particularly applicable for use in carotid or femoral arteries.

FIGS. 13 to 15b (FIG. 13 to FIG. 15b) are side sectional views of the distal end portions of two modifications of a fourteenth embodiment of the rotational atherectomy device of the prior art. FIGS. 13 to 15b illustrate that the torque transmitting coil 400 does not extend to the distal end of the drive shaft 282, and the torque is transmitted to the abrasive element 450 by the fluid impermeable membrane 292 alone. FIGS. 14A and 14B show fluid inflatable support elements 432SD, 432SP which, when inflated, are symmetric with respect to a rotational (longitudinal) axis of the drive shaft 282. FIGS. 15A and 15B show fluid inflatable counterweights 432D, 432P which, when inflated, have their centres of mass offset from the rotational longitudinal axis of the drive shaft 282. FIGS. 15A and 15B illustrate a flexible leaf valve 400 which is formed at the distal end of the drive shaft 282 integrally with a wall of the distal fluid inflatable counterweight 432D. Preferably, the flexible valve 400 is moved to its closed position by pressure of fluid, which is pumped in an antegrade direction FF along the lumen of the drive shaft 282 after advancing the drive shaft over a guidewire 4 across a stenotic lesion to be treated and withdrawing the guidewire from the device. FIGS. 14A and 14B illustrate a flexible leaf valve 440 formed at the distal end of the drive shaft 282 integrally with a wall of the distal fluid inflatable support element 432SD. The distal fluid inflatable support element 432SD, when inflated, is symmetric with respect to a rotational (longitudinal) axis of the drive shaft 282.

It should be noted that FIGS. 14A and 14B show an eccentric abrasive element 450 mounted to the drive shaft between symmetric support elements 432SD, 432SP, while FIGS. 15A and 15B show counterweights 432D, 432P located on both sides of the eccentric abrasive element 460.

FIGS. 16 to 16c (FIG. 16 to FIG. 16c) are side sectional views of the distal end portion of a fifteenth embodiment of the rotational atherectomy device of the prior art. FIGS. 16 to 16c illustrate that the outer torque transmitting coil 470 does not extend to the distal end of the drive shaft, and the torque is transmitted to the abrasive element by the inner torque transmitting coil 480 alone. FIGS. 16 to 16c illustrate formation of a ball valve at the distal end of the drive shaft 282 by a ball 495 and a shoulder 497 at the distal end of the drive shaft.

All Shturman atherectomy devices known from WO 2006/126076 comprise drainage lumen which is integral to the device. Most frequently the drainage lumen has annular shape and (extends) (is formed) between the rotatable drive shaft of the device and its stationary drive shaft sheaf. It should be noted that such annular drainage lumen has limited width and will not permit removal out of the patient's body of embolic particles measuring more than 200 microns in more than one dimension. The drainage lumen need not necessarily have an annular shape but the relatively limited cross sectional dimensions of any drainage lumen formed integrally with an atherectomy device create limitations for aspirating into such drainage lumen and removal out of the patient's body of embolic particles which measure more than 200 microns in more than one dimension.

SUMMARY

The present invention seeks to provide a rotational atherectomy system with distal embolic protection which includes a separate drainage catheter and which will allow particles as large as about 1.5 mm in diameter to be aspirated from a treated vessel and the patient's body through such separate drainage catheter.

BRIEF DESCRIPTION OF THE DRAWINGS

Embodiments of the invention will now be described, by way of example only, with reference to FIGS. 17 to 43 of the accompanying drawings, in which:

FIG. 1 shows an abrasive burr which is attached to a distal end of a hollow flexible drive shaft. The abrasive surface is formed from diamond particles electroplated to a front portion of the solid burr. The device is rotated around a special monofilament guidewire, and it is commercially available.

FIG. 4 illustrates operation of the rotational atherectomy device with the eccentric abrasive element and two counterweights. The device is rotated around a special monofilament guidewire which has to be withdrawn into the drive shaft prior to starting its rotation.

FIG. 5 illustrates operation of the device in a curved vessel. The device is rotated around a special monofilament guidewire which has to be withdrawn into the drive shaft prior to starting its rotation.

FIG. 6 illustrates that this device is provided with distal protection capability, i.e. embolic particles abraded by the abrasive element are evacuated from the treated vessel. FIG. 6 shows that pressurised fluid flows along the lumen of the drive shaft and enters the treated vessel through a luminal opening located distally to the abrasive element. A portion of this fluid flows in a retrograde direction around the abrasive element and across the treated stenotic lesion to entrain embolic particles abraded by the abrasive element. These embolic particles are aspirated into an annular lumen formed between the rotatable drive shaft and its stationary sheaf. The aspirated embolic particles are removed from the patient's body. The device of FIG. 6 may be advanced across the stenotic lesion over a conventional guidewire, but the guidewire has to be removed from the device prior to attaching a detachable fluid supply tube to the device.

FIG. 8 shows that the support elements, when inflated, are asymmetric with respect to a rotational (longitudinal) axis of the drive shaft and, during rotation of the drive shaft, act as counterweights to the eccentric abrasive element. The device of FIG. 8 may be advanced across the stenotic lesion over a conventional guidewire, but the guidewire has to be removed from the device prior to attaching a detachable fluid supply tube to the device.

FIG. 9 illustrates operation of the device in a curved vessel.

FIG. 10 illustrates that pressurised fluid flowing through these channels forms fluid bearings between the counterweights and a wall of the treated vessel.

FIG. 11 illustrates operation of the device in a curved vessel.

FIGS. 14A to 15B are side sectional views of distal end portions of two modifications of a fourteenth embodiment of the rotational atherectomy device of the prior art. These figures illustrate formation of two types of a leaf valve at the distal end of the drive shaft.

FIG. 17 illustrates a first embodiment of a rotational atherectomy system with enhanced distal embolic protection capability of the present invention, the rotational atherectomy system comprising a rotational atherectomy device with counterweights and a separate drainage catheter, the retrograde flowing fluid being aspirated into the separate drainage catheter, both the rotational atherectomy device and the drainage catheter being shown inserted through separate openings located in the femoral arteries of the patient and meeting in the aorta, the drainage catheter extending into the common carotid artery while the rotational atherectomy device passes through the common carotid artery and extends further into the treated internal carotid artery. FIG. 17 illustrates that the openings in the walls of the fluid inflatable counterweights of the device are located such that pressurized fluid flowing through the openings forms fluid bearings between the walls of the fluid inflated counterweights and a wall of the treated vessel. FIG. 17 shows that an occlusion balloon is mounted to a catheter shaft of the drainage catheter. The occlusion balloon has been inflated in the common carotid artery for temporarily engaging the atherectomy device and the drainage catheter with each other and for restricting flow of fluids towards and away from the treated stenotic lesion. FIG. 17 shows that the retrograde flowing fluid and embolic particles are aspirated into the drainage lumen of the drainage catheter.

FIG. 17A is a cross-sectional view of the drainage catheter taken along the line A-A shown in FIG. 17;

FIGS. 19A and 19B illustrate a preferred embodiment of the rotational atherectomy device with counterweights which may be used as a rotational atherectomy device of the rotational atherectomy system of the invention.

The rotational atherectomy device shown in FIGS. 19A and 19B differs from the prior art devices shown in FIGS. 1 to 16C in that it does not require a guidewire for advancement towards and across a stenotic lesion to be treated. FIGS. 19A and 19B show that the distal fluid inflatable counterweight is formed from a single fluid impermeable membrane which extends around an anchoring sleeve of the device. This fluid impermeable membrane crosses a longitudinal axis of a long lumen of the device at the distal end of the device and prevents pressurized fluid flowing along the long lumen from entering the treated vessel in the direction of said longitudinal axis. FIG. 19B shows that the pressurized fluid has to pass through and inflate the distal fluid inflatable counterweight, prior to exiting from the device through outflow openings in the distal fluid inflatable counterweight in a direction different from the direction of the longitudinal axis of the long lumen of the device. FIGS. 19A and 19B show that the long lumen of the device, the lumen of the drive shaft of the device and a torque transmitting coil of the drive shaft have one common longitudinal axis.

FIGS. 21A and 21B illustrate another modification of the preferred embodiment of the rotational atherectomy device with counterweights shown in FIGS. 19A and 19B. FIGS. 21A and 21B illustrate the rotational device with fluid inflatable counterweights which has been advanced across the stenotic lesion to a position in which the distal fluid inflatable counterweight has been located distal to the stenotic lesion and the proximal fluid inflatable counterweight has been intentionally located proximal to the stenotic lesion to be treated. The device of FIGS. 21A and 21B is similar to the device of FIGS. 19A and 19B, but differs in that it comprises an elongate core element disposed in the lumen of the drive shaft to stiffen the drive shaft and thereby assist in the advancement of the device along the vessel towards and across the stenotic lesion. The elongate core element comprises a long lumen, said lumen being in fluid communication with the lumen of the drive shaft through an opening located in a wall of the core element adjacent to its distal end. The continuous flow of the pressurized fluid from the lumen of the core element into the lumen of the drive shaft assists in removing the core element from the lumen of the drive shaft without changing position of the device in the treated vessel. Furthermore, the distal support element, when inflated, may be anchored distal to the stenotic lesion. Such inflating and anchoring of the distal support element against the stenotic lesion may help in removing the core element from the lumen of the drive shaft without changing position of the device in the treated vessel.

FIG. 22 shows that pressurized fluid is exiting from the device only through outflow openings in the distal fluid inflatable counterweight. FIG. 22 shows that the openings in the walls of the fluid inflatable counterweights are located such that pressurized fluid flowing through the openings forms fluid bearings between the walls of the fluid inflated counterweights and a wall of the treated vessel.

FIG. 23 illustrates a second embodiment of the rotational atherectomy system with enhanced distal protection capability. The system of FIG. 23 is similar to the system of FIG. 17 except that the rotational atherectomy device of FIG. 23, instead of counterweights, has support elements having centres of mass lying along the rotational (longitudinal) axis of the drive shaft of the device;

FIG. 23A is a cross-sectional view of the drainage catheter taken along the line A-A shown in FIG. 23;

FIG. 24 illustrates that the openings in the walls of the fluid inflatable support elements of the rotational atherectomy device are located such that pressurized fluid flowing through the openings forms fluid bearings between the walls of the fluid inflated support elements and a wall of the treated vessel. FIG. 24 shows that an occlusion balloon is mounted to a catheter shaft of the drainage catheter. The occlusion balloon has been inflated in the common carotid artery for temporarily engaging the atherectomy device and the drainage catheter with each other and for restricting flow of fluids towards and away from the treated stenotic lesion.

FIGS. 25A and 25B illustrate a preferred embodiment of the rotational atherectomy device with fluid inflatable support elements which may be used as a rotational atherectomy device of the second embodiment of the rotational atherectomy system of the invention. The rotational atherectomy device shown in FIGS. 25A and 25B is similar to the rotational atherectomy device shown in FIGS. 19A and 19B, but differs in that the centres of mass of the inflatable support elements are laying on the longitudinal axis of the torque transmitting coil and of the lumen of the drive shaft. FIG. 25B shows the device of FIG. 25A after an antegrade flow of fluid has been initiated and the support elements have been inflated. FIG. 25B illustrates that fluid inflatable spaces within the support elements extend uniformly around the longitudinal axis of the torque transmitting coil and the lumen of the drive shaft, therefore providing the fluid inflated support elements with centres of mass which are laying on the longitudinal axis of the torque transmitting coil and the lumen of the drive shaft.

FIG. 27 shows that pressurized fluid is exiting from the device only through outflow openings in the fluid inflatable support elements. FIG. 27 shows that the openings in the walls of the fluid inflatable support elements are located such that pressurized fluid flowing through the openings forms fluid bearings between the walls of the fluid inflated support elements and a wall of the treated vessel. FIG. 27 shows that an occlusion balloon is mounted to a catheter shaft of the drainage catheter. The occlusion balloon has been inflated in the common carotid artery for temporarily engaging the atherectomy device and the drainage catheter with each other and for restricting flow of fluids towards and away from the treated stenotic lesion. FIG. 27 shows that the retrograde flowing fluid and embolic particles are aspirated into the drainage lumen of the drainage catheter.

FIG. 28 shows that the rotational atherectomy device and the drainage catheter have been introduced into the patient's vasculature through separate openings located in the radial arteries of the patient. The atherectomy device and the drainage catheter are meeting in the aorta and extending into the treated femoral artery of a patient. FIG. 28 shows that an occlusion balloon is mounted to a catheter shaft of the drainage catheter. The occlusion balloon has been inflated in the femoral artery proximal to the treated stenotic lesion for temporarily engaging the atherectomy device and the drainage catheter with each other and for restricting flow of fluids towards and away from the treated stenotic lesion. The retrograde flowing fluid and embolic particles are aspirated into the drainage lumen of the drainage catheter.

FIG. 33 shows that the rotational atherectomy system of the third embodiment includes an orbital atherectomy device of the prior art shown in FIG. 3 but it should be understood that it may instead include a classic rotational atherectomy device of the prior art shown in FIG. 1.

FIG. 34 shows that tibial arteries and the most distal segment of the popliteal artery have been occluded by an inflated external occlusion cuff so that any embolic particles abraded by the atherectomy device and not entrained in the retrograde flowing flushing fluid accumulate distal to the site of the treated stenotic area but proximal to a point at which the inflated occlusion cuff has compressed the treated vessel or its distal branches.

FIG. 35 also shows that the rotational atherectomy device has been withdrawn proximally away from the stenotic lesion to afford movement of the drainage catheter closer to the accumulated embolic particles;

FIG. 30 shows that the zip fastener extends over the patient's tibia (a front aspect of the patient's calf);

FIG. 42 shows an inflatable occlusion cuff having a shape of a sock and comprising a zip fastener which extends over the lateral aspect of the patient's calf;

DETAILED DESCRIPTION

Figure 1:
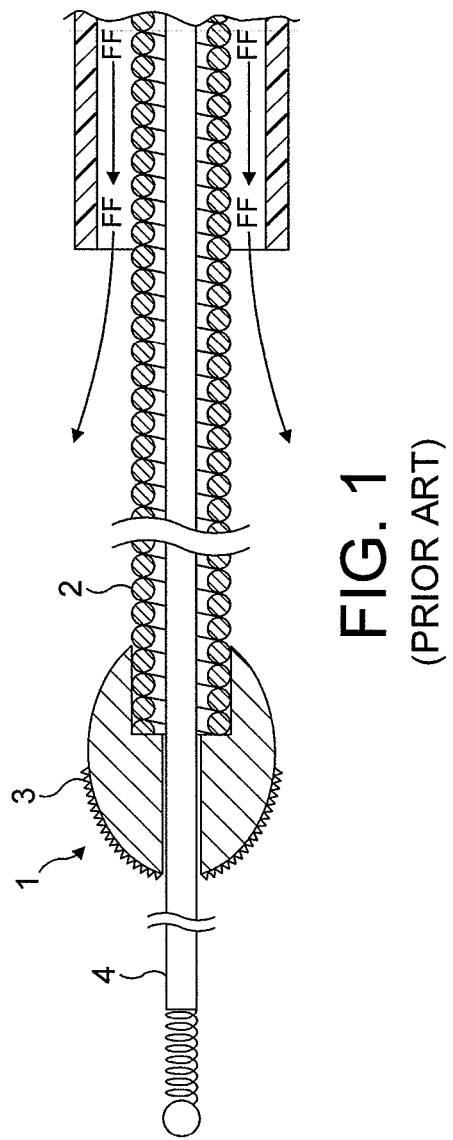
FIG. 1 is a side sectional view of a distal end portion of a first embodiment of the rotational atherectomy device of the prior art.
Figure 2:
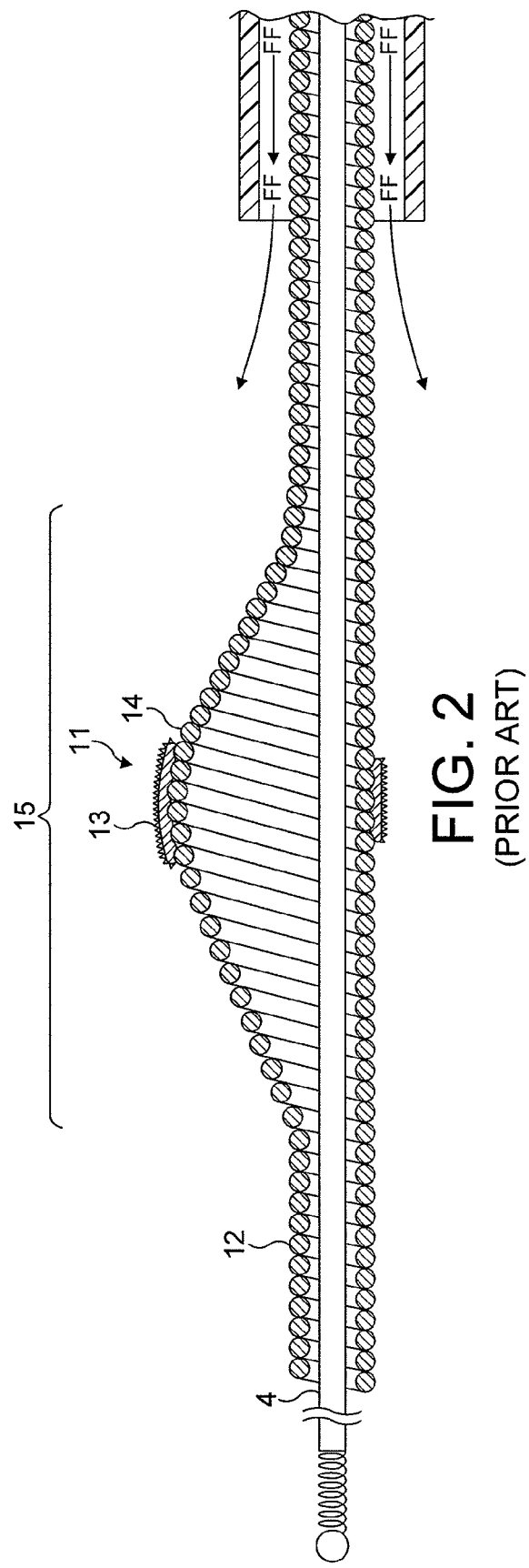
FIG. 2 is a side sectional view of a distal end portion of a second embodiment of the rotational atherectomy device of the prior art. The abrasive element of FIG. 2 has an abrasive element which is located proximal to and spaced away from a distal end of the drive shaft. This abrasive element is formed from diamond particles electroplated directly to wire turns of an enlarged diameter portion of the drive shaft. The enlarged diameter portion of the drive shaft is asymmetric and is responsible for providing the abrasive element with a centre of mass which is spaced away from the rotational axis of the drive shaft. The device is rotated around a special monofilament guidewire.
Figure 3:
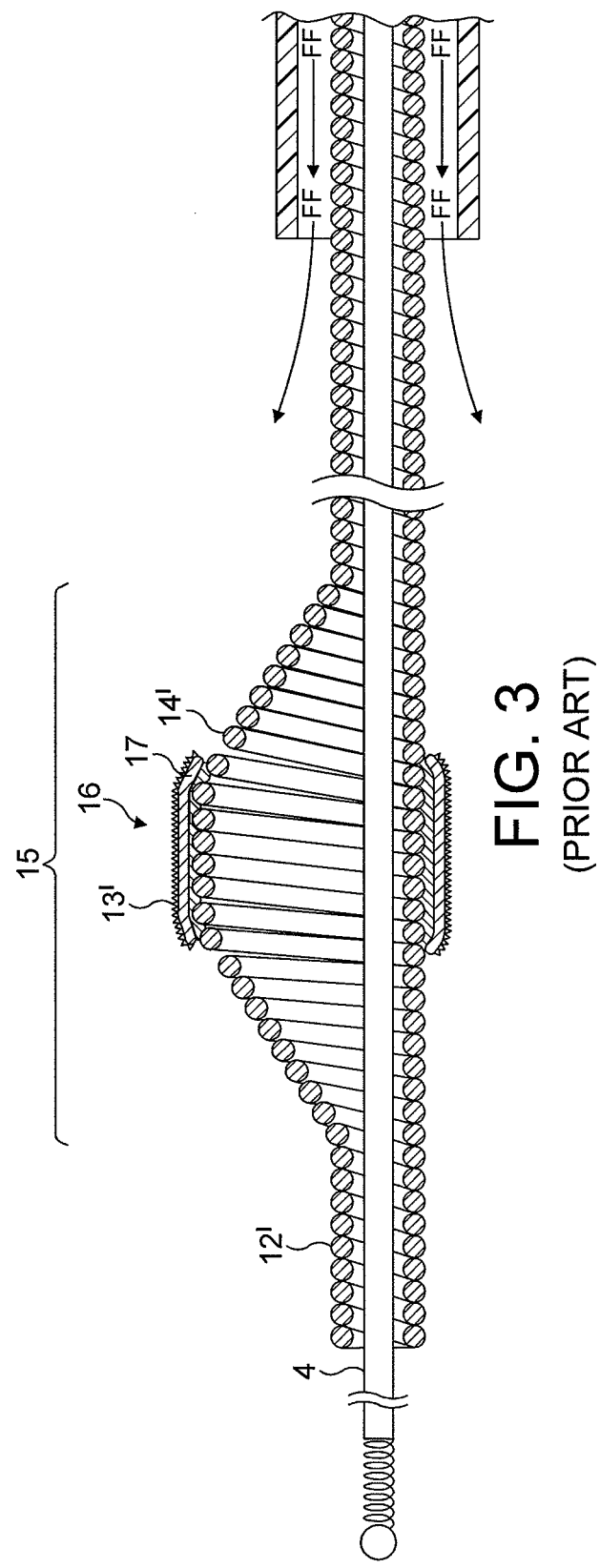
FIG. 3 is a side sectional view of a distal end portion of a third embodiment of the rotational atherectomy device of the prior art. The device of FIG. 3 is similar to the device of FIG. 2 except that the abrasive element comprises a prefabricated abrasive crown disposed around the eccentric enlarged diameter portion of the drive shaft. The prefabricated abrasive crown is formed from diamond particles bonded to a metallic sleeve rather than directly to wire turns of the drive shaft. The device is rotated around a special monofilament guidewire, and it is commercially available.
Figure 4:
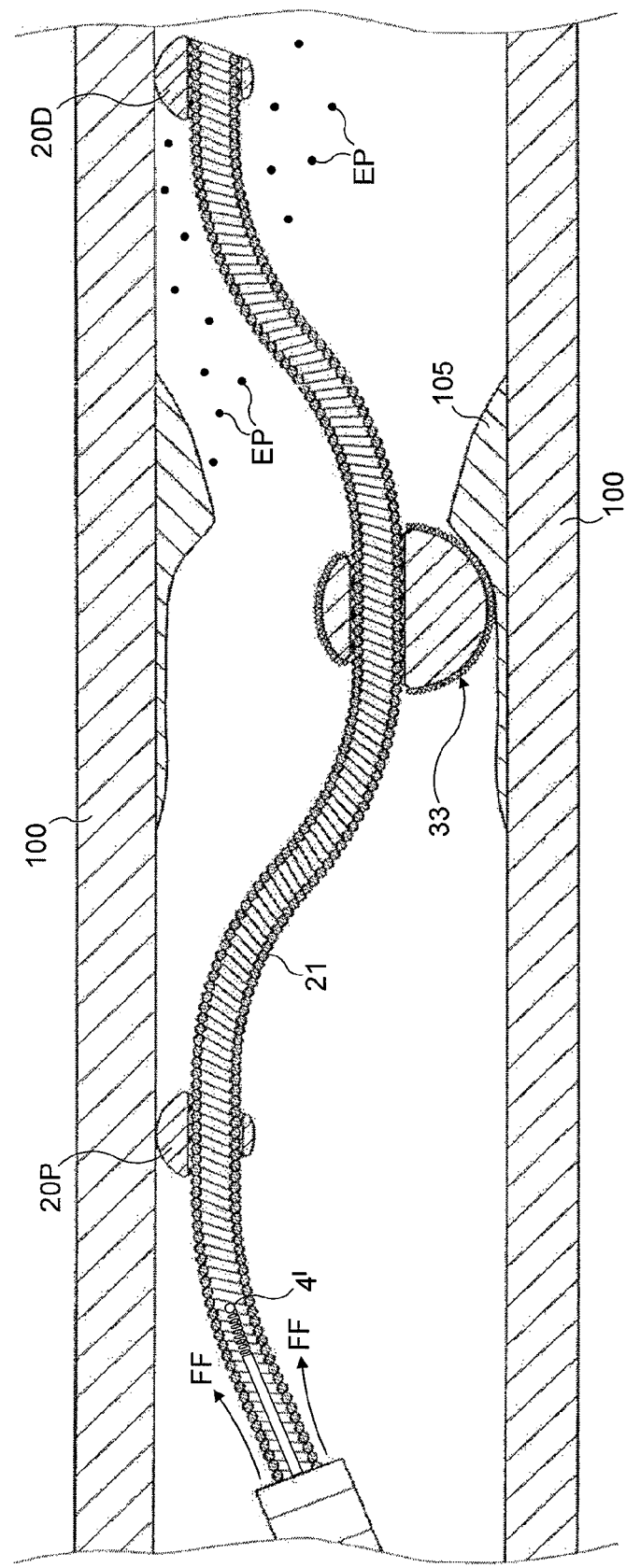
FIG. 4 is a side sectional view of a distal end portion of a fourth embodiment of the rotational atherectomy device of the prior art. The rotational atherectomy device of FIG. 4 comprises a solid eccentric abrasive element and two solid support elements mounted on a hollow flexible drive shaft. The solid support elements are asymmetric with respect to a rotational (longitudinal) axis of the drive shaft and, during rotation of the drive shaft, act as counterweights to the eccentric abrasive element.
Figure 5:
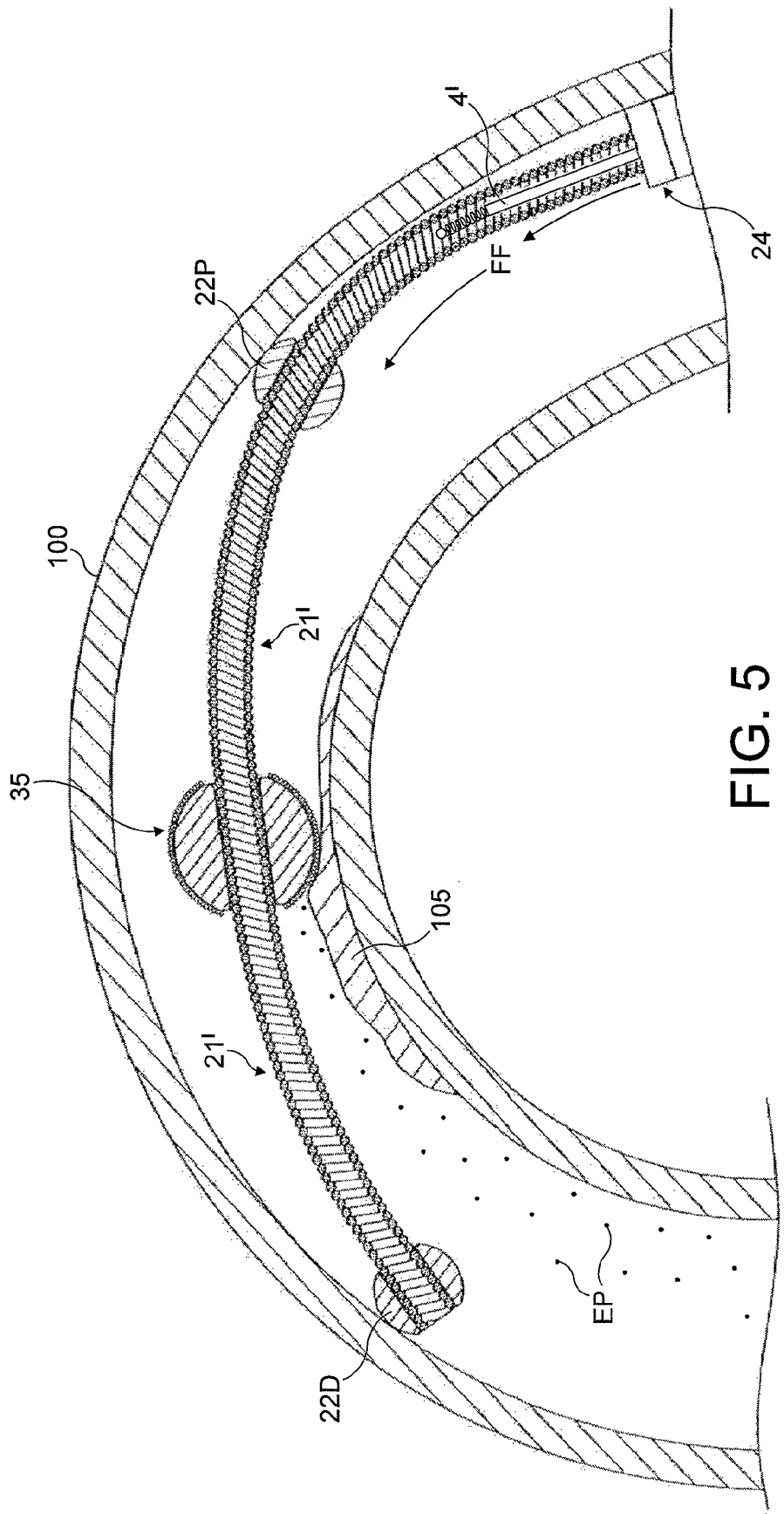
FIG. 5 is a side sectional view of a distal end portion of a fifth embodiment of the rotational atherectomy device of the prior art. The device of FIG. 5 is similar to the device of FIG. 4 except that the solid abrasive element and the solid support elements are symmetric with respect to a rotational (longitudinal) axis of the drive shaft.
Figure 6:
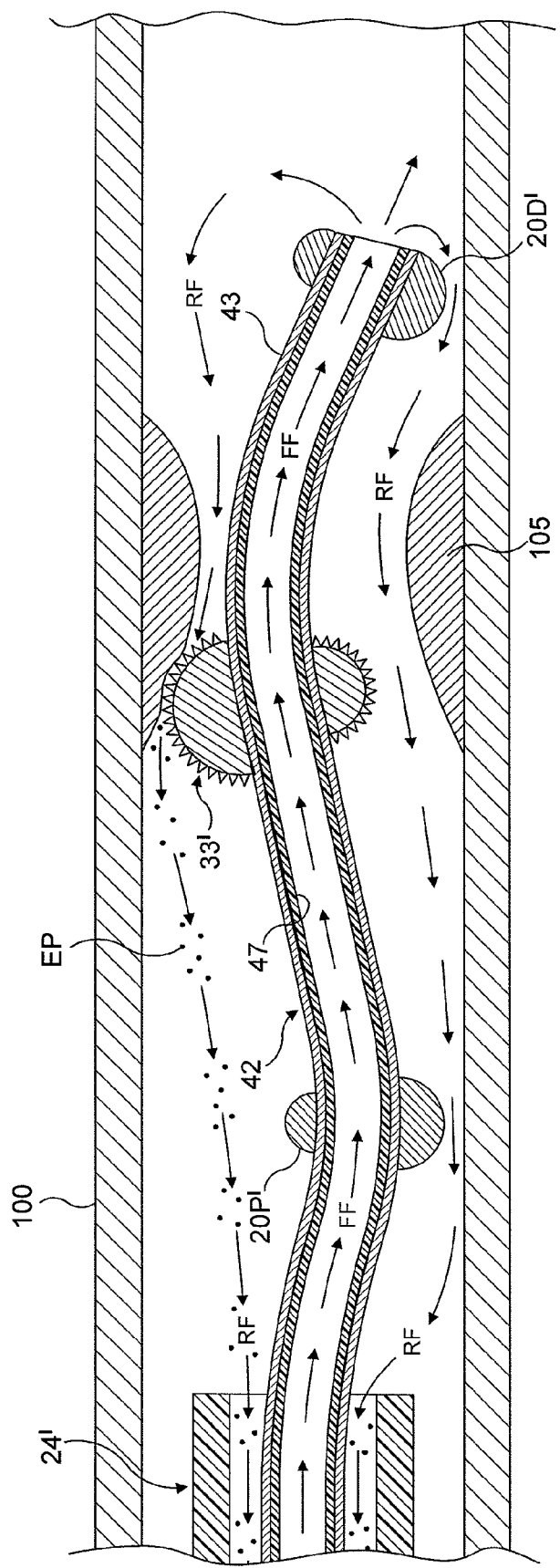
FIG. 6 is a side sectional view of a distal end portion of a sixth embodiment of the rotational atherectomy device of the prior art. The device of FIG. 6 is similar to the device of FIG. 4 except that the hollow rotatable drive shaft has a fluid impermeable wall.
Figure 7:
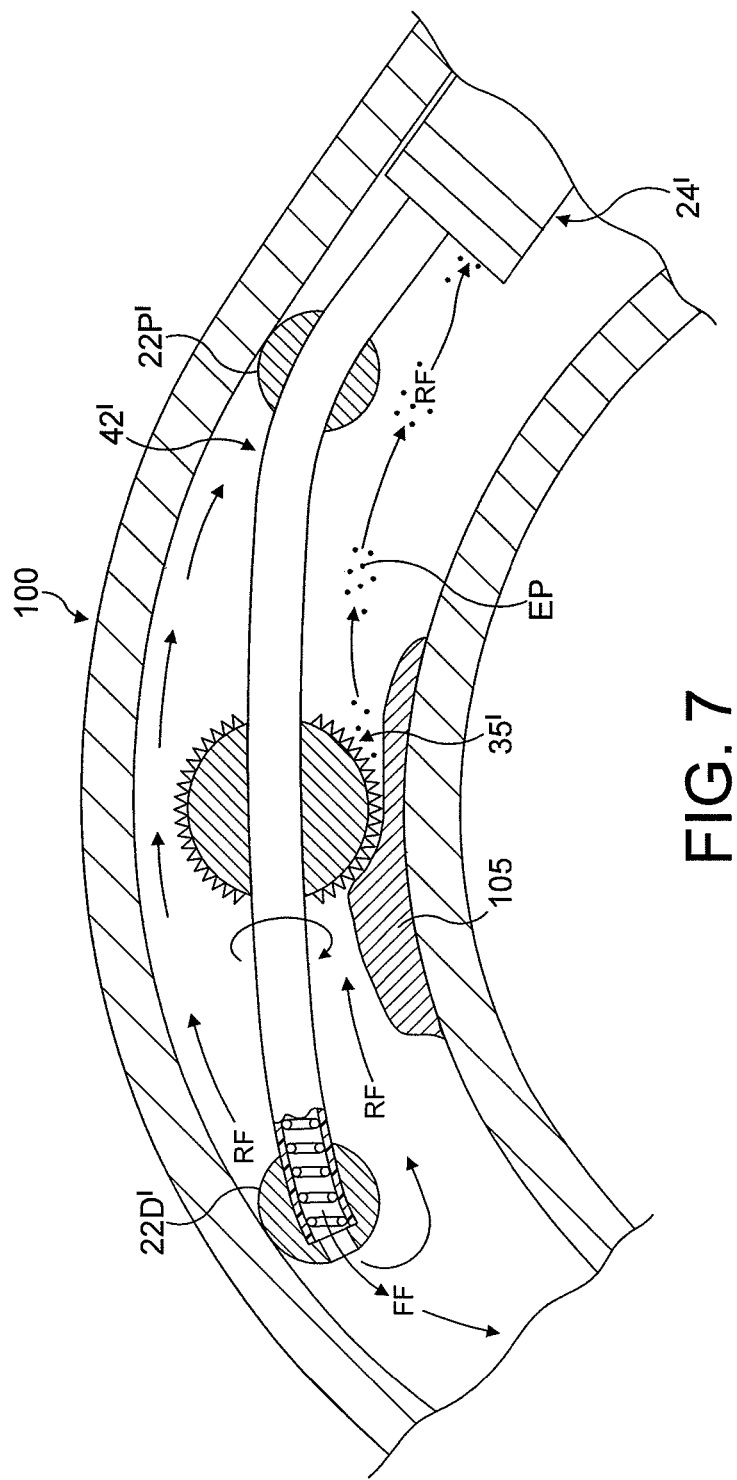
FIG. 7 is a side sectional view of a distal end portion of a seventh embodiment of the rotational atherectomy device of the prior art. The device of FIG. 7 is similar to the device of FIG. 6 except that the solid abrasive element and the solid support elements are symmetric with respect to a rotational (longitudinal) axis of the drive shaft.
Figure 8:
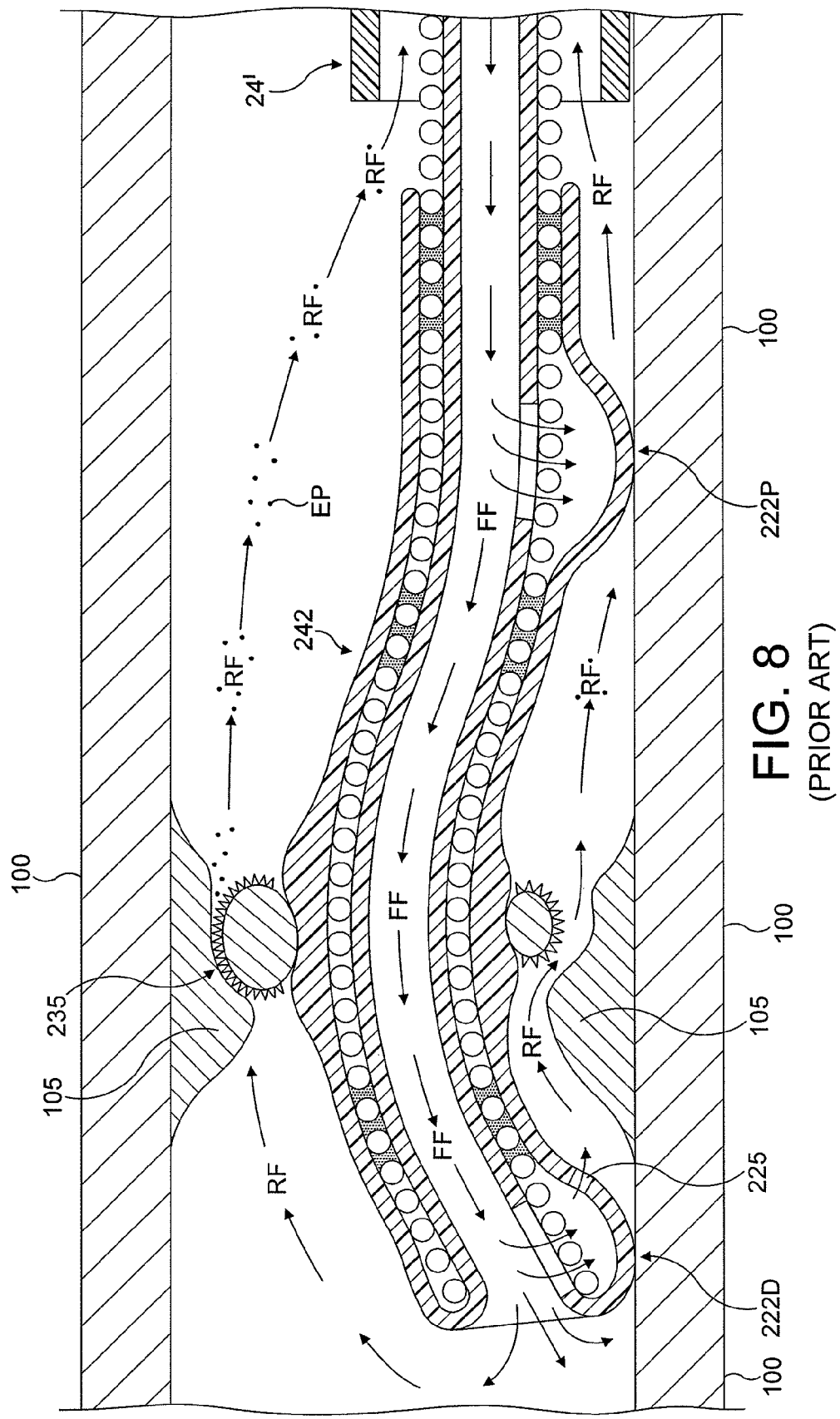
FIG. 8 is a side sectional view of a distal end portion of an eighth embodiment of the rotational atherectomy device of the prior art. The device of FIG. 8 is similar to the device of FIG. 6 except that the support elements are fluid inflatable. These support elements are in fluid communication with the lumen of the drive shaft and are inflated by pressurised fluid flowing along the lumen of the drive shaft. The pressurised fluid inflates the support elements and enters the vessel through outflow openings therein.
Figure 9:
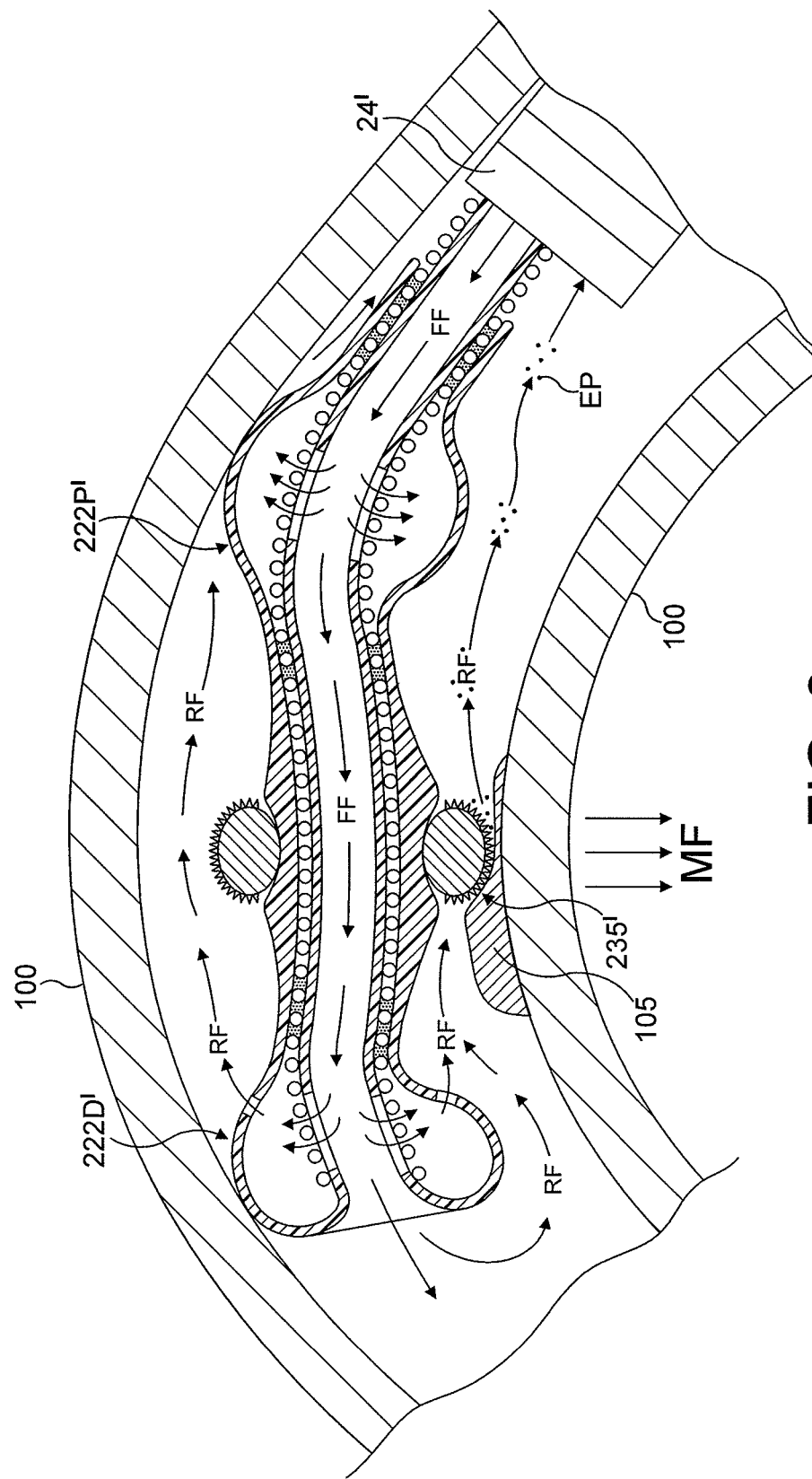
FIG. 9 is a side sectional view of a distal end portion of a ninth embodiment of the rotational atherectomy device of the prior art. The device of FIG. 9 is similar to the device of FIG. 8 except that the abrasive element and the fluid inflatable support elements are symmetric with respect to a rotational (longitudinal) axis of the drive shaft.
Figure 10:
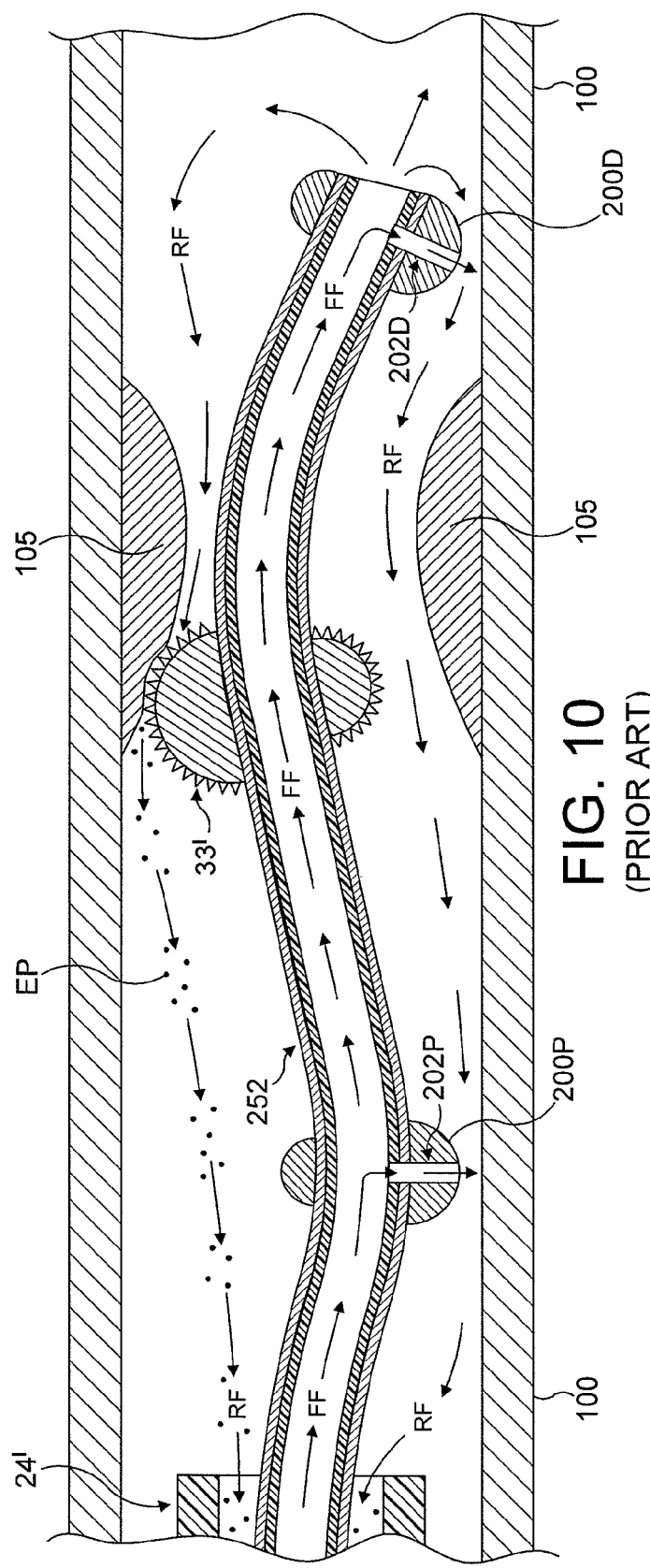
FIG. 10 is a side sectional view of a distal end portion of a tenth embodiment of the rotational atherectomy device of the prior art. The device of FIG. 10 is similar to the device of FIG. 6 except that the solid counterweights comprise channels which extend radially outward with respect to a rotational (longitudinal) axis of the drive shaft.
Figure 11:
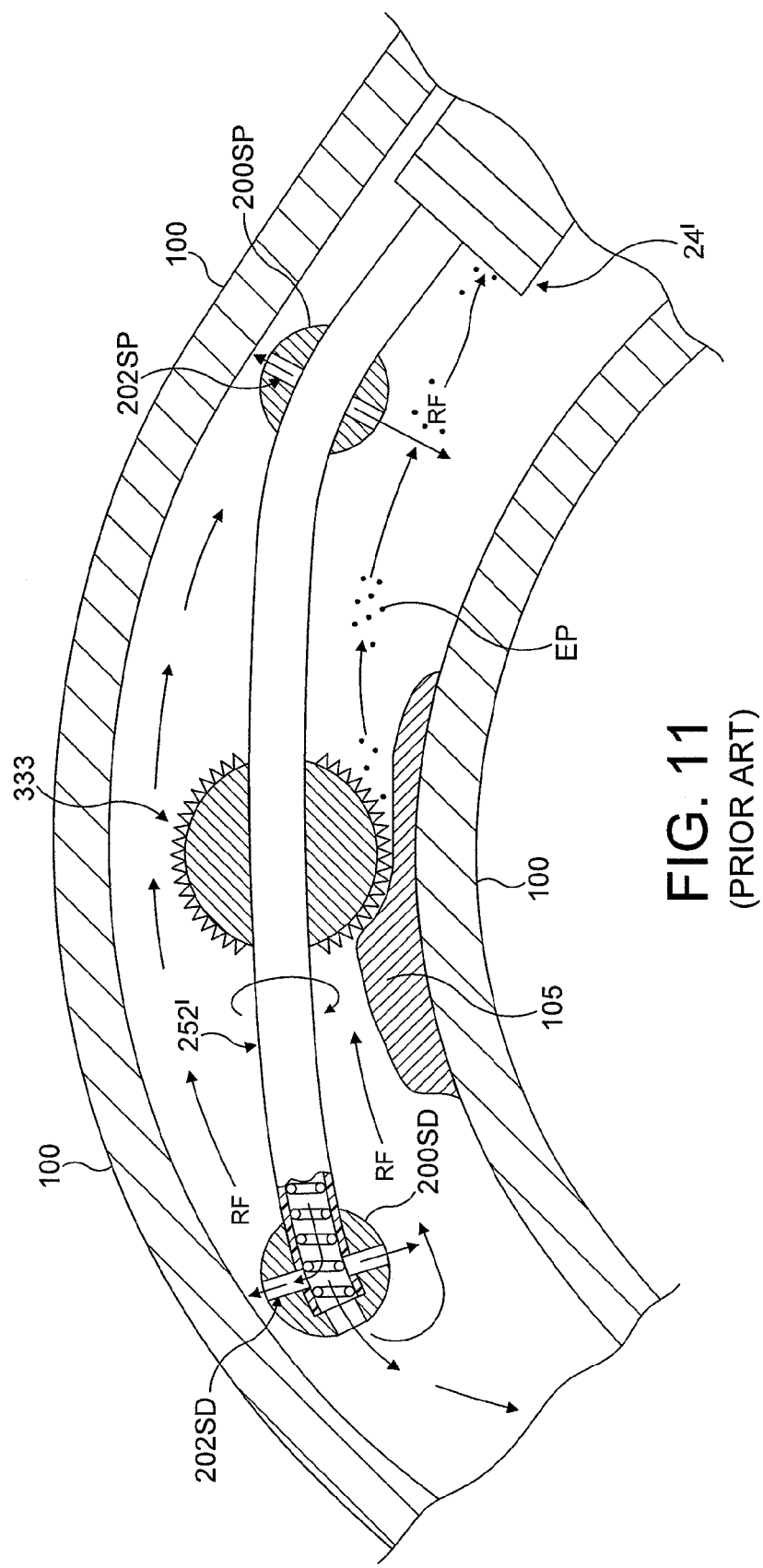
FIG. 11 is a side sectional view of a distal end portion of an eleventh embodiment of the rotational atherectomy device of the prior art. The device of FIG. 11 is similar to the device of FIG. 10 except that the abrasive element and the solid support elements are symmetric with respect to a rotational (longitudinal) axis of the drive shaft.
Figure 12:
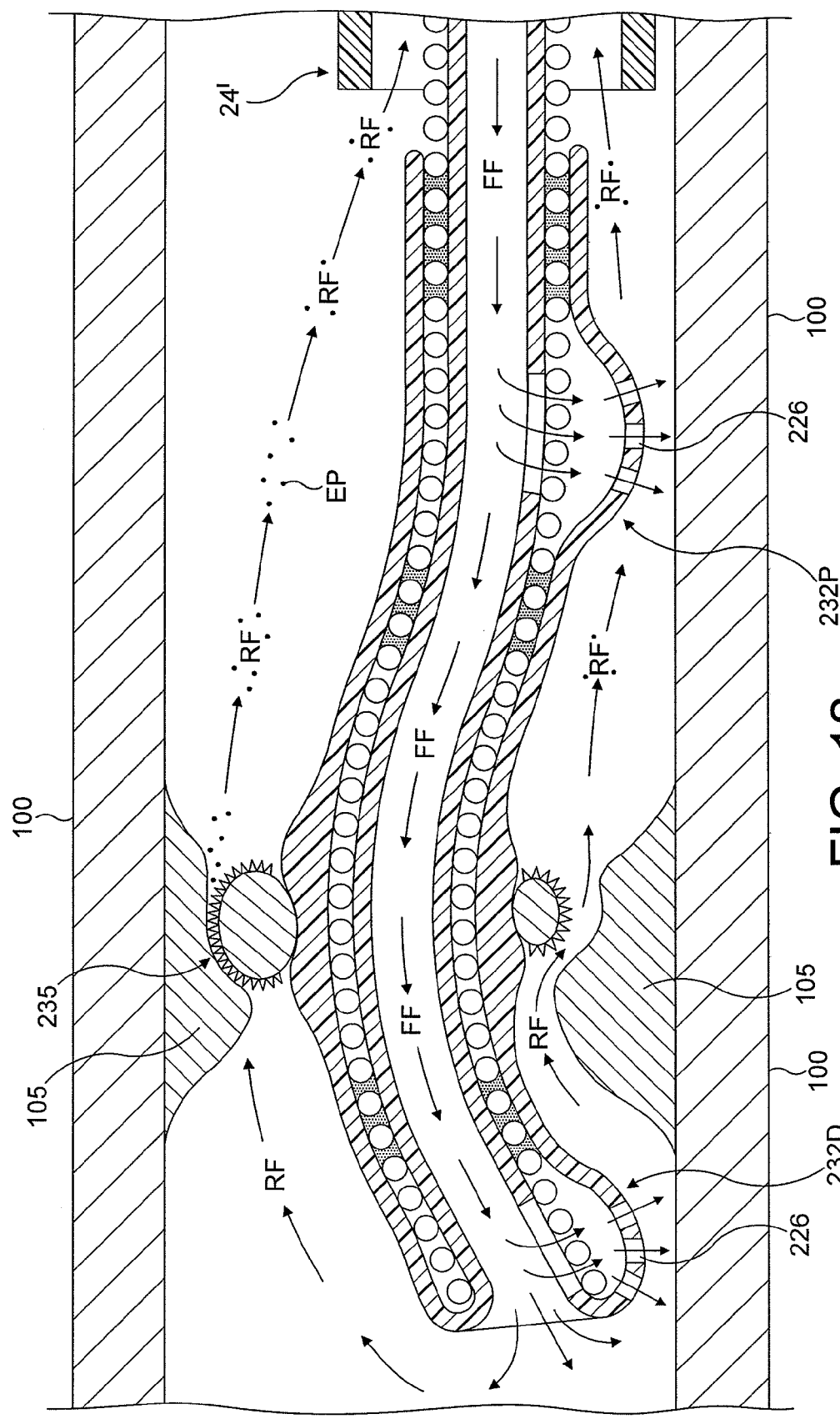
FIG. 12 is a side sectional view of a distal end portion of a twelfth embodiment of the rotational atherectomy device of the prior art. The device of FIG. 12 is similar to the device of FIG. 8 except that the fluid inflatable counterweights comprise outflow openings located such that pressurised fluid flowing through these openings forms fluid bearings between the fluid inflatable counterweights and a wall of the treated vessel.
Figure 13:
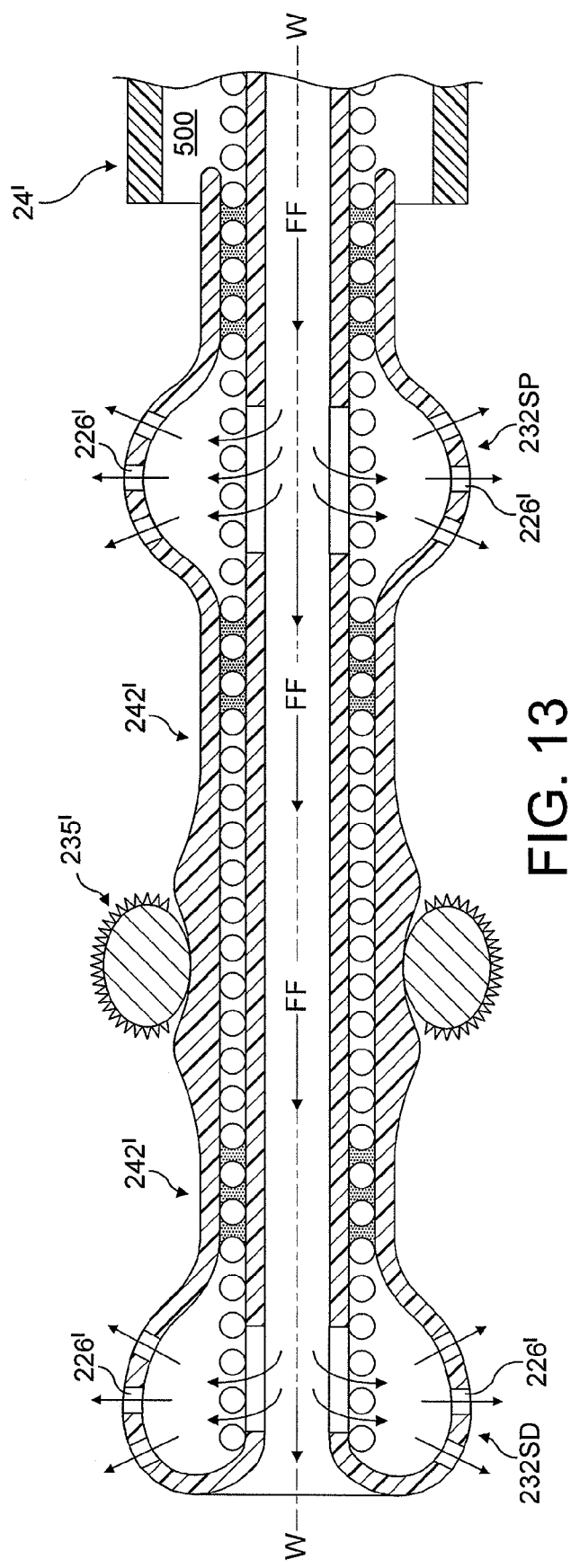
FIG. 13 is a side sectional view of a distal end portion of a thirteenth embodiment of the rotational atherectomy device of the prior art. The device of FIG. 13 is similar to the device of FIG. 12 except that the abrasive element and the fluid inflatable support elements are symmetric with respect to a rotational (longitudinal) axis of the drive shaft.
Figure 16A:
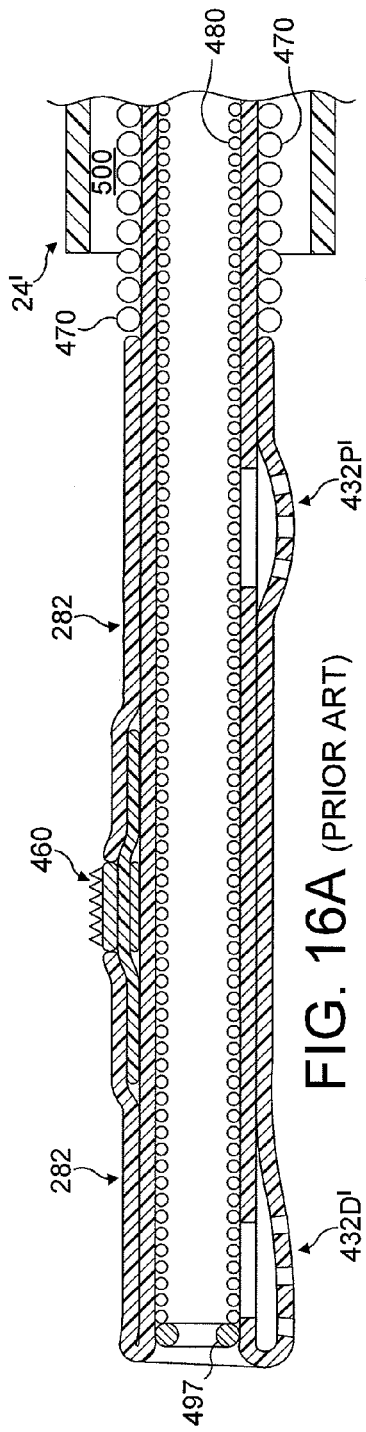
FIGS. 16A to 16C are side sectional views of distal end portions of a fifteenth embodiment of the rotational atherectomy device of the prior art. These figures illustrate formation of a ball valve at the distal end of the drive shaft.
Figure 16B:
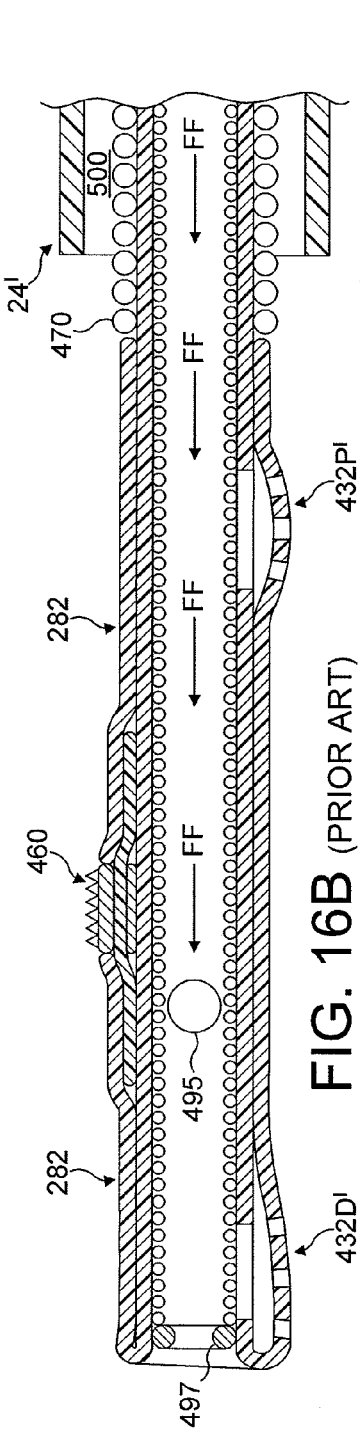
Figure 16C:
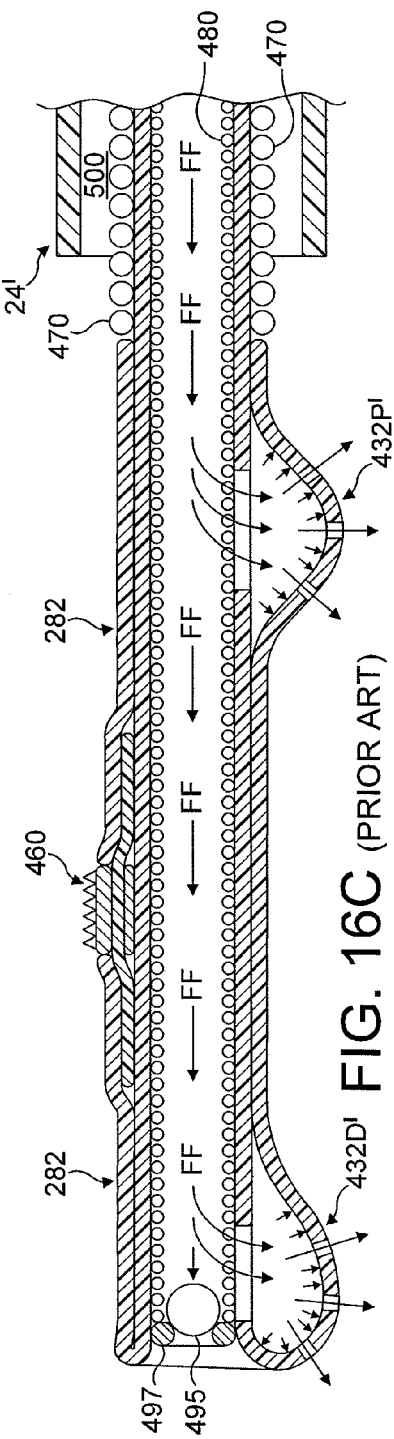

Reference is made in this specification to "distal" and "proximal" ends of the device. For the purpose of this specification, the distal end is considered to refer to the end of the device which is advanced into the vessel in the body of a patient and, the proximal end is the opposite end of the device which remains outside the body of the patient. The proximal end of the device is connected to fluid pumping and suction devices. The term "antegrade flow" refers to a direction of fluid flow from the proximal to the distal end of the device. Similarly, and the term "retrograde flow" refers to a direction of fluid flow in the opposite direction, i.e. from the distal to the proximal end of the device. The antegrade flowing fluid is indicated by arrows 'FF'. The retrograde flowing fluid is indicated by arrows 'RF'. Embolic particles are indicated by symbol 'EP'. Reference 'W-W' indicates a rotational (longitudinal) axis of the drive shaft.

FIG. 17 illustrates a first embodiment of a rotational atherectomy system with enhanced distal embolic protection capability of the present invention, the rotational atherectomy system comprising a rotational atherectomy device with counterweights and a separate drainage catheter, the retrograde flowing fluid being aspirated into the separate drainage catheter, both the rotational atherectomy device 777 and the drainage catheter 800 being shown inserted through separate openings located in the femoral arteries 900 of the patient and meeting in the aorta 966, the drainage catheter 800 extending into the common carotid artery 999 while the rotational atherectomy device 777 passes through the common carotid artery and extends further into the treated internal carotid artery 1500. FIG. 17 illustrates that the openings in the wall of the distal fluid inflatable counterweight of the device are located such that pressurized fluid flowing through the openings forms a fluid bearing between the wall of the fluid inflated distal counterweight and a wall of the treated vessel. FIG. 17 shows that an occlusion balloon 1116 is mounted to a catheter shaft 1115 of the drainage catheter 800. The occlusion balloon 1116 has been inflated in the common carotid artery 999 for temporarily engaging the atherectomy device 777 and the drainage catheter 800 with each other and for restricting flow of fluids towards and away from the treated stenotic lesion 666. FIG. 17 shows that the retrograde flowing fluid and embolic particles are aspirated into the drainage lumen of the drainage catheter 800.

It should be noted that it is preferable to provide the occlusion balloon on the drainage catheter rather than on the stationary sheath of the rotational atherectomy device because it results in a simpler design and operation of the atherectomy device.

FIG. 17A is a cross-sectional view of the drainage catheter 800 taken along the line A-A shown in FIG. 17. It shows drainage lumen 1120 and separate occlusion balloon inflation lumen 1119.

Figure 18A:
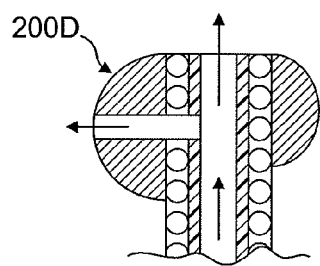
FIGS. 18A to 18D illustrate distal ends of four exemplary atherectomy devices of the prior art. Any one of these four rotational atherectomy devices having distal counterweights shown in FIGS. 18A, 18B, 18C and 18D (which correspond to the devices shown in FIGS. 10, 12, 15B and 16C respectively) may be used as a rotational atherectomy device of this first embodiment of the rotational atherectomy system with enhanced distal embolic protection.
Figure 18B:
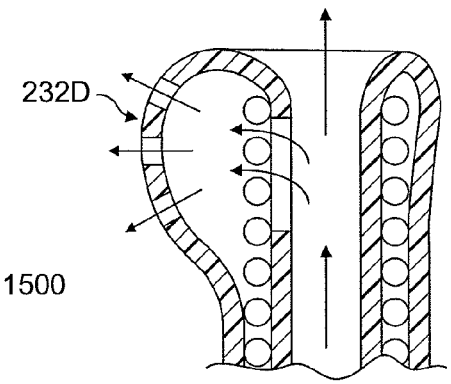
Figure 18:
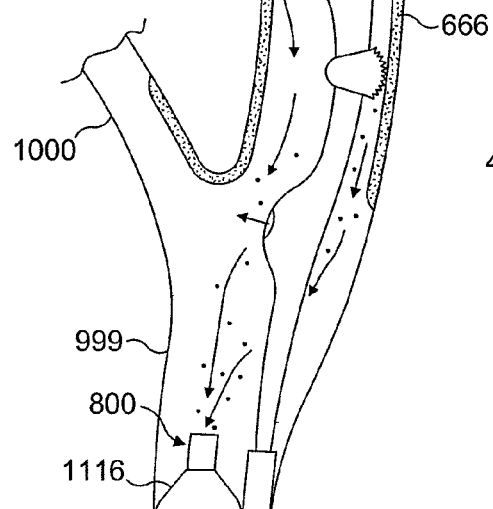
FIG. 18 is an enlarged view of the rotational atherectomy system shown in FIG. 17.
Figure 18C:
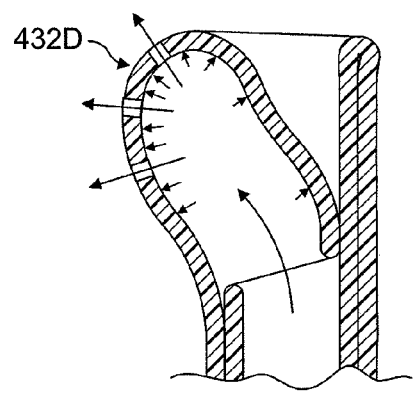
Figure 18D:
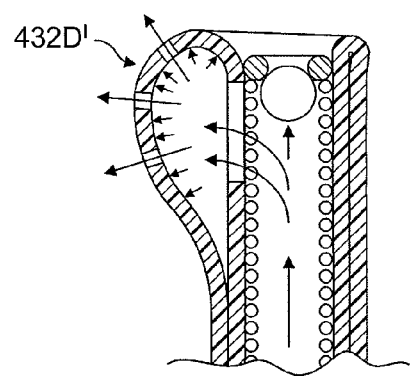

FIG. 18 is an enlarged view of the rotational atherectomy system shown in FIG. 17.

FIGS. 18A to 18D illustrate distal ends of four exemplary atherectomy devices of the prior art. Any one of these four rotational atherectomy devices having distal counterweights 200D, 232D, 432D and 432D', shown in FIGS. 18A, 18B, 18C and 18D and corresponding to the devices shown in FIGS. 10, 12, 15B and 16C respectively, may be used as a rotational atherectomy device 777 of this first embodiment of the rotational atherectomy system with enhanced distal embolic protection.

FIGS. 19A and 19B illustrate a preferred embodiment of the rotational atherectomy device with counterweights which may be used as a rotational atherectomy device of the rotational atherectomy system of the invention.

The rotational atherectomy device shown in FIGS. 19A and 19B differs from the prior art devices shown in FIGS. 1 to 16C in that it does not require a guidewire for advancement towards and across a stenotic lesion to be treated. FIGS. 19A and 19B show that the distal fluid inflatable counterweight 1300 is formed from a single fluid impermeable membrane 1900 which extends around an anchoring sleeve 1715 of the device. This fluid impermeable membrane crosses a longitudinal axis W-W of a long lumen 1600 of the device at the distal end of the device and prevents pressurized fluid flowing along the long lumen in an antegrade direction 'FF' from entering the treated vessel in the direction of said longitudinal axis W-W. FIG. 19B shows that the pressurized fluid has to pass through and inflate the distal fluid inflatable counterweight 1300, prior to exiting from the device through outflow openings 1666 in the distal fluid inflatable counterweight 1300 in a direction different from the direction of the longitudinal axis W-W of the long lumen 1600 of the device. FIGS. 19A and 19B show that the long lumen 1600 of the device, the lumen of the drive shaft 1601 of the device and a torque transmitting coil 1602 of the drive shaft 1601 have one common longitudinal axis W-W.

Figure 20:
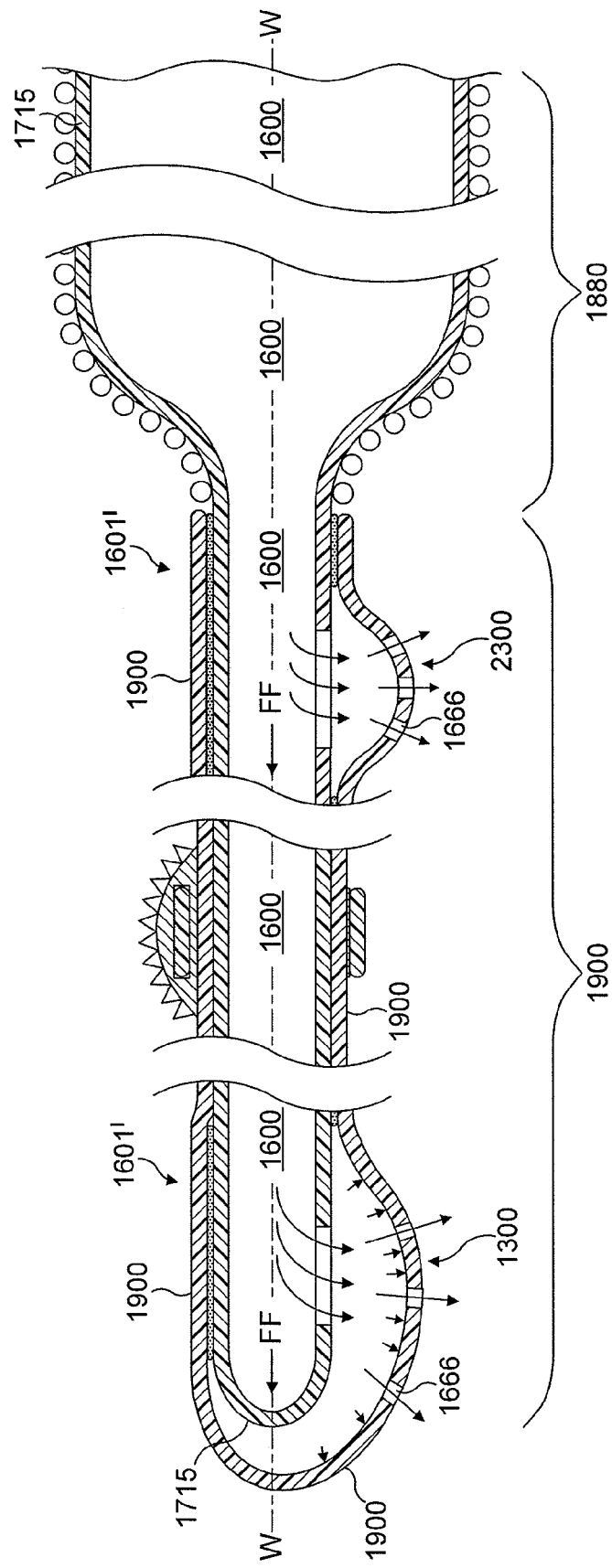
FIG. 20 illustrates a modification of the preferred embodiment of the rotational atherectomy device shown in FIGS. 19A and 19B. The device of FIG. 20 is similar to the device of FIG. 19B except that the lumen of the drive shaft has proximal and distal portions and the proximal portion of the lumen has a larger cross-sectional area relative to the cross-sectional area of the distal portion of the lumen. Thereby, per unit of length, the hydraulic resistance to fluid flow of the proximal portion of the lumen is less than the hydraulic resistance to fluid flow of the distal portion of the lumen.

FIG. 20 illustrates a modification of the preferred embodiment of the rotational atherectomy device shown in FIGS. 19A and 19B. The device of FIG. 20 is similar to the device of FIG. 19B except that the lumen 1600 of the drive shaft 1601' has proximal and distal portions and the proximal portion 1800 of the lumen has a larger cross-sectional area relative to the cross-sectional area of the distal portion 1900 of the lumen. Thereby, per unit of length, the hydraulic resistance to fluid flow of the proximal portion of the lumen is less than the hydraulic resistance to fluid flow of the distal portion of the lumen.

FIGS. 21A and 21B illustrate another modification of the preferred embodiment of the rotational atherectomy device with counterweights shown in FIGS. 19A and 19B. FIGS. 21A and 21B illustrate the rotational device with fluid inflatable counterweights which has been advanced across the stenotic lesion 2000 to a position in which the distal fluid inflatable counterweight 1300 has been located distal to the stenotic lesion 2000 and the proximal fluid inflatable counterweight 2300 has been intentionally located proximal to the stenotic lesion to be treated. The device of FIGS. 21A and 21B is similar to the device of FIGS. 19A and 19B, but differs in that it comprises an elongate core element 3000 disposed in the lumen of the drive shaft to stiffen the drive shaft and thereby assist in the advancement of the device along the vessel towards and across the stenotic lesion. The elongate core element comprises a long lumen, said lumen being in fluid communication with the lumen of the drive shaft through an opening located in a wall of the core element adjacent to its distal end. The continuous flow of the pressurized fluid from the lumen of the core element into the lumen of the drive shaft assists in removing the core element 3000 from the lumen 1600 of the drive shaft without changing position of the device in the treated vessel. Furthermore, the distal counterweight 1300, when inflated, may be anchored distal to the stenotic lesion 2000. Such inflating and anchoring of the distal counterweight against the stenotic lesion may help in removing the core element from the lumen of the drive shaft without changing position of the device in the treated vessel.

Figure 22A:
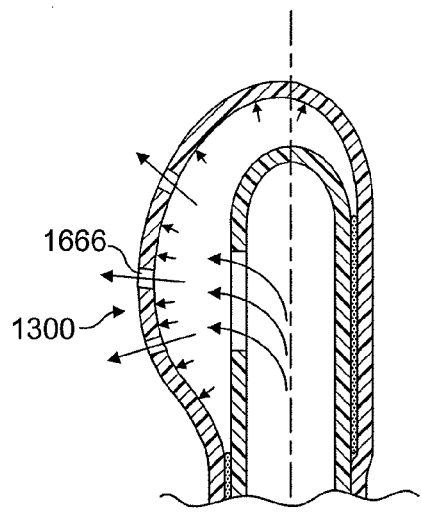
FIG. 22A illustrates a distal end of an exemplary atherectomy device with fluid inflatable counterweights which may be used as a rotational atherectomy device of the rotational atherectomy system of the invention shown in FIG. 22. Any one of the three rotational atherectomy devices shown in FIGS. 19A to 21B may be used as the rotational atherectomy device of this first embodiment of the rotational atherectomy system with enhanced distal embolic protection.
Figure 22:
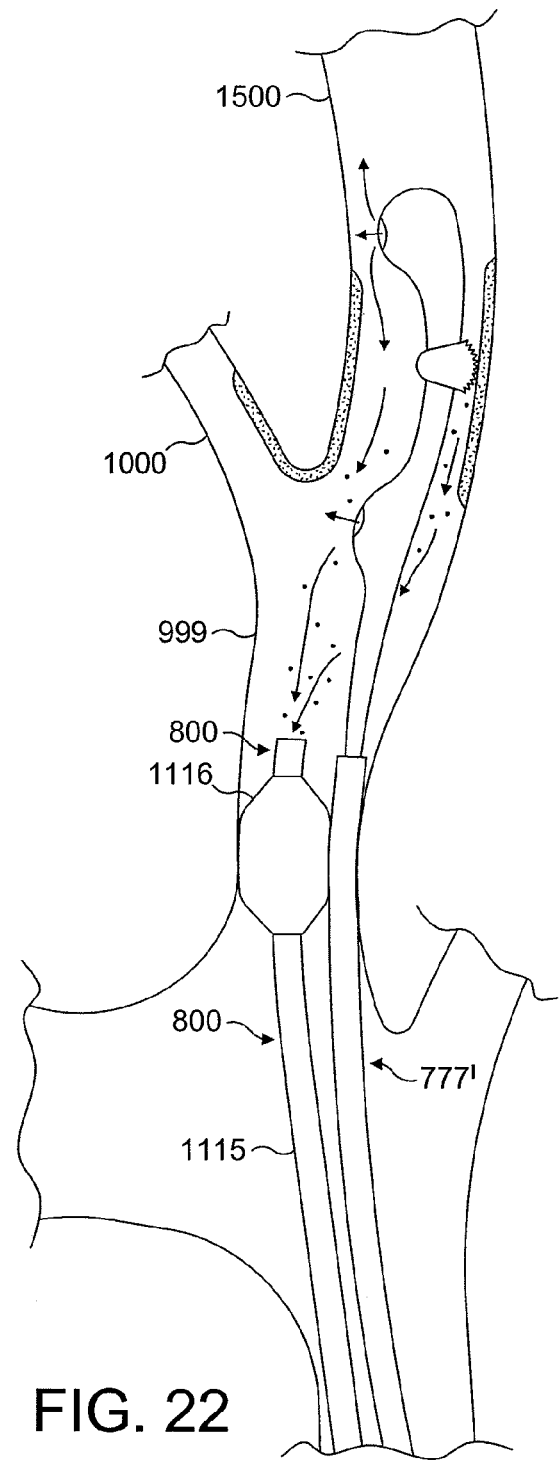
FIG. 22 illustrates a modification of the first embodiment of the rotational atherectomy system with enhanced distal embolic protection capability. The system of FIG. 22 is similar to the system of FIG. 18 except that the system of FIG. 22 comprises one of the rotational atherectomy devices shown in FIGS. 19A to 21B, i.e. the rotational atherectomy device in which a fluid impermeable wall of the distal fluid inflatable counterweight prevents pressurized fluid flowing along the lumen of the drive shaft from entering the treated vessel in the direction of the longitudinal axis of the drive shaft.

FIG. 22 illustrates a modification of the first embodiment of the rotational atherectomy system with enhanced distal embolic protection capability. The system of FIG. 22 is similar to the system of FIG. 18 except that the system of FIG. 22 comprises one of the rotational atherectomy devices shown in FIGS. 19A to 21B, i.e. the rotational atherectomy device in which a fluid impermeable wall of the distal fluid inflatable counterweight prevents pressurized fluid flowing along the lumen of the drive shaft from entering the treated vessel in the direction of the longitudinal axis of the drive shaft. FIG. 22 shows that pressurized fluid is exiting from the device 777' only through outflow openings in the distal and proximal fluid inflatable counterweights. FIG. 22 shows that the openings 1666 in the walls of the fluid inflatable counterweights are located such that pressurized fluid flowing through the openings form fluid bearings between the walls of the fluid inflated counterweights and a wall of the treated vessel.

FIG. 22A illustrates a distal end of an exemplary atherectomy device with fluid inflatable counterweights 1300 which may be used as a rotational atherectomy device 777' of the rotational atherectomy system of the invention shown in FIG. 22. Any one of the three rotational atherectomy devices shown in FIGS. 19A to 21B may be used as the rotational atherectomy device of this first embodiment of the rotational atherectomy system with enhanced distal embolic protection.

Figures 24, 24A, 24B, 24C:
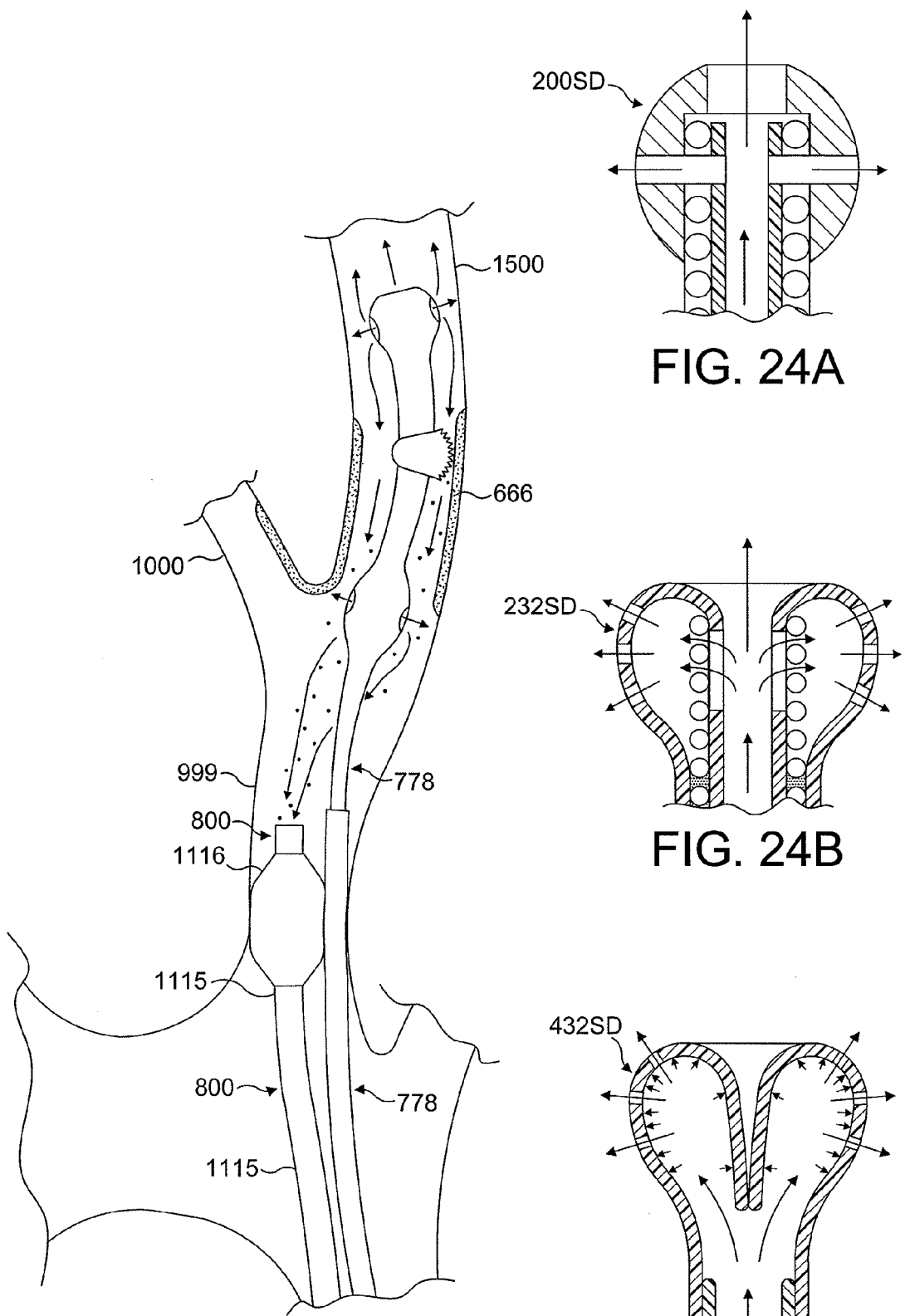
FIG. 24 is an enlarged view of the rotational atherectomy system shown in FIG. 23.
FIGS. 24A to 24C illustrate distal ends of exemplary atherectomy devices of the prior art which may be used as a rotational atherectomy device of the rotational atherectomy system of the invention shown in FIG. 24. Any one of the three rotational atherectomy devices having distal support elements shown in FIGS. 24A, 24B and 24C (which correspond to the devices shown in FIGS. 11, 13, and 14B respectively) may be used as a rotational atherectomy device of this second embodiment of the rotational atherectomy system with enhanced distal embolic protection.

FIG. 23 illustrates a second embodiment of the rotational atherectomy system with enhanced distal protection capability. The system of FIG. 23 is similar to the system of FIG. 17 except that the rotational atherectomy device 778 of FIG. 23, instead of counterweights, has support elements having centres of mass lying along the rotational (longitudinal) axis of the drive shaft of the device;

FIG. 23A is a cross-sectional view of the drainage catheter 800 taken along the line A-A shown in FIG. 23;

FIG. 24 is an enlarged view of the rotational atherectomy system shown in FIG. 23. FIG. 24 illustrates that the openings in the walls of the distal fluid inflatable support elements of the rotational atherectomy device are located such that pressurized fluid flowing through the openings form fluid bearings between the walls of the fluid inflated support elements and a wall of the treated vessel. FIG. 24 shows that an occlusion balloon 1116 is mounted to a catheter shaft 1115 of the drainage catheter. The occlusion balloon 1116 has been inflated in the common carotid artery 999 for temporarily engaging the atherectomy device 778 and the drainage catheter 800 with each other and for restricting flow of fluids towards and away from the treated stenotic lesion.

FIGS. 24A to 24C illustrate distal ends of exemplary atherectomy devices of the prior art which may be used as a rotational atherectomy device of the rotational atherectomy system of the invention shown in FIG. 24. Any one of the three rotational atherectomy devices having distal support elements 200SD, 232SD and 432SD shown in FIGS. 24A, 24B and 24C respectively (which correspond to the devices shown in FIGS. 11, 13 and 14B respectively), may be used as a rotational atherectomy device 778 of this second embodiment of the rotational atherectomy system with enhanced distal embolic protection.

FIGS. 25A and 25B illustrate a preferred embodiment of the rotational atherectomy device with fluid inflatable support elements which may be used as a rotational atherectomy device of the second embodiment of the rotational atherectomy system of the invention. The rotational atherectomy device shown in FIGS. 25A and 25B is similar to the rotational atherectomy device shown in FIGS. 19A and 19B, but differs in that the centres of mass of the inflatable support elements 1300S, 2300S are laying on the longitudinal axis W-W of the torque transmitting coil 1602 and of the lumen 1600 of the drive shaft 1601'. FIG. 25B shows the device of FIG. 25A after an antegrade flow FF of fluid has been initiated and the support elements have been inflated. FIG. 25B illustrates that fluid inflatable spaces 444, 446 within the support elements 1300S, 2300S extend uniformly around the longitudinal axis W-W of the torque transmitting coil 1602 and the lumen of the drive shaft 1601, therefore providing the fluid inflated support elements 1300S, 2300S with centres of mass which are laying on the longitudinal axis W-W of the torque transmitting coil 1602 and the lumen 1600 of the drive shaft 1601'.

Figure 26A:
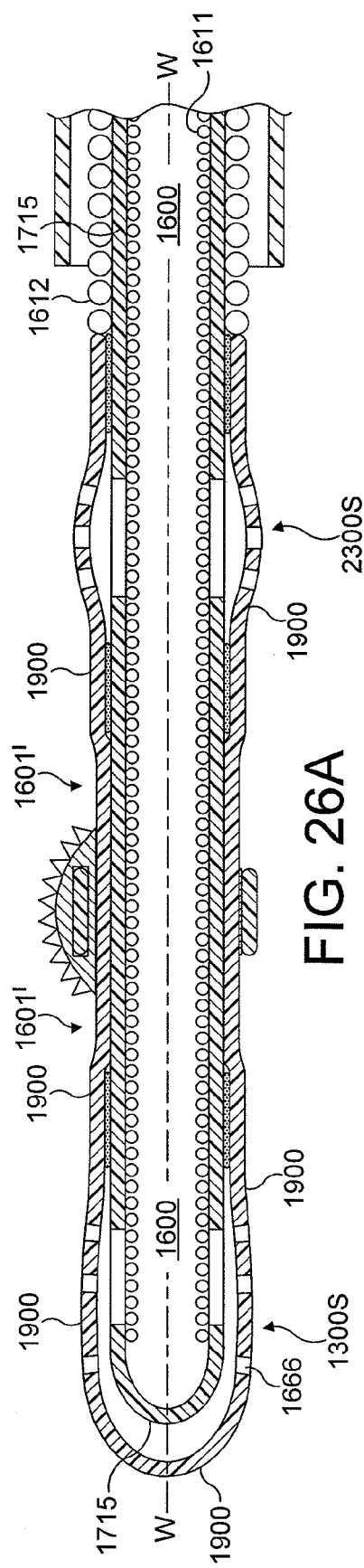
FIGS. 26A and 26B illustrate a modification of the preferred embodiment of the rotational atherectomy device shown in FIGS. 25A and 25B. The device shown in FIGS. 26A and 26B is similar to the rotational atherectomy device shown in FIGS. 19A and 19B, but differs in that the drive shaft comprises inner and outer torque transmitting coils.
Figure 26B:
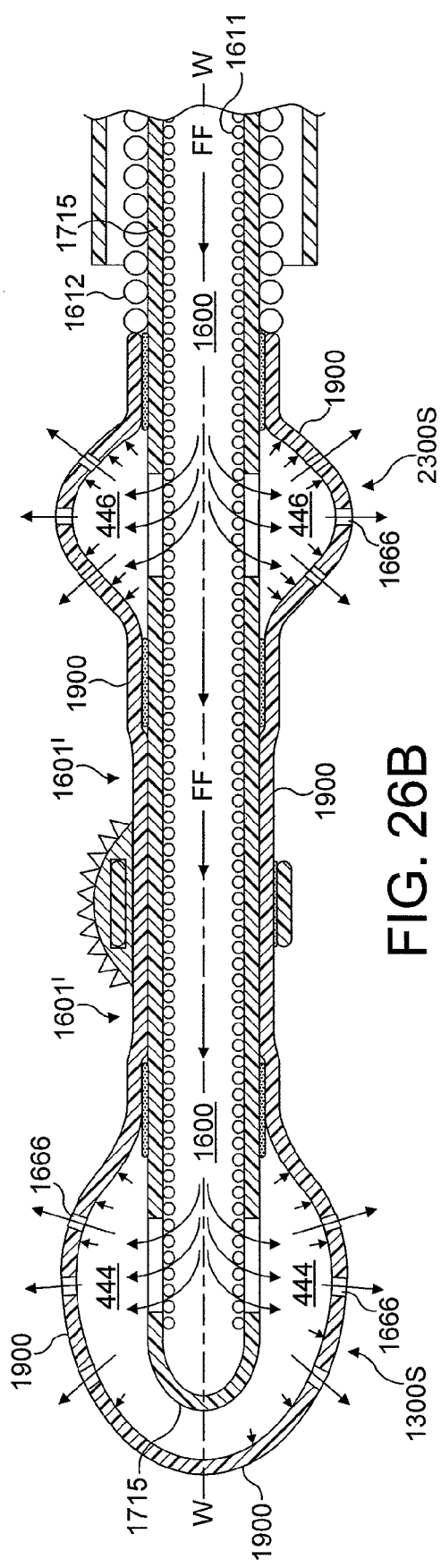

FIGS. 26A and 26B illustrate a modification of the preferred embodiment of the rotational atherectomy device shown in FIGS. 25A and 25B. The device shown in FIGS. 26A and 26B is similar to the rotational atherectomy device shown in FIGS. 19A and 19B, but differs in that the drive shaft 1601' comprises inner and outer torque transmitting coils 1611, 1612.

Figure 27A:
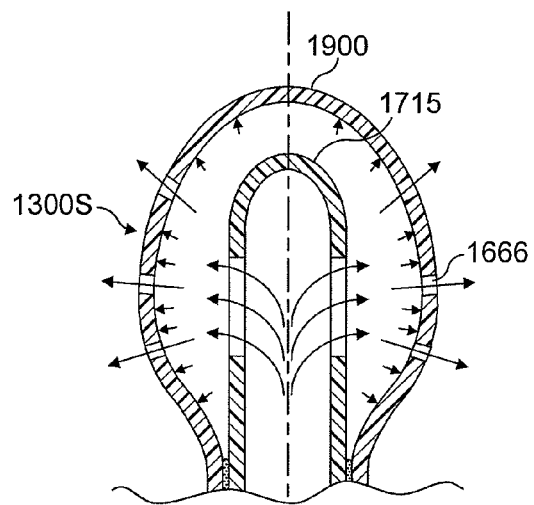
FIGS. 27A and 27B illustrate distal ends of exemplary atherectomy devices with fluid inflatable support elements shown in FIGS. 25A to 26B. Any one of the two rotational atherectomy devices shown in FIGS. 25A to 26B may be used as a rotational atherectomy device of this modification of the second embodiment of the rotational atherectomy system shown in FIG. 27.
Figure 27B:
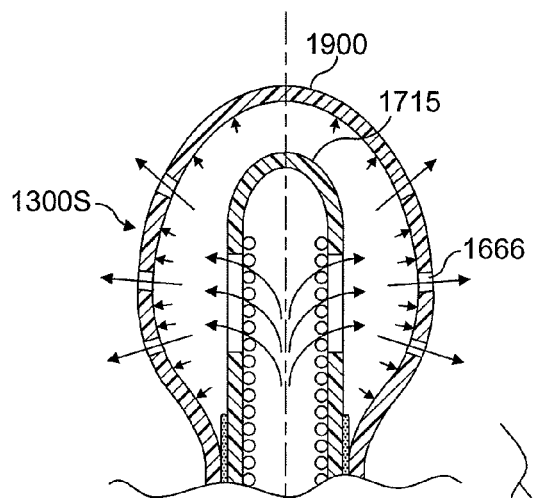
Figure 27:
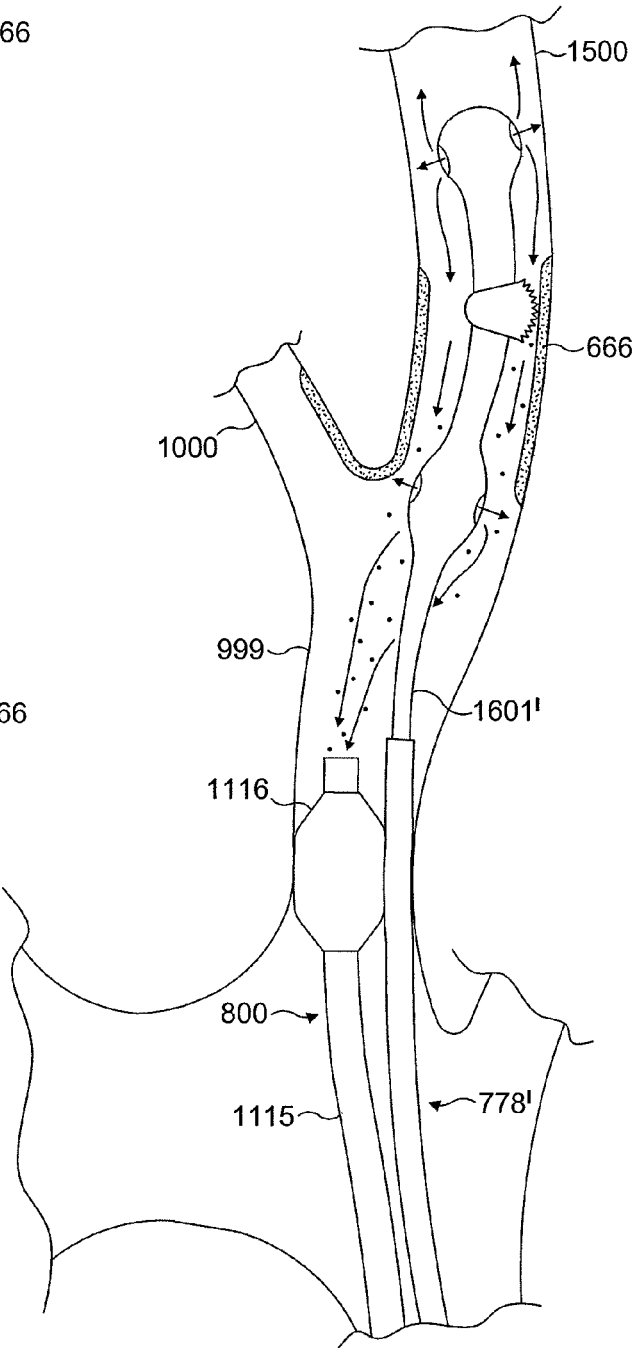
FIG. 27 illustrates a modification of the second embodiment of the rotational atherectomy system with enhanced distal embolic protection capability. The system of FIG. 27 is similar to the system of FIG. 24 except that the system of FIG. 27 comprises one of the rotational atherectomy devices shown in FIGS. 25A to 26B, i.e. the rotational atherectomy device in which a fluid impermeable wall of the distal fluid inflatable support element prevents pressurized fluid flowing along the lumen of the drive shaft from entering the treated vessel in the direction of the longitudinal axis of the drive shaft.

FIG. 27 illustrates a modification of the second embodiment of the rotational atherectomy system with enhanced distal embolic protection capability. The system of FIG. 27 is similar to the system of FIG. 24 except that the system of FIG. 27 comprises one of the rotational atherectomy devices shown in FIGS. 25A to 26B, i.e. the rotational atherectomy device in which a fluid impermeable wall 1900 of the distal fluid inflatable support element 1300S prevents pressurized fluid flowing along the lumen of the drive shaft from entering the treated vessel in the direction of the longitudinal axis of the drive shaft 1601'. FIG. 27 shows that pressurized fluid is exiting from the device only through outflow openings in the distal and proximal fluid inflatable support elements 1300S, 2300. FIG. 27 shows that the openings in the walls of the distal and proximal fluid inflatable support elements are located such that pressurized fluid flowing through the openings forms a fluid bearing between the walls of the fluid inflated distal and proximal support elements and a wall of the treated vessel. FIG. 27 shows that an occlusion balloon 1116 is mounted to a catheter shaft 1115 of the drainage catheter 800. The occlusion balloon has been inflated in the common carotid artery for temporarily engaging the atherectomy device and the drainage catheter with each other and for restricting flow of fluids towards and away from the treated stenotic lesion. FIG. 27 shows that the retrograde flowing fluid and embolic particles are aspirated into the drainage lumen of the drainage catheter 800.

FIGS. 27A and 27B illustrate distal ends of exemplary atherectomy devices with fluid inflatable support elements shown in FIGS. 25A to 26B respectively. Any one of the two rotational atherectomy devices shown in FIGS. 25A to 26B may be used as a rotational atherectomy device 778' of this modification of the second embodiment of the rotational atherectomy system shown in FIG. 27.

Figure 28:
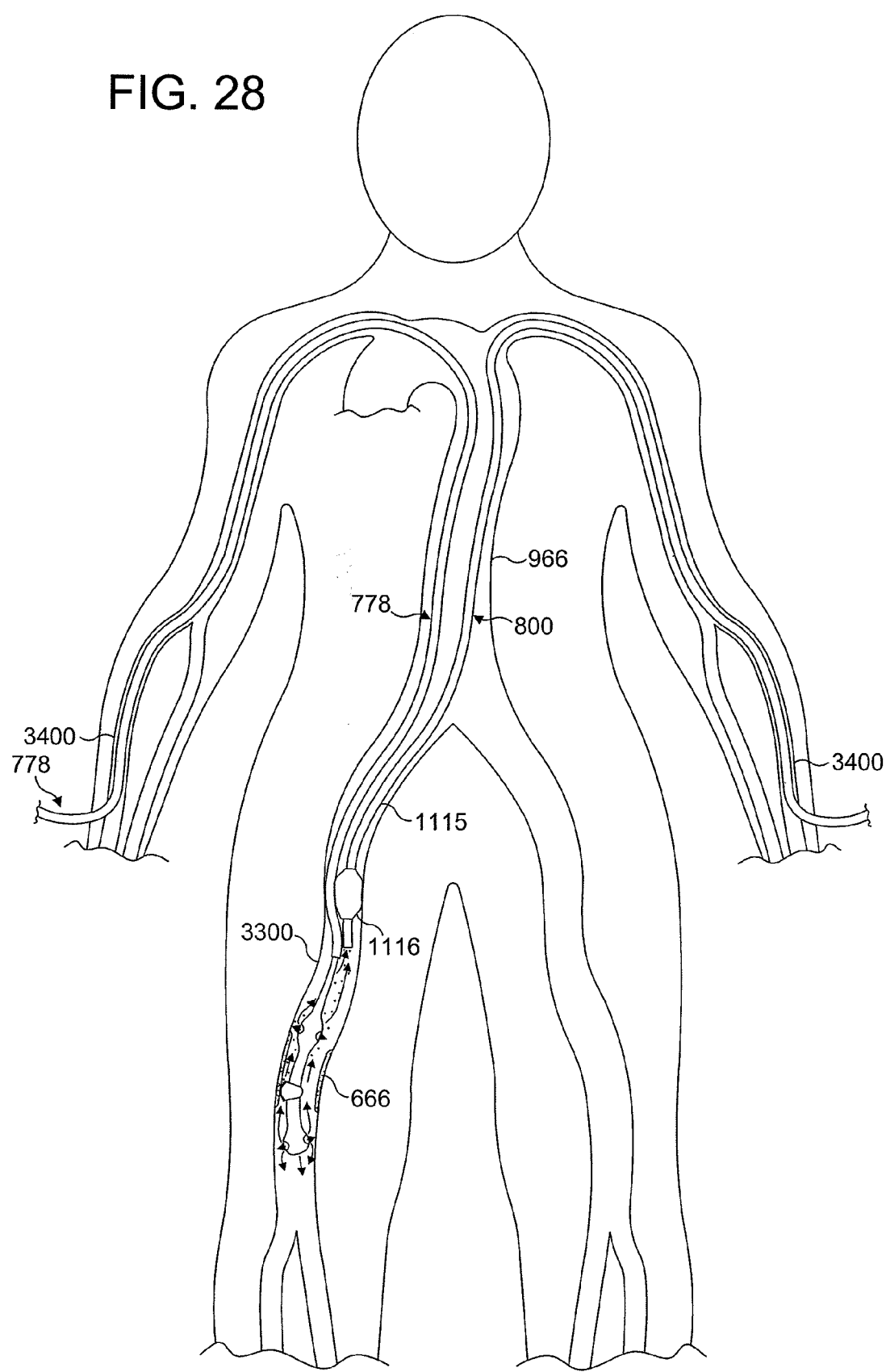
FIG. 28 illustrates how the second embodiment of the rotational atherectomy system of the invention may be used for treatment of the stenotic lesion located in the superficial femoral artery.

FIG. 28 illustrates how the second embodiment of the rotational atherectomy system of the invention may be used for treatment of the stenotic lesion located in the superficial femoral artery 3300. FIG. 28 shows that the rotational atherectomy device 778 and the drainage catheter 800 have been introduced into the patient's vasculature through separate openings located in the radial arteries 3400 of the patient. The atherectomy device and the drainage catheter are meeting in the aorta 966 and extending into the treated femoral artery 3300 of a patient. FIG. 28 shows that an occlusion balloon 1116 is mounted to a catheter shaft 1115 of the drainage catheter 800. The occlusion balloon has been inflated in the femoral artery proximal to the treated stenotic lesion for temporarily engaging the atherectomy device and the drainage catheter with each other and for restricting flow of fluids towards and away from the treated stenotic lesion 666. The retrograde flowing fluid and embolic particles are aspirated into the drainage lumen of the drainage catheter 800.

Figure 29:
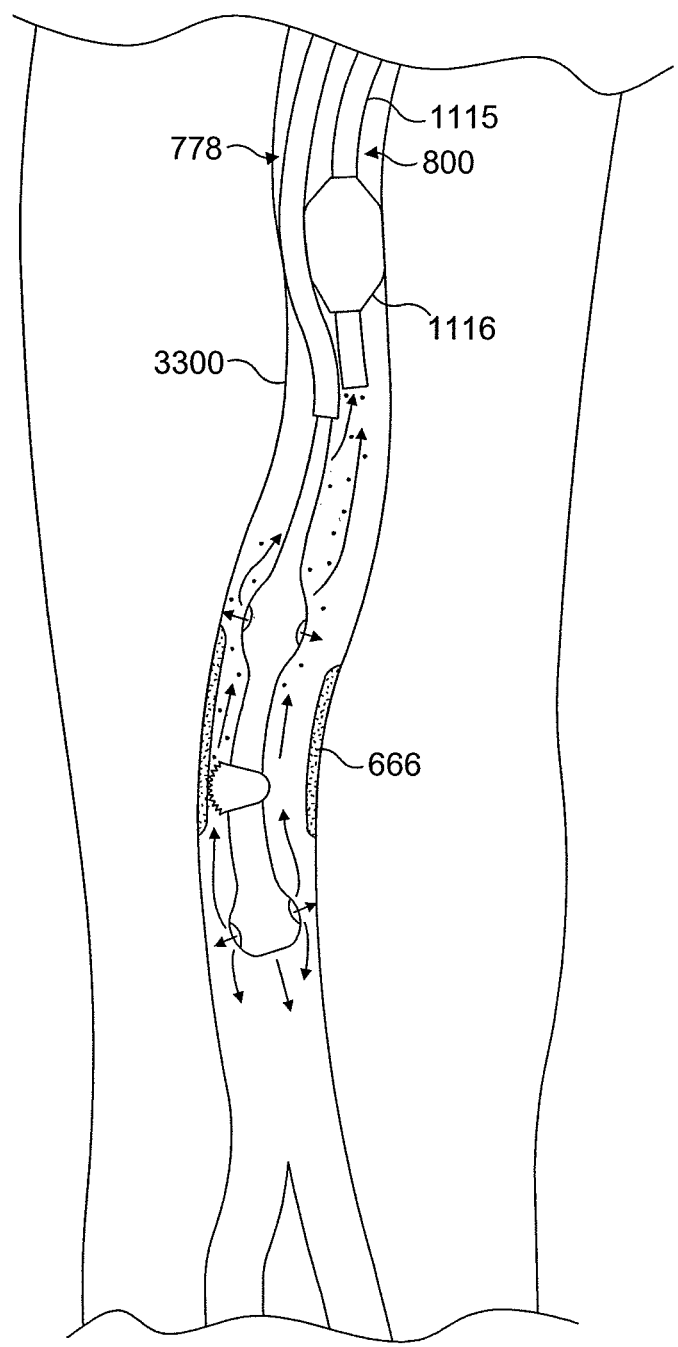
FIG. 29 is an enlarged view of the rotational atherectomy system shown in FIG. 28.
Figure 30A:
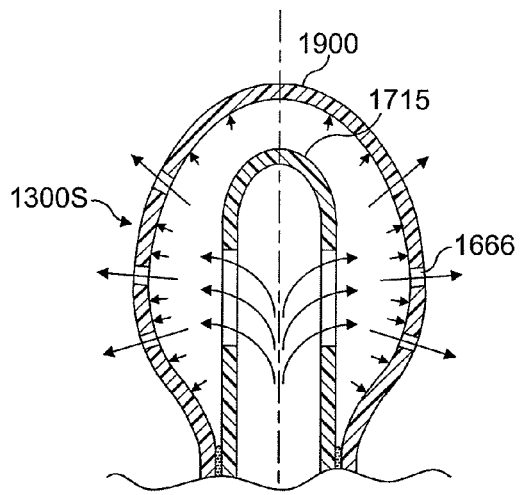
FIGS. 30A and 30B illustrate distal ends of exemplary atherectomy devices with fluid inflatable support elements shown in FIGS. 25A to 26B. Any one of the two rotational atherectomy devices shown in FIGS. 25A to 26B may be used as a rotational atherectomy device of this modification of the second embodiment of the rotational atherectomy system shown in FIG. 30.
Figure 30B:
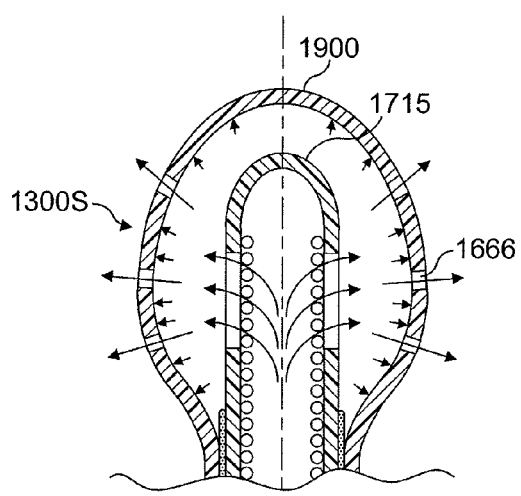
Figure 30:
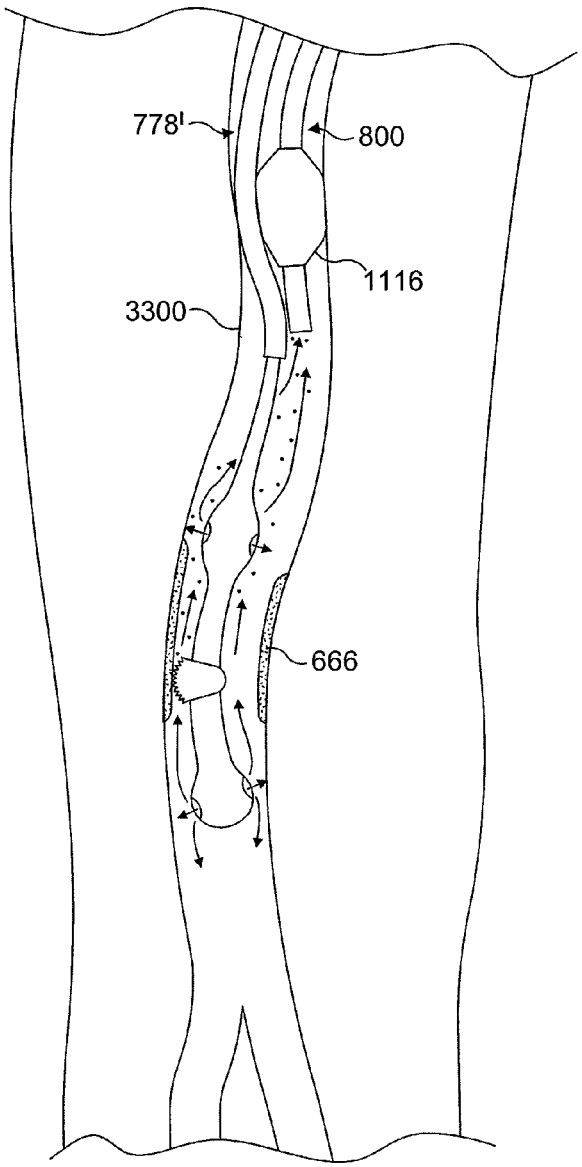
FIG. 30 is similar to FIG. 29 except that it shows the modified rotational atherectomy system of the second embodiment. The system of FIG. 30 is similar to the system of FIG. 29 except that the system of FIG. 30 comprises one of the rotational atherectomy devices shown in FIGS. 25A to 26B, i.e. the rotational atherectomy device in which a fluid impermeable wall of the distal fluid inflatable support element prevents pressurized fluid flowing along the lumen of the drive shaft from entering the treated vessel in the direction of the longitudinal axis of the drive shaft.

FIG. 29 is an enlarged view of the rotational atherectomy system shown in FIG. 28;

FIG. 30 is similar to FIG. 29 except that it shows the modified rotational atherectomy system of the second embodiment. The system of FIG. 30 is similar to the system of FIG. 29 except that the system of FIG. 30 comprises one of the rotational atherectomy devices shown in FIGS. 25A to 26B, i.e. the rotational atherectomy device 778' in which a fluid impermeable wall of the distal fluid inflatable support element prevents pressurized fluid flowing along the lumen of the drive shaft from entering the treated vessel in the direction of the longitudinal axis of the drive shaft.

FIGS. 30A and 30B illustrate distal ends of exemplary atherectomy devices with fluid inflatable support elements shown in FIGS. 25A to 26B. Any one of the two rotational atherectomy devices shown in FIGS. 25A to 26B may be used as a rotational atherectomy device 778' of this modification of the second embodiment of the rotational atherectomy system shown in FIG. 30.

Figure 31:
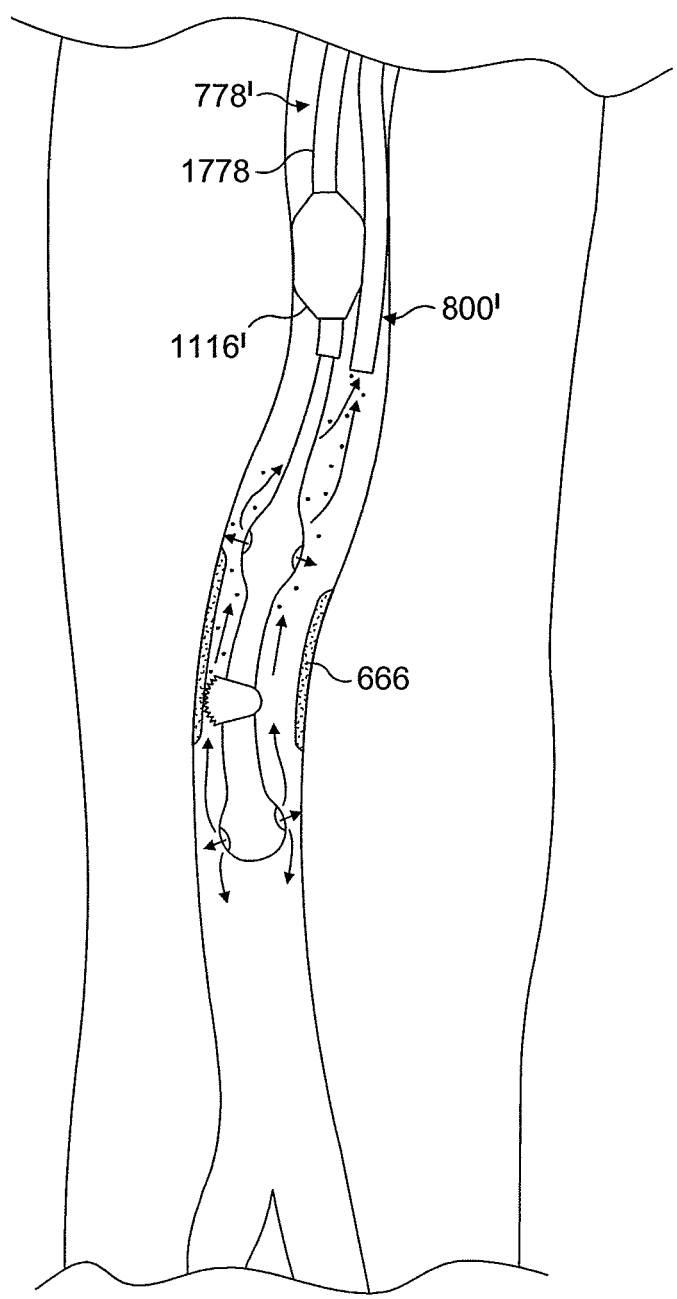
FIG. 31 is similar to FIG. 29, but differs in that the occlusion balloon is mounted to a drive shaft sheath of the rotational atherectomy device instead of being mounted to the catheter shaft of the drainage catheter.

FIG. 31 is similar to FIG. 30, but differs in that the occlusion balloon is mounted to a drive shaft sheath 1778 of the rotational atherectomy device 778' instead of being mounted to the catheter shaft of the drainage catheter 800'.

Figure 32:
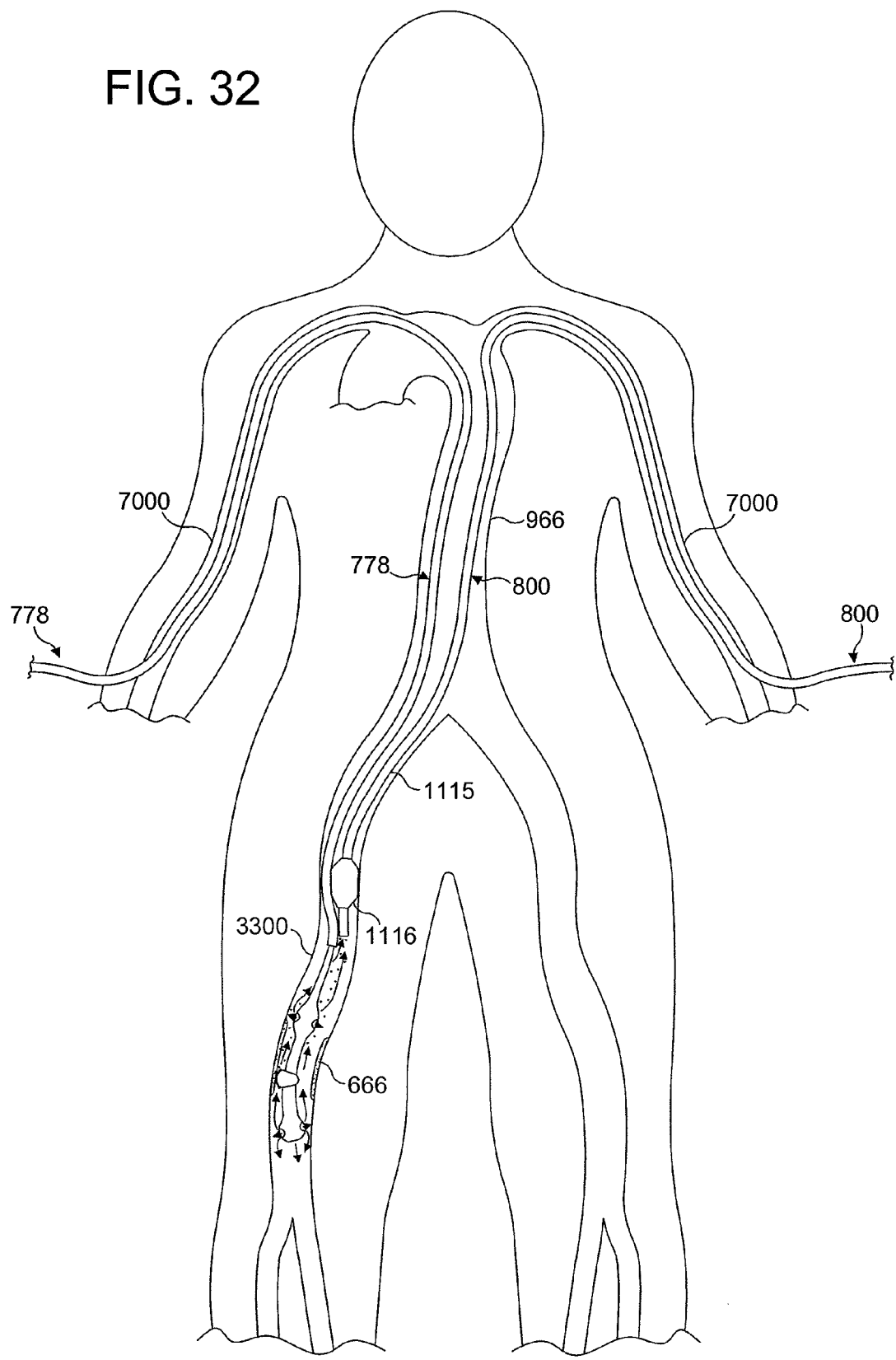
FIG. 32 is similar to FIG. 28, but differs in that both the rotational atherectomy device and the drainage catheter have been introduced into the patient's vasculature through separate openings located in the brachial arteries of the patient.

FIG. 32 is similar to FIG. 28, but differs in that both the rotational atherectomy device 778 and the drainage catheter 800 have been introduced into the patient's vasculature through separate openings located in the brachial arteries 7000 of the patient.

Figure 33:
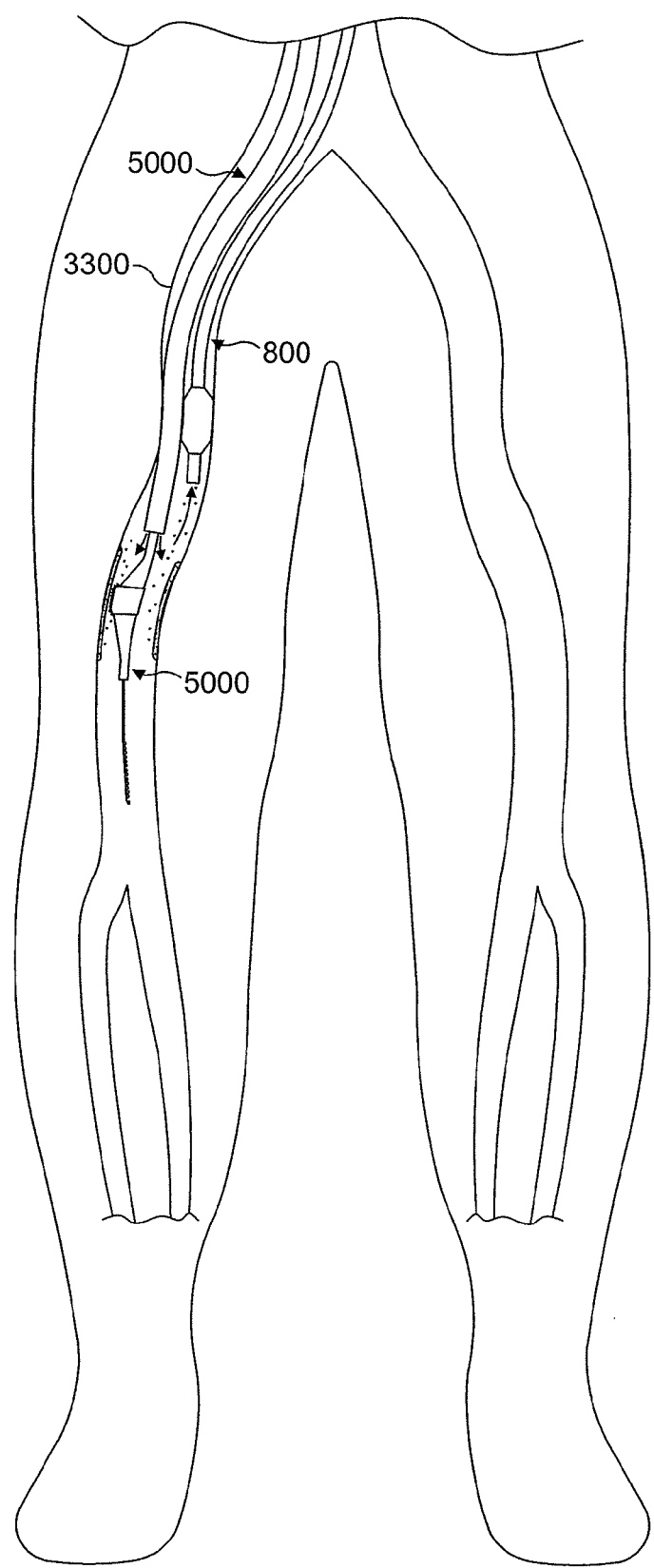
FIG. 33 illustrates a third embodiment of the rotational atherectomy system with enhanced distal embolic protection capability. The system of FIG. 33 is similar to the systems of the first and second embodiments in that it includes both a separate rotational atherectomy device and a separate drainage catheter. The rotational atherectomy system of the third embodiment differs from the systems of the first and second embodiments in that it includes a rotational atherectomy device without support elements or counterweights.

FIG. 33 illustrates a third embodiment of the rotational atherectomy system with enhanced distal embolic protection capability. The system of FIG. 33 is similar to the systems of the first and second embodiments in that it includes both a separate rotational atherectomy device and a separate drainage catheter. The rotational atherectomy system of the third embodiment differs from the systems of the first and second embodiments in that it includes a rotational atherectomy device without support elements or counterweights. FIG. 33 shows that the rotational atherectomy system of the third embodiment includes an orbital atherectomy device 5000 of the prior art shown in FIG. 3 but it should be understood that it may instead include a classic rotational atherectomy device of the prior art shown in FIG. 1.

Figure 34:
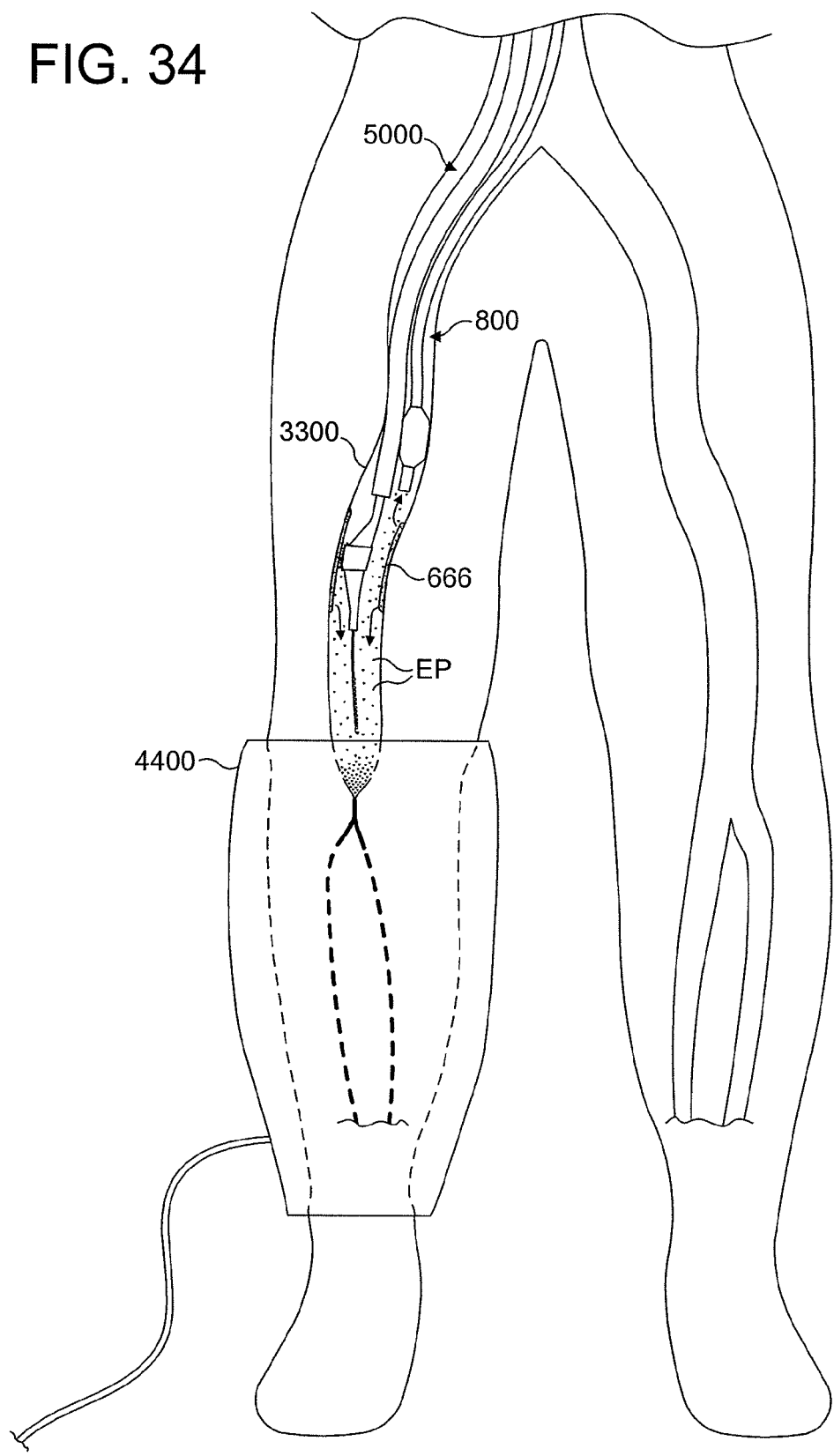
FIG. 34 illustrates a fourth embodiment of the rotational atherectomy system with enhanced distal protection capability. The system of FIG. 34 is similar to the system of FIG. 33 except that it includes an external occlusion cuff.

FIG. 34 illustrates a fourth embodiment of the rotational atherectomy system with enhanced distal protection capability. The system of FIG. 34 is similar to the system of FIG. 33 except that it includes an external occlusion cuff 4400. FIG. 34 shows that tibial arteries and the most distal segment of the popliteal artery have been occluded by an inflated external occlusion cuff 4400. FIG. 34 illustrates any embolic particles EP abraded by the atherectomy device and not immediately evacuated through the drainage catheter 800 accumulate distal to the site of the treated stenotic area but proximal to a point at which the inflated occlusion cuff has compressed the treated vessel or its distal branches.

Figure 35:
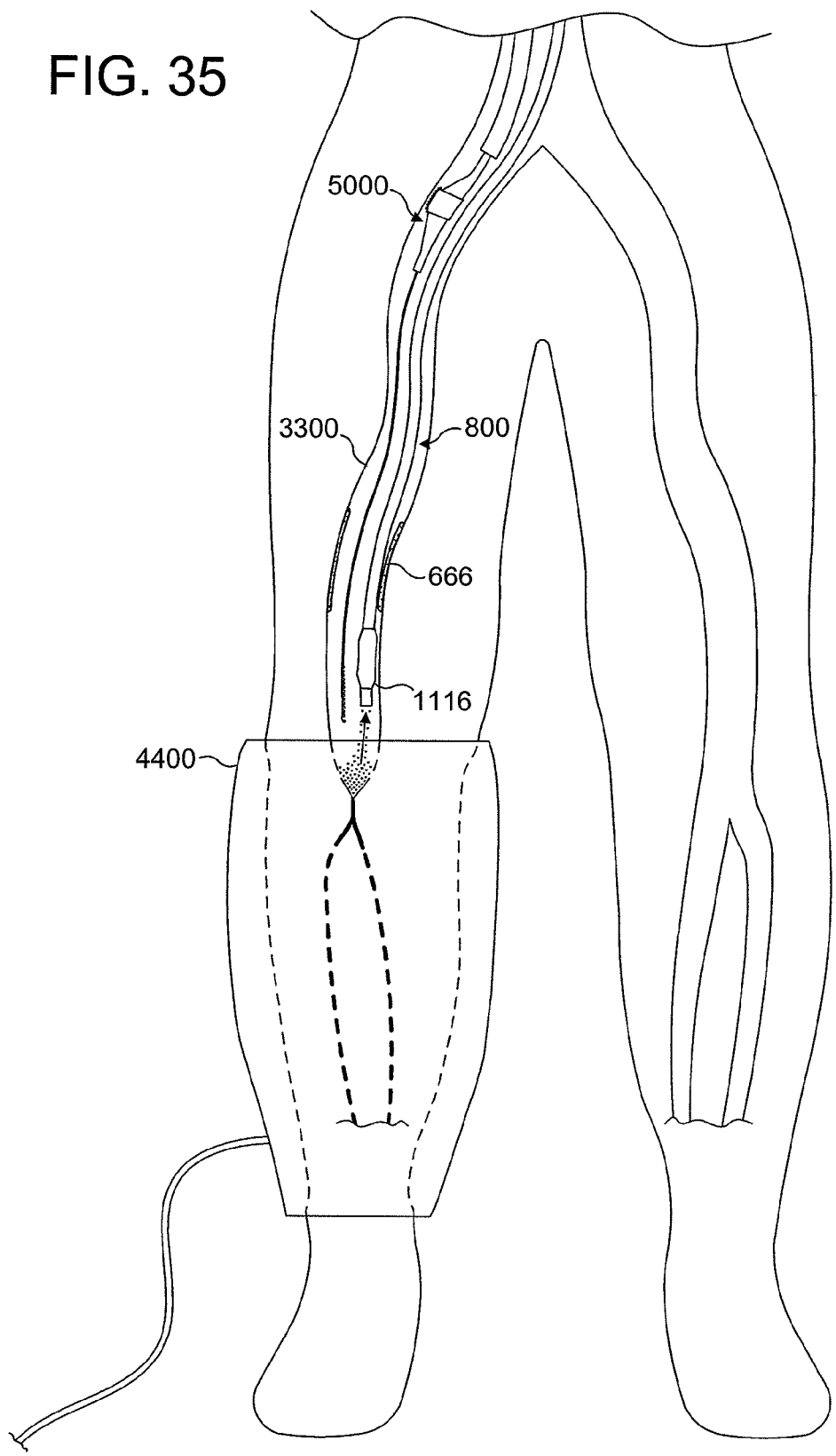
FIG. 35 is similar to FIG. 34, but shows that the occlusion balloon of the drainage catheter has been deflated and the drainage catheter has subsequently been advanced sufficiently close to the accumulated embolic particles.

FIG. 35 shows that the occlusion balloon 1116 of the drainage catheter 800 shown in FIG. 34, has been deflated and the drainage catheter 800 has subsequently been advanced sufficiently close to the embolic particles EP accumulated proximal to the segment of the artery occluded by the external occlusion cuff 4400. FIG. 35 also shows that the rotational atherectomy device 5000 has been withdrawn proximally away from the stenotic lesion 666 to afford movement of the drainage catheter 800 closer to the accumulated embolic particles.

Figure 36:
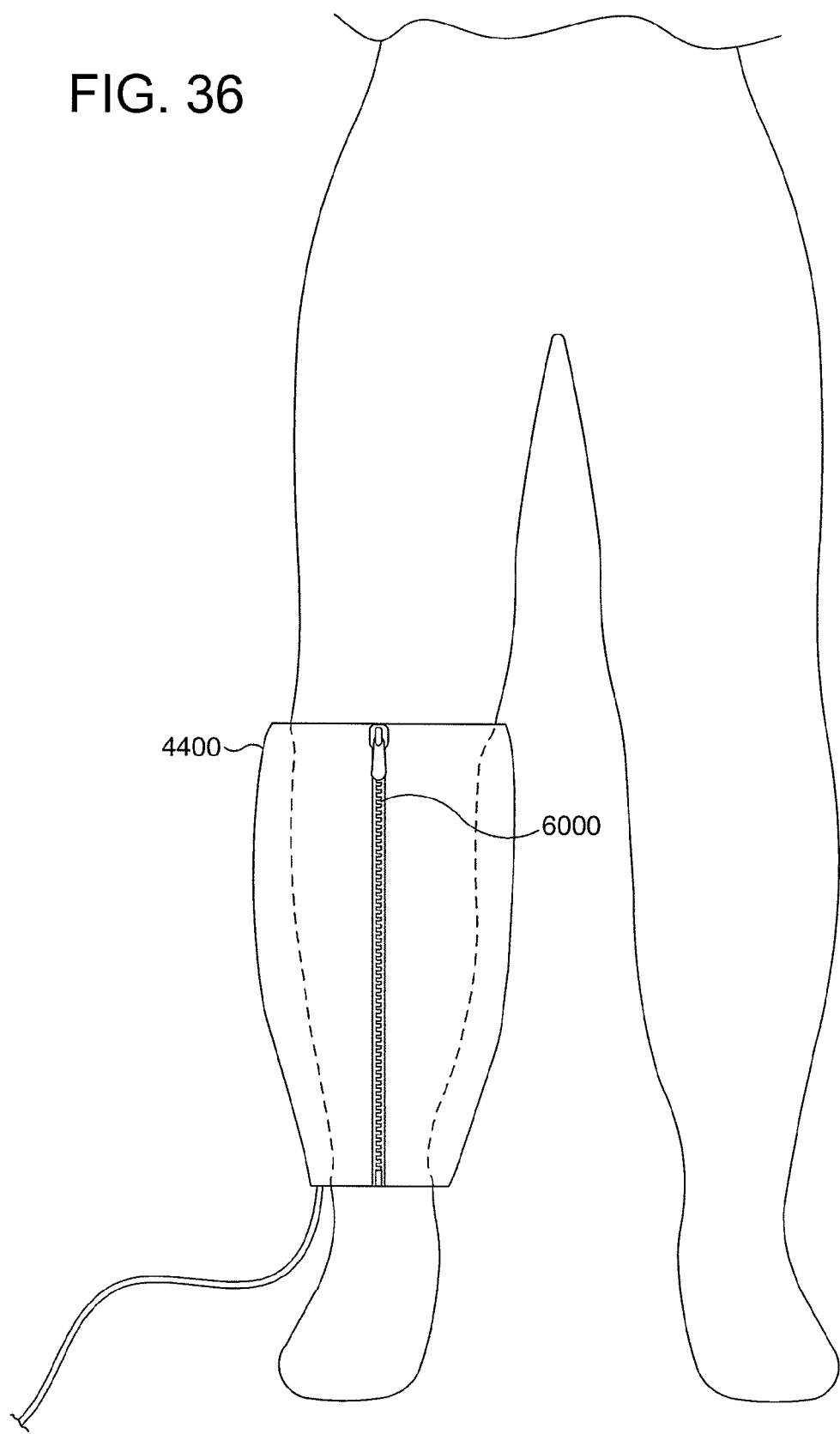
FIG. 36 illustrates an inflated external occlusion cuff for occluding the tibial and the most distal segment of the popliteal artery, the cuff comprising a zip fastener for closing the inflatable cuff in position around the patient's calf.
Figure 37:
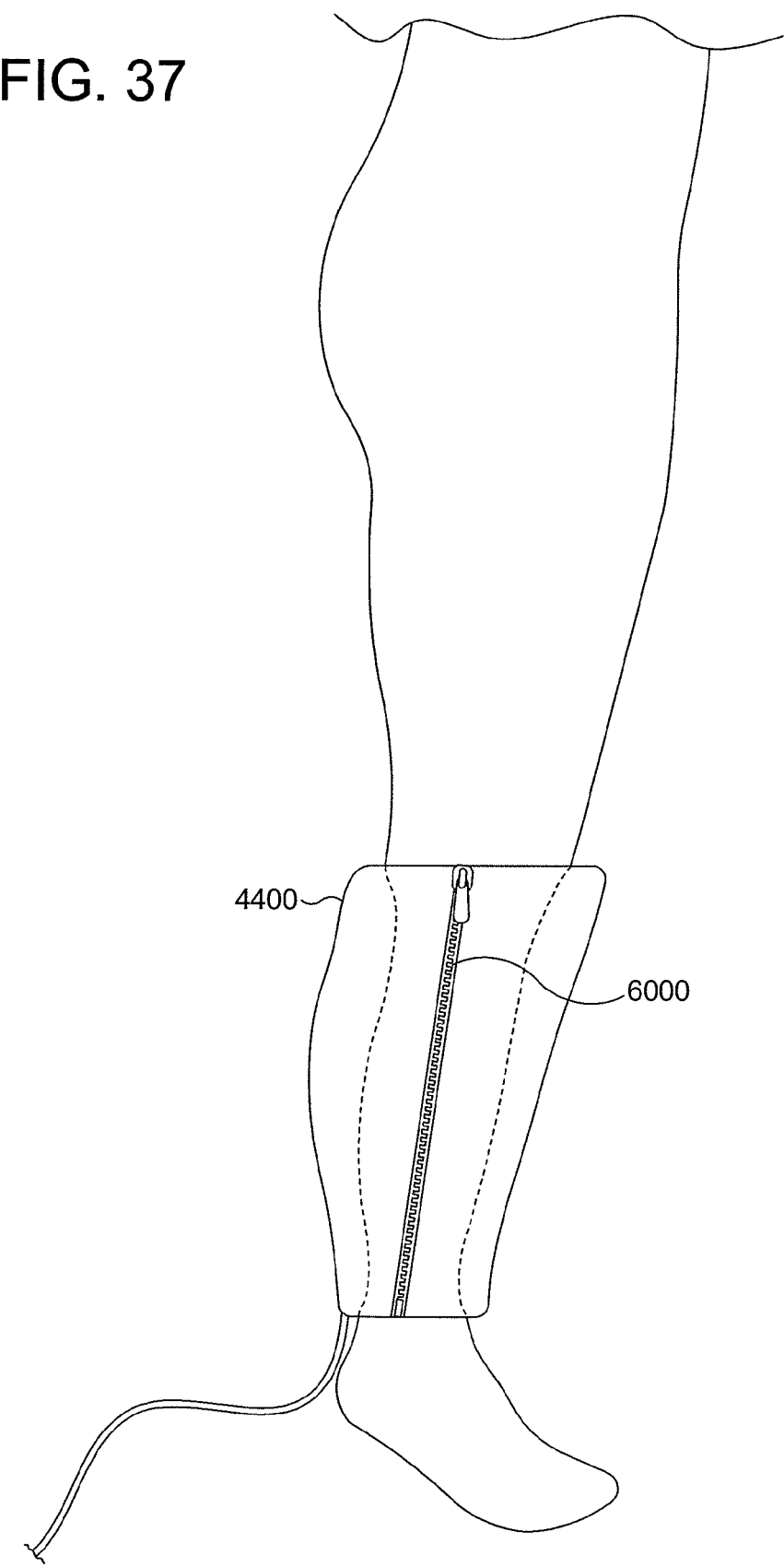
FIG. 37 illustrates a first modification of the external occlusion cuff. The external occlusion cuff of FIG. 37 is similar to the external occlusion cuff of FIG. 36 except that the zip fastener in FIG. 37 is shown extending over the lateral aspect of the patient's calf.
Figure 38:
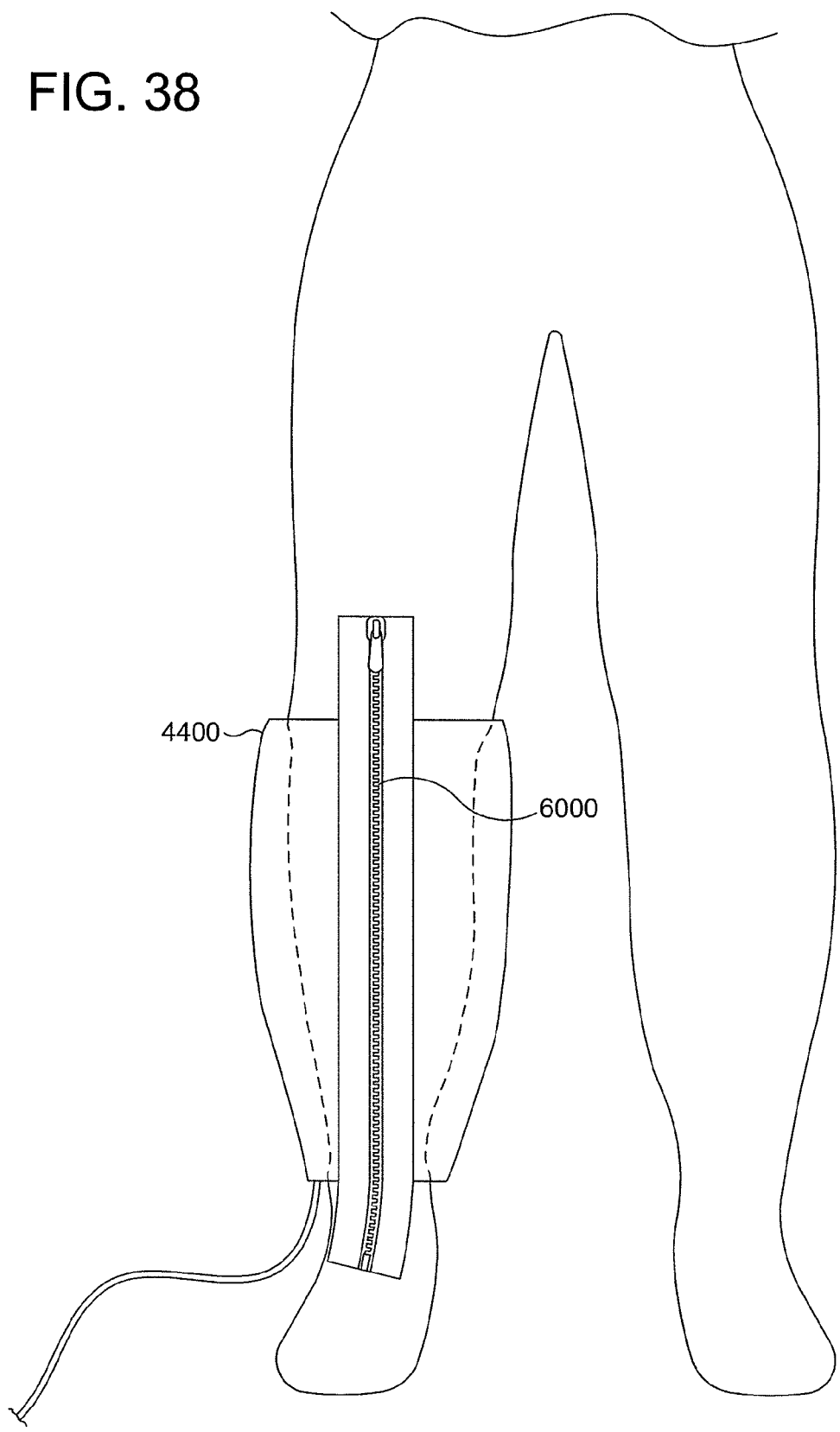
FIG. 38 illustrates a second modification of the external occlusion cuff. The external occlusion cuff of FIG. 38 is similar to the external occlusion cuff of FIG. 37 except that end portions of the zip fastener in FIG. 38 are shown extending beyond the inflatable portion of the cuff in both distal and proximal directions.
Figure 39:
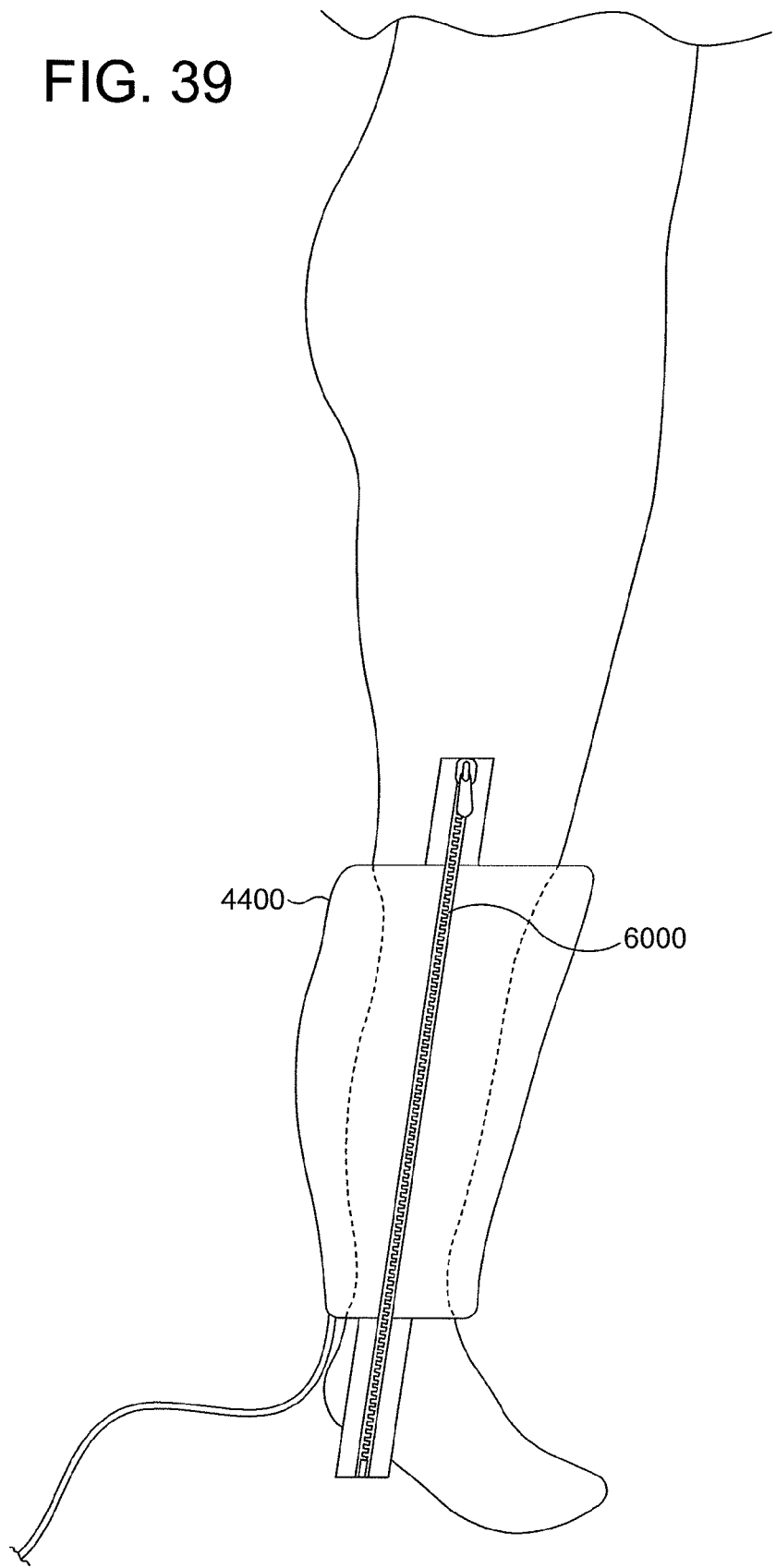
FIG. 39 illustrates a third modification of the external occlusion cuff. The external occlusion cuff of FIG. 39 is similar to the external occlusion cuff of FIG. 38 except that the zip fastener in FIG. 39 is shown extending over the lateral aspect of the patient's calf.
Figure 40:
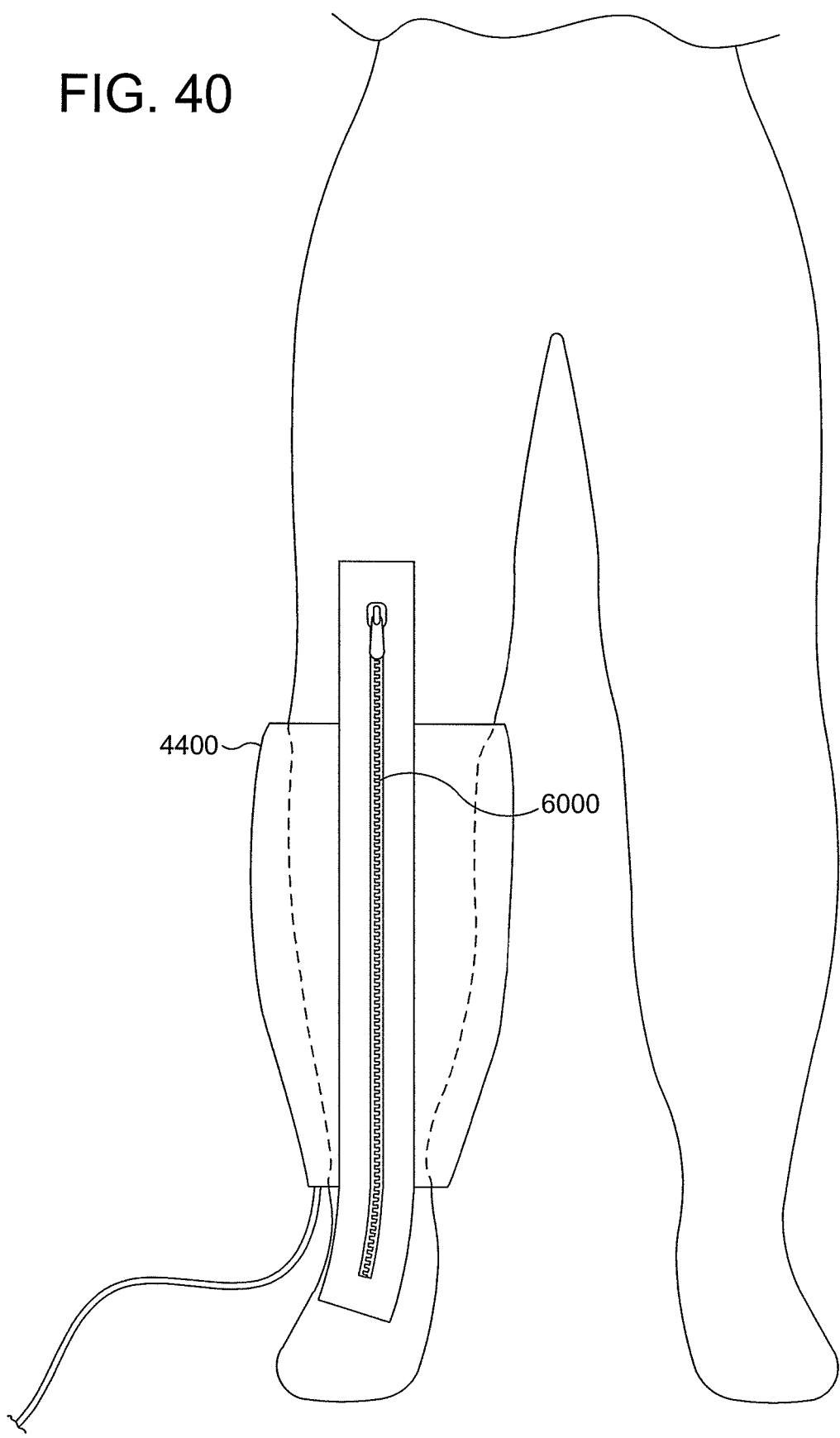
FIG. 40 illustrates a fourth modification of the external occlusion cuff. The external occlusion cuff of FIG. 40 is similar to the external occlusion cuff of FIG. 38 except that the engageable teeth portion of the zip fastener in FIG. 40 does not extend to the distal and proximal ends of the zip fastener, thereby enabling the circumference of the cuff to be enlarged without completely opening it.
Figure 41:
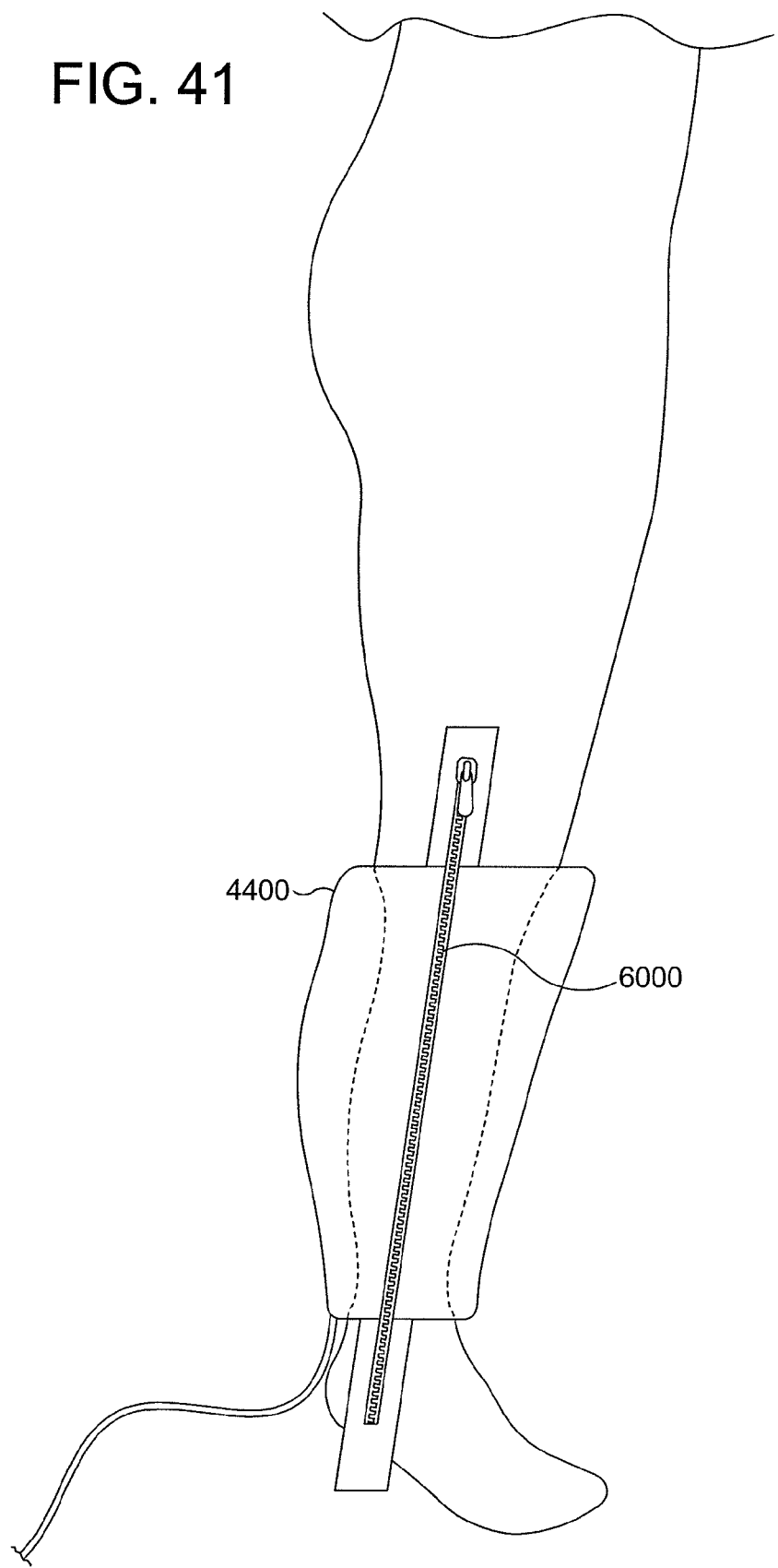
FIG. 41 illustrates a fifth modification of the external occlusion cuff. The external occlusion cuff of FIG. 41 is similar to the external occlusion cuff of FIG. 40 except that the zip fastener in FIG. 41 is shown extending over the lateral aspect of the patient's calf.
Figure 42:
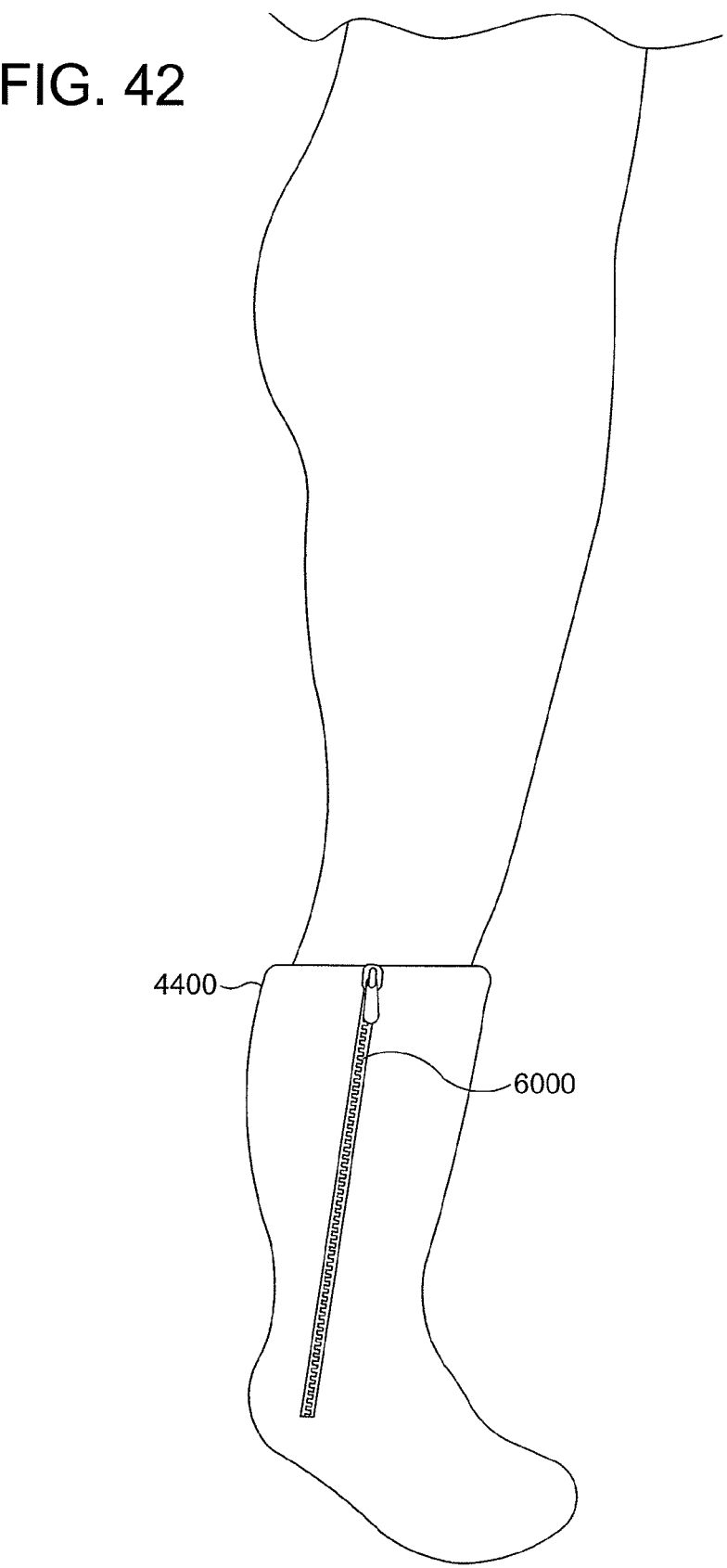
FIG. 42 illustrates a fifth modification of the external occlusion cuff.
Figure 43:
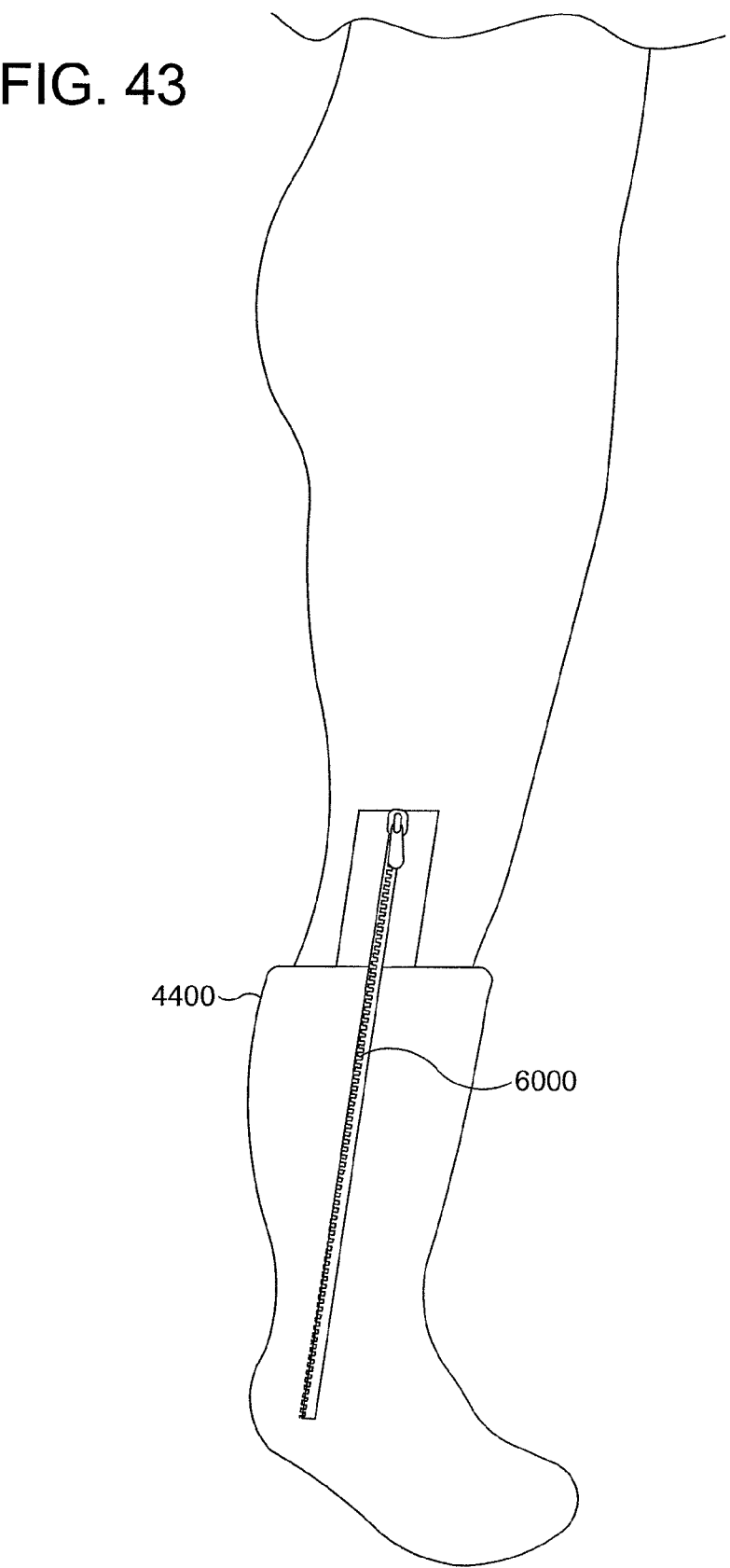
FIG. 43 illustrates a sixth modification of the external occlusion cuff. The external occlusion cuff of FIG. 43 is similar to the external occlusion cuff of FIG. 42 except that the zip fastener of FIG. 43 has a zip fastener portion that extends proximally from the inflatable portion of the cuff.

FIG. 36 illustrates an inflated external occlusion cuff 4400 for occluding the tibial and the most distal segment of the popliteal artery, the cuff comprising a zip fastener 6000 for closing the inflatable cuff in position around the patient's calf. FIG. 30 shows that the zip fastener extends over the patient's tibia (a front aspect of the patient's calf);

FIG. 37 illustrates a first modification of the external occlusion cuff. The external occlusion cuff of FIG. 37 is similar to the external occlusion cuff of FIG. 36 except that the zip fastener in FIG. 37 is shown extending over the lateral aspect of the patient's calf;

FIG. 38 illustrates a second modification of the external occlusion cuff. The external occlusion cuff of FIG. 38 is similar to the external occlusion cuff of FIG. 37 except that end portions of the zip fastener in FIG. 38 are shown extending beyond the inflatable portion of the cuff in both distal and proximal directions;

FIG. 39 illustrates a third modification of the external occlusion cuff. The external occlusion cuff of FIG. 39 is similar to the external occlusion cuff of FIG. 38 except that the zip fastener in FIG. 39 is shown extending over the lateral aspect of the patient's calf;

FIG. 40 illustrates a fourth modification of the external occlusion cuff. The external occlusion cuff of FIG. 40 is similar to the external occlusion cuff of FIG. 38 except that the engageable teeth portion of the zip fastener in FIG. 40 does not extend to the distal and proximal ends of the zip fastener, thereby enabling the circumference of the cuff to be enlarged without completely opening it;

FIG. 41 illustrates a fifth modification of the external occlusion cuff. The external occlusion cuff of FIG. 41 is similar to the external occlusion cuff of FIG. 40 except that the zip fastener in FIG. 41 is shown extending over the lateral aspect of the patient's calf;

FIG. 42 illustrates a fifth modification of the external occlusion cuff. FIG. 42 shows an inflatable occlusion cuff having a shape of a sock and comprising a zip fastener which extends over the lateral aspect of the patient's calf;

FIG. 43 illustrates a sixth modification of the external occlusion cuff. The external occlusion cuff of FIG. 43 is similar to the external occlusion cuff of FIG. 42 except that the zip fastener of FIG. 43 has a zip fastener portion that extends proximally from the inflatable portion of the cuff;

The invention claimed is:

1. A method of using an atherectomy system for removing a stenotic lesion from within a vessel of a patient, the system comprising an atherectomy device and a separate elongate drainage catheter having a drainage lumen for removal of embolic particles produced by the atherectomy device during an atherectomy procedure, the method including:

introducing the atherectomy device and the separate elongate drainage catheter into the patient's vasculature through respective openings located in separate peripheral arteries of the patient, and advancing the separate elongate drainage catheter to a location in which a distal end of the separate drainage catheter is located proximal to a stenotic lesion so that embolic particles produced by the atherectomy device are entrained by retrograde flowing fluid and are aspirated together with the fluid into the drainage lumen of the separate drainage catheter for removal of said embolic particles from the patient's body;

temporarily engaging the atherectomy device and the drainage catheter with each other at a location proximal to the stenotic lesion using an occlusion balloon positioned along one of the atherectomy device and the drainage catheter.

2. The method according to claim 1, comprising inflating the occlusion balloon mounted to a catheter shaft of the drainage catheter for temporarily engaging the atherectomy device and the drainage catheter with each other proximal to the stenotic lesion, wherein said inflating the occlusion balloon at least partially restricts fluid flow through the vessel towards and away from the treated area to assist in the aspiration of retrograde flowing fluid and entrained embolic particles into the drainage lumen of the drainage catheter.

3. The method according to claim 2, wherein the stenotic lesion is located within an internal carotid artery and the method comprises inflating the occlusion balloon to at least partially restrict the fluid flow through a common carotid artery towards and away from the treated stenotic lesion within the internal carotid artery to assist in the aspiration of retrograde flowing fluid and entrained embolic particles into the drainage lumen of the drainage catheter.

4. The method according to claim 1, wherein the occlusion balloon at least partially restricts fluid flow towards and away from the treated stenotic lesion.

5. The method according to claim 1, wherein the atherectomy device comprises a rotational atherectomy device, the rotational atherectomy device comprising an abrasive element mounted to and rotatable together with a flexible drive shaft, the rotatable drive shaft extending through and out of a stationary drive shaft sheath of the atherectomy device.

6. The method according to claim 5, comprising inflating the occlusion balloon mounted along a distal portion of the drainage catheter, the occlusion balloon being inflated within the vessel to engage with the stationary drive shaft sheath while a distal end of the drive shaft sheath extends distally from the stationary drive shaft sheath.

7. The method according to claim 6, comprising inflating the occlusion balloon to a pressure which is sufficient to at least partially restrict the flow of fluids through the vessel towards and away from the treated area, but is insufficient to dilate the vessel.

8. The method according to claim 5, comprising inflating the occlusion balloon mounted to the stationary drive shaft sheath of the atherectomy device, the occlusion balloon being inflated within the vessel proximal to a distal end of the drainage catheter such that the occlusion balloon temporarily engages with the drainage catheter at a position that is proximal to the stenotic lesion.

9. The method according to claim 8, comprising inflating the occlusion balloon to a pressure which is sufficient to at least partially restrict the flow of fluids through the vessel towards and away from the treated area, but is insufficient to dilate the vessel.

10. The method according to claim 5, wherein the drive shaft of the rotational atherectomy device comprises at least one torque transmitting coil and at least one fluid impermeable membrane forming a fluid impermeable wall of the lumen of the drive shaft.

11. The method according to claim 1, wherein said introducing the atherectomy device and the separate elongate drainage catheter comprises introducing the atherectomy device into the patient's vasculature through an opening located in one of the right and left femoral arteries of the patient and introducing the separate elongate drainage catheter through another opening located in the other of the right and left femoral arteries of the patient.

12. The method according to claim 1, wherein said introducing the atherectomy device and the separate elongate drainage catheter comprises introducing the atherectomy device into the patient's vasculature through an opening located in one of a right-side radial artery and a left-side radial artery and introducing the separate elongate drainage catheter through another opening located in the other of the right-side radial artery and the left-side radial artery.

13. The method according to claim 1, wherein said introducing the atherectomy device and the separate elongate drainage catheter comprises introducing the atherectomy device through an opening in one of a femoral artery and a radial artery and introducing the separate elongate drainage catheter through another opening located in the other of the femoral artery and the radial artery.

14. The method according to claim 1, comprising:
placing an external inflatable occlusion cuff around a lower extremity such that a proximal end of the external inflatable occlusion cuff is located distal to and spaced away from the stenotic lesion located in at least one of a ipsilateral iliac artery, a superficial femoral artery, and popliteal artery of said extremity; and
inflating the external inflatable occlusion cuff to a pressure which is sufficient to restrict the flow of fluids at least through anterior and posterior tibial arteries of the lower extremity.

15. The method according to claim 14, wherein the external inflatable occlusion cuff is placed around the lower extremity such a distal end of the external inflatable occlusion cuff is located proximate to the patient's ankle.

16. The method according to claim 14, wherein the external inflatable occlusion cuff comprises a sock device that extends distally from about the patient's knee.

17. The method according to claim 14, wherein the external inflatable occlusion cuff is configured to be opened and closed around the lower extremity along a longitudinally extending line, said line extending longitudinally distally from the proximal end of the cuff.

18. The method according to claim 17, wherein the external inflatable occlusion cuff comprises a zipper to open and close the external inflatable occlusion cuff along said longitudinally extending line.

19. The method according to claim 1, wherein the atherectomy device comprises a rotational atherectomy device, the rotational atherectomy device comprising: a flexible drive shaft including at least one torque transmitting coil and at least one fluid flow lumen extending along a longitudinal axis of the drive shaft; an eccentric abrasive element fixed to the flexible drive shaft and having a center of mass that is offset from the longitudinal axis of the flexible drive shaft; and a pair of inflatable counterweights fixed to the flexible drive shaft, being in fluid communication with the fluid flow lumen of the drive shaft, and being substantially equaled spaced apart from the eccentric abrasive element on opposing sides of the eccentric abrasive element.

20. The method according to claim 19, wherein said fluid flow lumen extending along the longitudinal axis of the drive shaft is closed at a distal-most tip of the drive shaft, wherein the rotational atherectomy device further comprises an elongate core element slidable within the fluid flow lumen of the drive shaft, the elongate core element comprising a central lumen in fluid communication with the fluid flow lumen of the drive shaft.

* * * * *